United States Patent
Rees et al.

(10) Patent No.: US 10,517,301 B2
(45) Date of Patent: *Dec. 31, 2019

(54) COMPOSITIONS AND METHODS FOR ENHANCING PLANT QUALITY

(71) Applicant: BAYER CROPSCIENCE LP, Research Triangle Park, NC (US)

(72) Inventors: Richard Rees, Chapel Hill, NC (US); James Rutledge, Durham, NC (US); Mike Newman, Willow Springs, NC (US)

(73) Assignee: BAYER CROPSCIENCE LP, Research Triangle, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/699,378

(22) Filed: Sep. 8, 2017

(65) Prior Publication Data

US 2017/0367346 A1 Dec. 28, 2017

Related U.S. Application Data

(63) Continuation of application No. 13/666,631, filed on Nov. 1, 2012, now Pat. No. 9,820,490.

(60) Provisional application No. 61/715,155, filed on Oct. 17, 2012, provisional application No. 61/555,142, filed on Nov. 3, 2011.

(51) Int. Cl.
| | | |
|---|---|---|
| A01N 37/10 | (2006.01) | |
| A01N 47/34 | (2006.01) | |
| A01N 57/12 | (2006.01) | |
| A01N 59/26 | (2006.01) | |

(52) U.S. Cl.
CPC ............ *A01N 59/26* (2013.01); *A01N 37/10* (2013.01); *A01N 47/34* (2013.01); *A01N 57/12* (2013.01)

(58) Field of Classification Search
None
See application file for complete search history.

(56) References Cited

U.S. PATENT DOCUMENTS

| | | |
|---|---|---|
| 5,599,804 A | 2/1997 | Mudge et al. |
| 5,643,852 A | 7/1997 | Lucas et al. |
| 6,040,273 A | 3/2000 | Dean et al. |
| RE42,394 E | 5/2011 | Mudge et al. |
| 8,377,850 B2 | 2/2013 | Vandenberg et al. |
| 9,820,490 B2 * | 11/2017 | Rees ............... A01N 37/10 |
| 2008/0194755 A1 | 8/2008 | Derudder et al. |
| 2008/0280763 A1 | 11/2008 | Hodge et al. |
| 2010/0291229 A1 | 11/2010 | Surrena et al. |
| 2010/0292202 A1 | 11/2010 | Vandenberg et al. |

FOREIGN PATENT DOCUMENTS

| | | | |
|---|---|---|---|
| CN | 1973627 A | * | 6/2007 |
| WO | 1997/037524 | | 10/1997 |
| WO | 2006/128677 | | 12/2006 |
| WO | 2009/126370 | | 10/2009 |
| WO | 2010/115721 | | 10/2010 |
| WO | 2010/132169 | | 11/2010 |

OTHER PUBLICATIONS

Fiata Stressgard Label.
Signature XTRA Stressgard Label.
Brunings et al., "Fungicidal Activity of Phosphous Acids", PNW Plant Disease Management Handbook 2005.
Riverside Magellan Label 2002.
Harbour et al., "Photochemistry of organic pigment dispersions: Phthalocyanine-mediated photoproduction of hydrogen peroxide," J Am Chem Soc 102: 1874-1876 (1980).
Bio-Forge—Jul. 2011 [downloaded on Sep. 1, 2014 from the website https://web.archive.org/web/20110716040003/http://www.stollerusa.com/productdetail?id=13594].
Landschoot et al., "Sorting out the phosphonate products", GCM, pp. 73-76, Nov. 2005.
International Search Report and Written Opinion based on PCT/US2012/062935, dated May 7, 2013.
Invitation to Pay Additional Fees and Where Applicable. Protest Fee/Communication Relating to the Results of the Partial International Search based on Application No. PCT/US2012/062935, dated Feb. 25, 2013.

* cited by examiner

*Primary Examiner* — Abigail Vanhorn
(74) *Attorney, Agent, or Firm* — McBee Moore Woodward & Vanik IP, LLC

(57) ABSTRACT

Presented herein are compositions comprising an antioxidant (i), a radiation manager (ii), and one or more of, a plant strengthener (iii), or a plant growth regulator (iv). Also presented herein are compositions comprising a plant strengthener (iii), and one or more of, an antioxidant (i), or a radiation manager comprising a polyoxyalkylene UV absorber (ii). Furthermore, methods of using the disclosed compositions are also provided.

12 Claims, 32 Drawing Sheets

EXAMPLE 1(B)(1a) - VISUAL QUALITY RATING FOR BENTGRASS UNDER FULL IRRIGATION INVENTION COMPOSITIONS (2), (4), (6), AND (8)

EXAMPLE 1(B)(1a) - VISUAL QUALITY RATING FOR BENTGRASS UNDER 25% REDUCED IRRIGATION USING INVENTION COMPOSITIONS (1), (3), (5), AND (7)

EXAMPLE 1(B)(1a) - VISUAL QUALITY RATING FOR BENTGRASS UNDER 25% REDUCED IRRIGATION USING INVENTION COMPOSITIONS (2), (4), (6), AND (8)

EXAMPLE 1(B)(1a) - VISUAL QUALITY RATING FOR BENTGRASS UNDER 50% REDUCED IRRIGATION USING INVENTION COMPOSITIONS (2), (4), (6), AND (8)

EXAMPLE 1(B)(1a) - VISUAL QUALITY RATING FOR BERMUDAGRASS UNDER FULL IRRIGATION USING INVENTION COMPOSITIONS (1), (3), (5), AND (7)

EXAMPLE 1(B)(1a) - VISUAL QUALITY RATING FOR BERMUDAGRASS UNDER 50% REDUCED IRRIGATION USING INVENTION COMPOSITIONS (1), (3), (5), AND (7)

EXAMPLE 1(B)(1a) - VISUAL QUALITY RATING FOR ZOYSIAGRASS UNDER 50% REDUCED IRRIGATION USING INVENTION COMPOSITIONS (1), (3), (5), AND (7)

EXAMPLE 1(B)/(1a) - VISUAL QUALITY RATING FOR ZOYSIAGRASS UNDER 50% REDUCED IRRIGATION USING INVENTION COMPOSITIONS (2), (4), (6), AND (8)

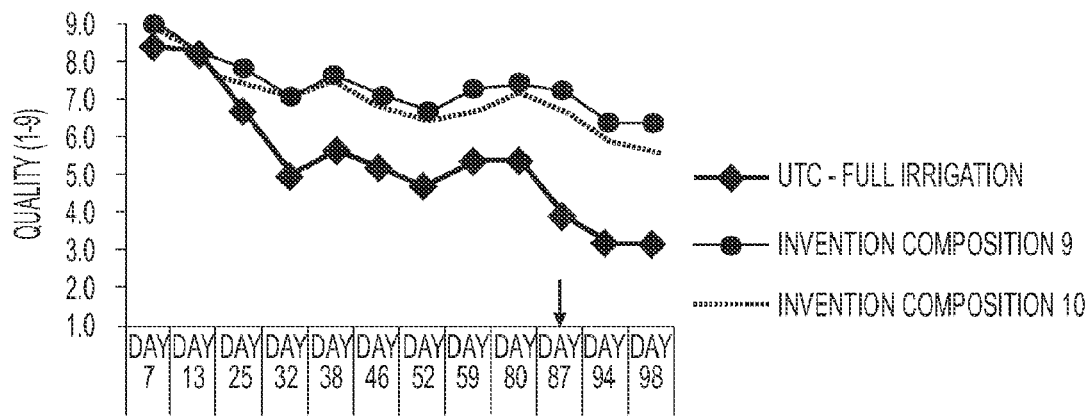
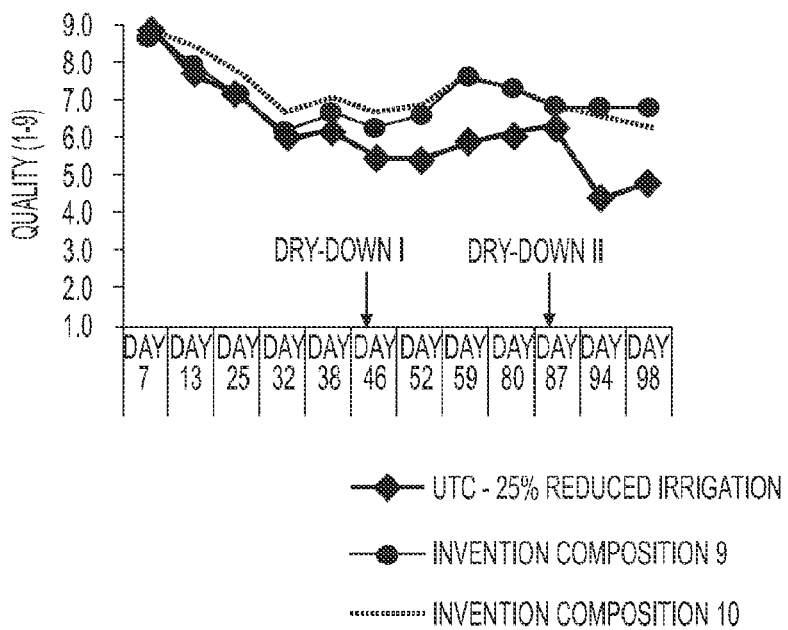
FIG. 18

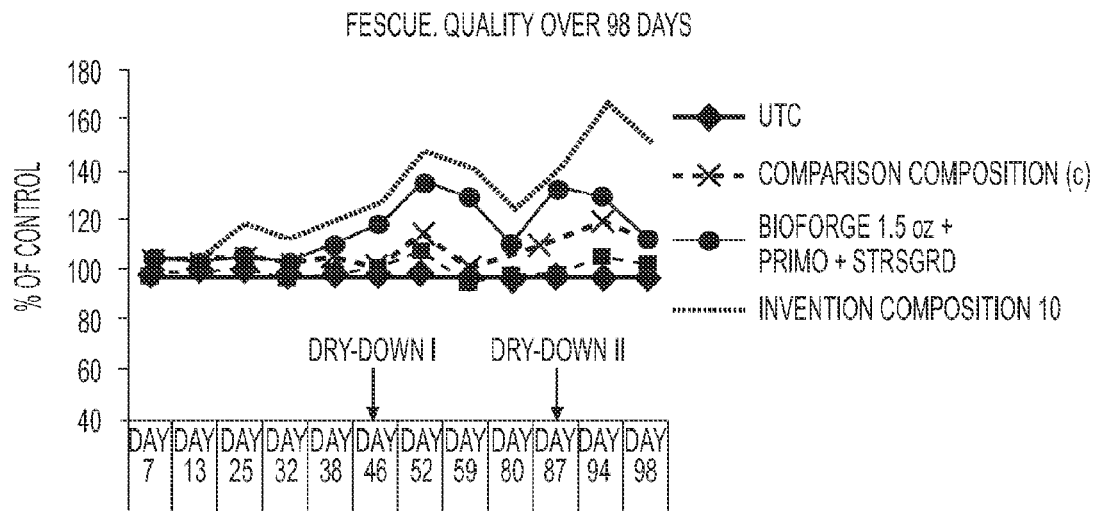
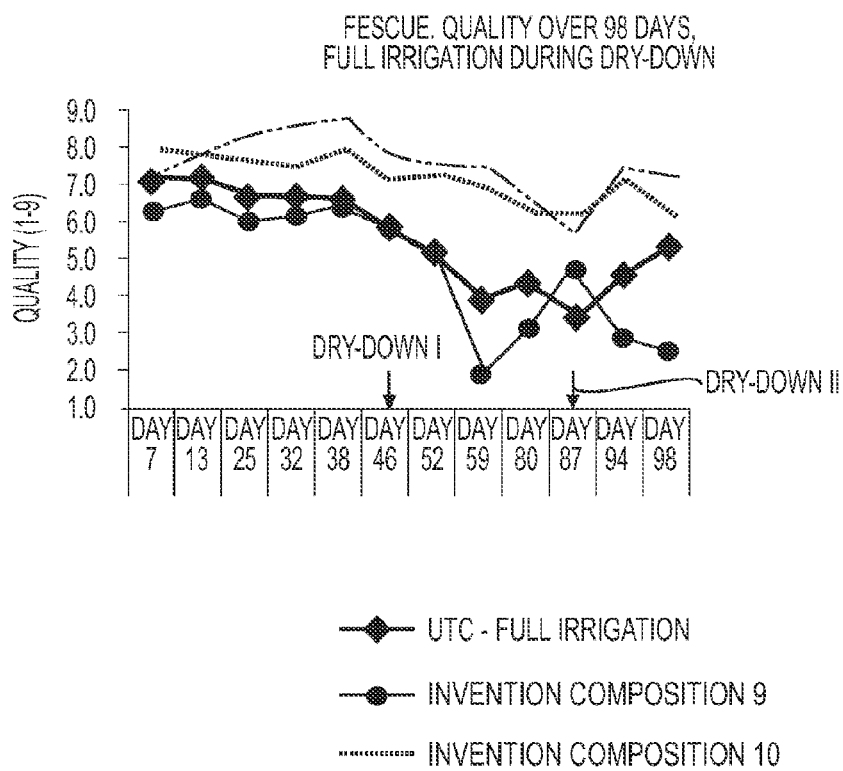
*FIG. 20*

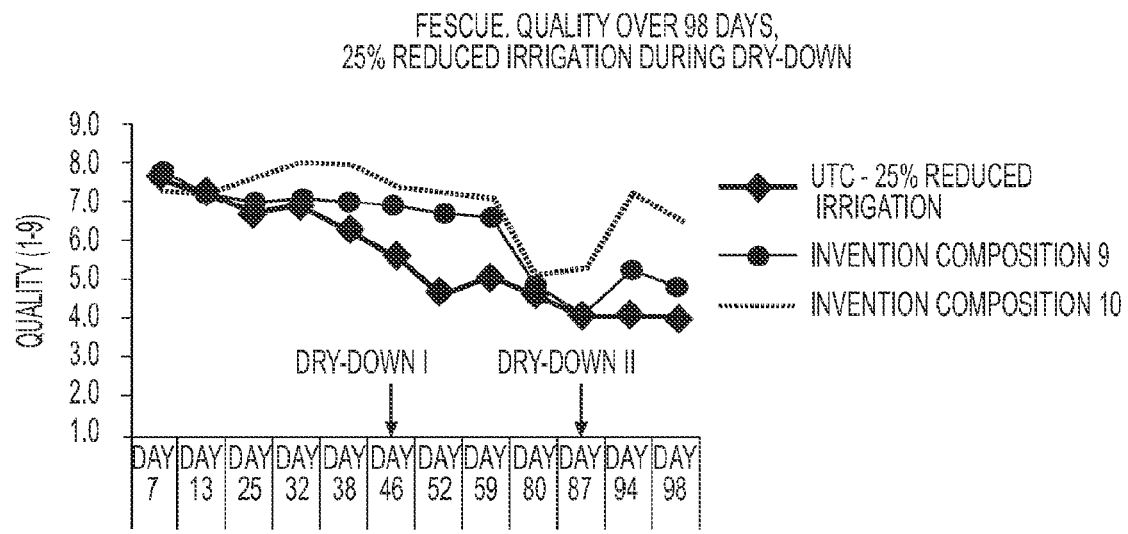
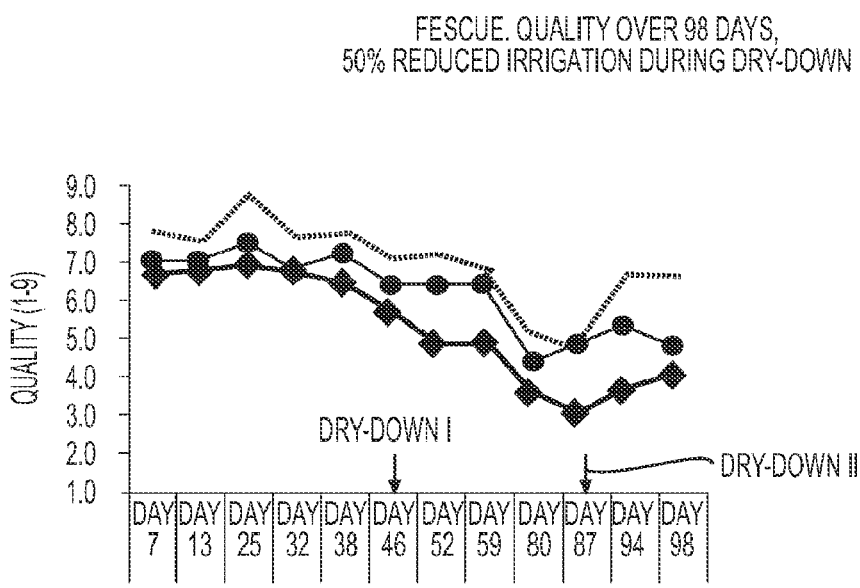
FIG. 21 i. UNTREATED
ii. COMPARISON COMPOSITION (a) + SURFACTANT
iii. COMPARISON COMPOSITION (b)
iv. COMPARISON COMPOSITION (c)
v. COMPARISON COMPOSITION (d)
vi. INVENTION COMPOSITION 9
vii. COMPARISON COMPOSITION (e)
viii. INVENTION COMPOSITION 10
ix. COMPARISON COMPOSITION (f)

COMPOSITIONS AND METHODS FOR ENHANCING PLANT QUALITY

CROSS REFERENCE TO RELATED APPLICATIONS

This application is a continuation of U.S. application Ser. No. 13/666,631, filed Nov. 1, 2012, which claims priority to U.S. Provisional Application No. 61/555,142, filed Nov. 3, 2011, and U.S. Provisional Application No. 61/715,155, filed Oct. 17, 2012, the contents of which are hereby incorporated by reference in their entireties.

FIELD

This application is directed to compositions comprising an antioxidant (i), a radiation manager (ii), and one or more of, a plant strengthener (iii), or a plant growth regulator (iv). Also presented herein are compositions comprising a plant strengthener (iii), and one or more of, an antioxidant (i), or a radiation manager comprising a polyoxyalkylene UV absorber (ii). Furthermore, methods of using the disclosed compositions are also provided.

BACKGROUND

Grass lawns are a dominant landscape feature of many residences and recreational areas. Although grass lawns provide open views and a wear-tolerant soft surface for active recreation, the time, cost and environmental impact of watering grass lawns have been increasingly scrutinized by municipalities and private owners alike, particularly in areas prone to drought-like conditions or where water is a limited resource.

During the summer season, municipal water consumption can double as a result of lawn watering. Excess water consumption lowers water tables and reduces stream flows, which affects fish and other aquatic life. It also increases the costs for municipalities to supply and treat water and increases the cost of water bills. To reduce cost, some municipalities restrict lawn and garden water use when there is little rainfall.

Alternatives that provide low-water maintenance of grass lawns present a positive contribution towards water conservation efforts. To that end, blends of varying grasses selected for beneficial sun/shade tolerance are offered as an "eco-friendly" solution for low maintenance turf. However, these grass blends do not readily provide certain physical properties, such as uniformity, durability, texture (e.g., for putting surfaces), and vivid green color, sought in turf grass grown on golf course greens, golf fairways and tee boxes.

Most turf managers are aware that turfgrass water use is under increasing scrutiny, as there is particular interest in reducing irrigation on recreational areas, such as golf courses in particular. Consequently, many turf managers are interested in improving their turf's drought tolerance. Thus, there remains a need for compositions and methods to reduce water stress in grass under conditions of reduced water irrigation. There is also a need for such compositions and methods to impart improved grass quality, density, color, or plant cell turgidity.

SUMMARY

Presented herein are compositions comprising:
(i) an antioxidant;
(ii) a radiation manager; and
one or more of
(iii) a plant strengthener, or
(iv) a plant growth regulator.
Also presented herein are compositions comprising:
(i) an antioxidant;
(ii) a radiation manager; and
(iii) a plant strengthener.
Also presented herein are compositions comprising:
(i) an antioxidant;
(ii) a radiation manager; and
(iv) a plant growth regulator.
Also presented herein are compositions comprising:
(i) an antioxidant;
(ii) a radiation manager;
(iii) a plant strengthener; and
(iv) a plant growth regulator.
Also presented herein are compositions consisting essentially of, or consisting of:
(i) an antioxidant;
(ii) a radiation manager; and
one or more of
(iii) a plant strengthener, or
(iv) a plant growth regulator.
Also presented herein are synergistic compositions comprising:
(i) an antioxidant;
(ii) a radiation manager; and
one or more of
(iii) a plant strengthener, or
(iv) a plant growth regulator.
In further embodiments, the disclosure presents a composition comprising:
(i) at least one antioxidant produced by the reaction of a carboxylic acid and a urea;
(ii) a radiation manager; and
one or more of
(iii) a plant strengthener, or
(iv) a plant growth regulator.
wherein said (i) antioxidant corresponds to formula (I):

$$R_1 \underset{O}{\overset{O}{\|}} {-}\underset{R_3}{\overset{}{N}}{-}\underset{O}{\overset{O}{\|}}{-}\underset{R_4}{\overset{}{N}}{-}\underset{O}{\overset{O}{\|}}{-} R_2 \quad (I)$$

where $R_1$, $R_2$, $R_3$, and $R_4$ are the same or different and are selected from the group consisting of hydrogen, substituted and unsubstituted alkyl, allyl, vinyl and alkoxyl groups having from one to six carbon atoms, substituted and unsubstituted phenyl groups, and halides. Compositions above can be used to effectively improve plant growth under a condition of reduced water irrigation.

In other embodiments, the disclosure provides for compositions comprising:
 (iii) a plant strengthener; and
 one or more of
 (i) an antioxidant, or
 (ii) a radiation manager comprising a polyoxyalkylene UV absorber.

The disclosure also provides for compositions comprising:
 (iii) a plant strengthener; and
 (i) an antioxidant.

The disclosure also provides for compositions comprising:
 (iii) a plant strengthener; and
 (ii) a radiation manager comprising a polyoxyalkylene UV absorber.

All compositions disclosed herein can be used to effectively improve plant growth and health under a condition of reduced water irrigation.

Also presented herein are methods for making a composition to apply to a plant under a condition of reduced water irrigation, said method comprising:
 (i) producing at least one antioxidant by reacting
  (a) a carboxylic acid having the formula RCOOH where R is selected from the group consisting of hydrogen, substituted and unsubstituted alkyl, allyl vinyl, and alkoxyl groups having from 1-6 carbon atoms, substituted and unsubstituted phenyl group, and halides; and
  (b) a urea having the formula $(NHR')_2CO$ where each R' is the same or different and is selected from the group consisting of hydrogen, substituted and unsubstituted alkyl groups having from 1-6 carbon atoms, substituted and unsubstituted alkoxyl groups having from 1-6 carbon atoms, substituted and unsubstituted phenyl groups, and halides;
 (ii) mixing the antioxidant produced in step (i) with:
  at least one radiation manager and
  with one or more of a plant strengthener or a plant growth regulator.

Further, presented herein are methods for improving plant quality, density, color, or plant cell turgidity under a condition of reduced water irrigation, said method comprising applying to said plant a composition comprising:
 (i) an antioxidant;
 (ii) a radiation manager; and
 one or more of
 (iii) a plant strengthener, or
 (iv) a plant growth regulator.

Presented herein are methods for improving plant quality, density, color, or plant cell turgidity under a condition of reduced water irrigation, said method comprising applying to said plant a composition comprising:
 (i) an antioxidant;
 (ii) a radiation manager; and
 (iii) a plant strengthener.

Presented herein are methods for improving plant quality, density, color, or plant cell turgidity under a condition of reduced water irrigation, said method comprising applying to said plant a composition comprising:
 (i) an antioxidant;
 (ii) a radiation manager; and
 (iv) a plant growth regulator.

Presented herein are methods for improving plant quality, density, color, or plant cell turgidity under a condition of reduced water irrigation, said method comprising applying to said plant a composition comprising:
 (i) an antioxidant;
 (ii) a radiation manager;
 (iii) a plant strengthener; and
 (iv) a plant growth regulator.

Further presented herein are methods for improving plant quality, density, color, or plant cell turgidity under a condition of reduced water irrigation, said method comprising applying to said plant a composition comprising:
 (iii) a plant strengthener; and
 one or more of
 (i) an antioxidant, or
 (ii) a radiation manager comprising a polyoxyalkylene UV absorber.

Also presented herein are methods for improving plant quality, density, color, or plant cell turgidity under a condition of reduced water irrigation, said method comprising applying to said plant a composition comprising:
 (iii) a plant strengthener; and
 (i) an antioxidant.

The disclosure also provides for methods for improving plant quality, density, color, or plant cell turgidity under a condition of reduced water irrigation, said method comprising applying to said plant a composition comprising:
 (iii) a plant strengthener; and
 (ii) a radiation manager comprising a polyoxyalkylene UV absorber.

In certain embodiments, methods for improving plant quality, density, color, or plant cell turgidity are performed before, during, or after a condition of reduced water irrigation.

In certain embodiments, plants exhibit improved green color, chlorophyll, shoot density, shoot fresh/dry weight, root fresh/dry weight, canopy temperature, and/or plot soil moisture after treatment with compositions presented herein.

In certain embodiments, plants treated with compositions presented herein exhibit improved green color, chlorophyll, shoot density, shoot fresh/dry weight, root fresh/dry weight, canopy temperature, and/or plot soil moisture during and/or after the condition of reduced water irrigation.

It is understood that compositions and methods "consisting essentially of" and "consisting of" the recited elements, or any combination thereof, are also covered by the present disclosure.

Further, the present disclosure may also comprise compositions and methods that recite any of the components (i) thru (iv), together in any combination.

Furthermore, in certain embodiments, the present compositions specifically exclude non-recited components, i.e. compositions with a negative proviso that any particular component (i)-(iv) is not present are covered.

BRIEF DESCRIPTION OF THE DRAWINGS

These and other features, aspects, and advantages of embodiments of the present invention will become better understood with regard to the following description, appended claims, and accompanying drawings, where:

FIG. 18: shows results of an experiment on Bentgrass quality over 98 days.

FIG. 20: shows results of an experiment on Fescue quality over 98 days.

FIG. 21: shows results of an experiment on Fescue quality over 98 days.

DETAILED DESCRIPTION

Figure 1:
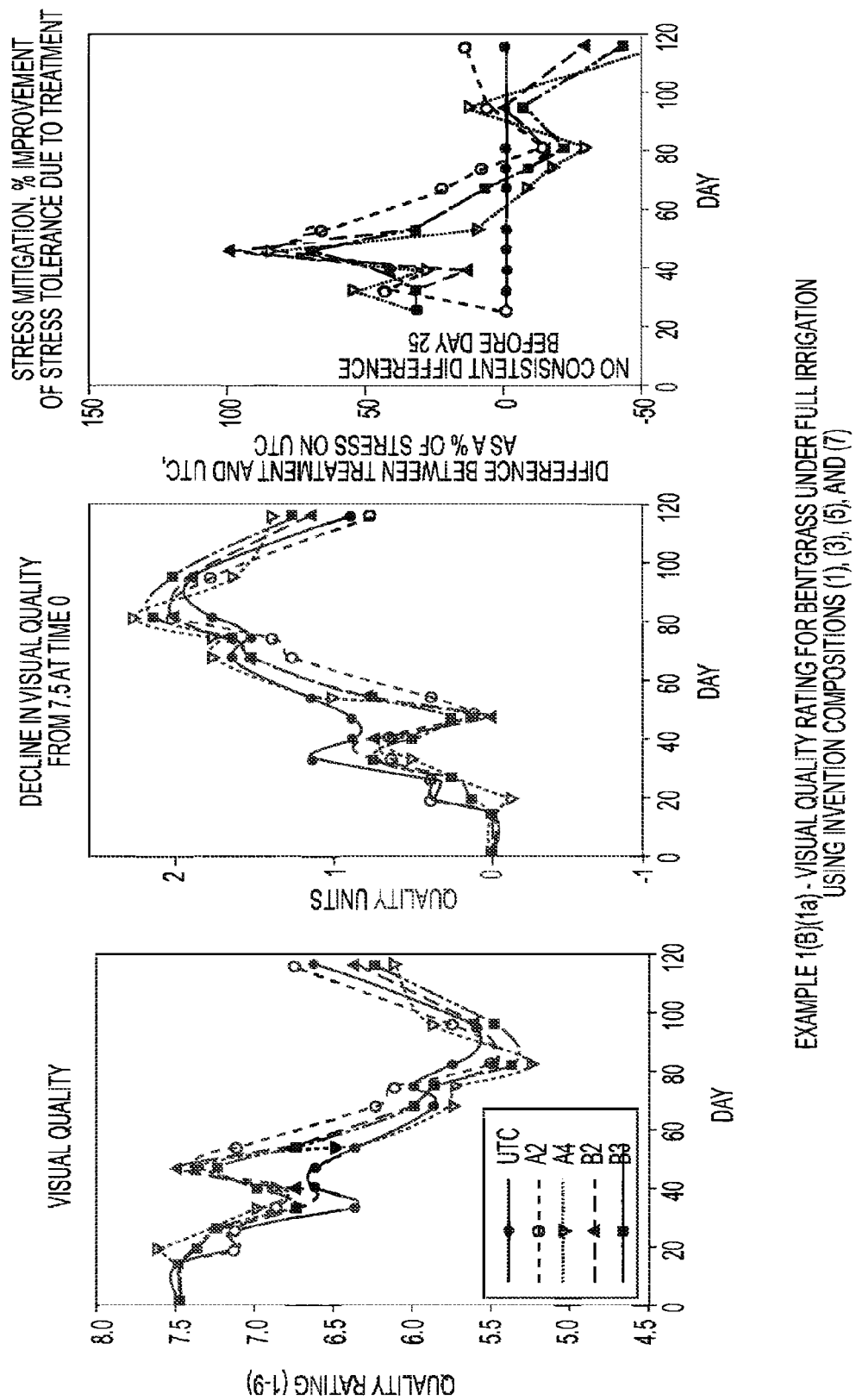
FIG. 1: shows results from a visual quality rating experiment.
Figure 2:
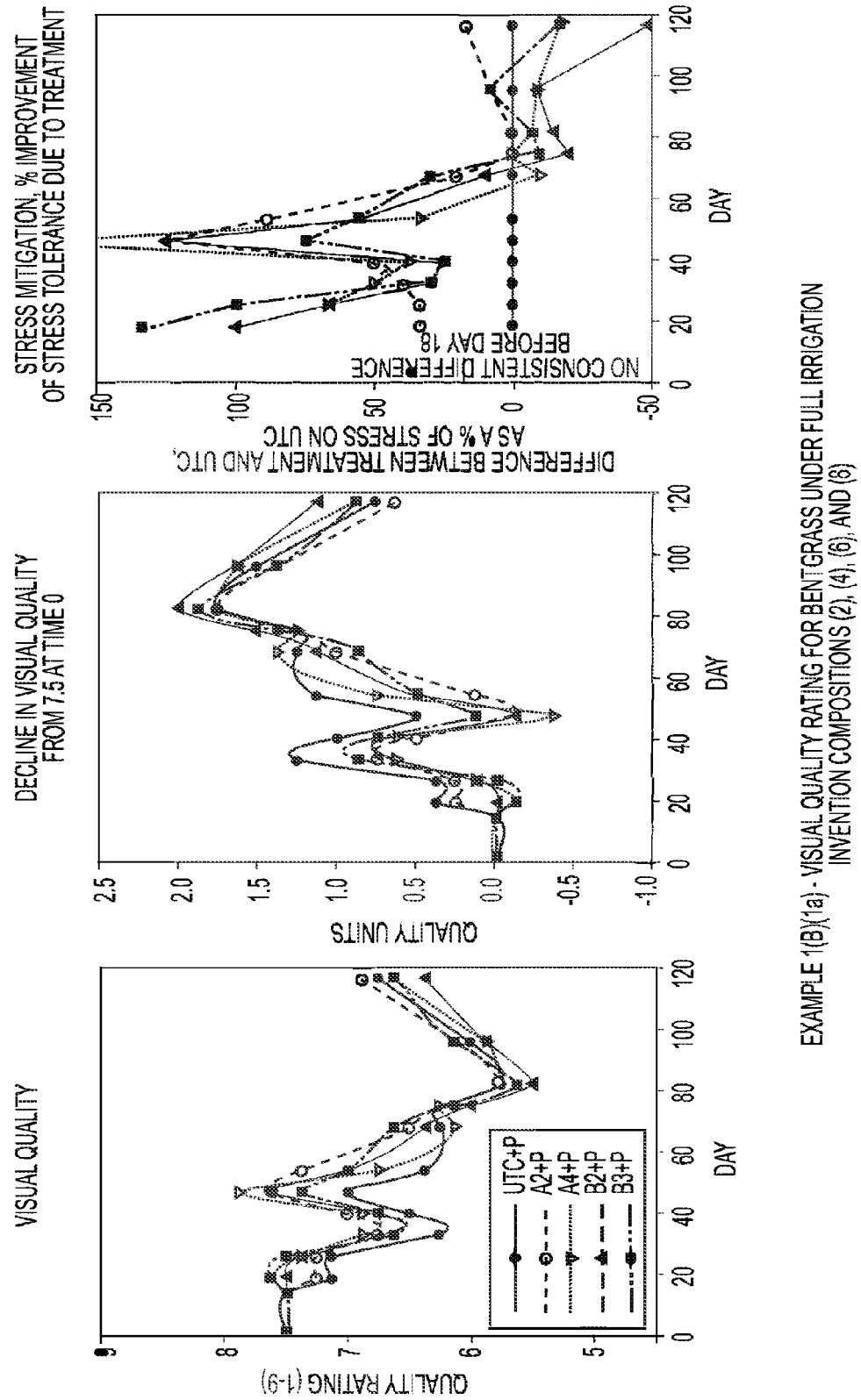
FIG. 2: shows results from a visual quality rating experiment.
Figure 3:
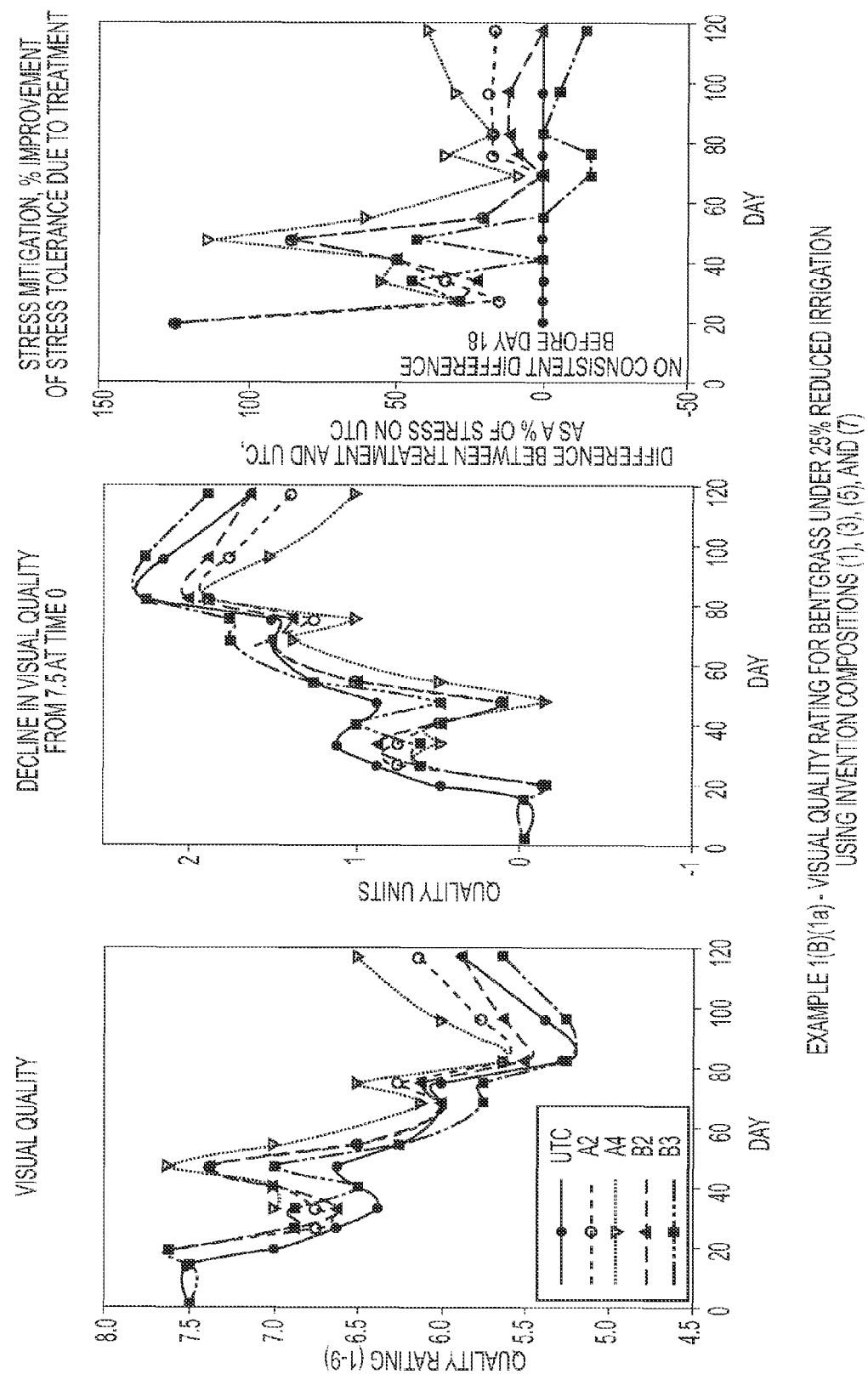
FIG. 3: shows results from a visual quality rating experiment.
Figure 4:
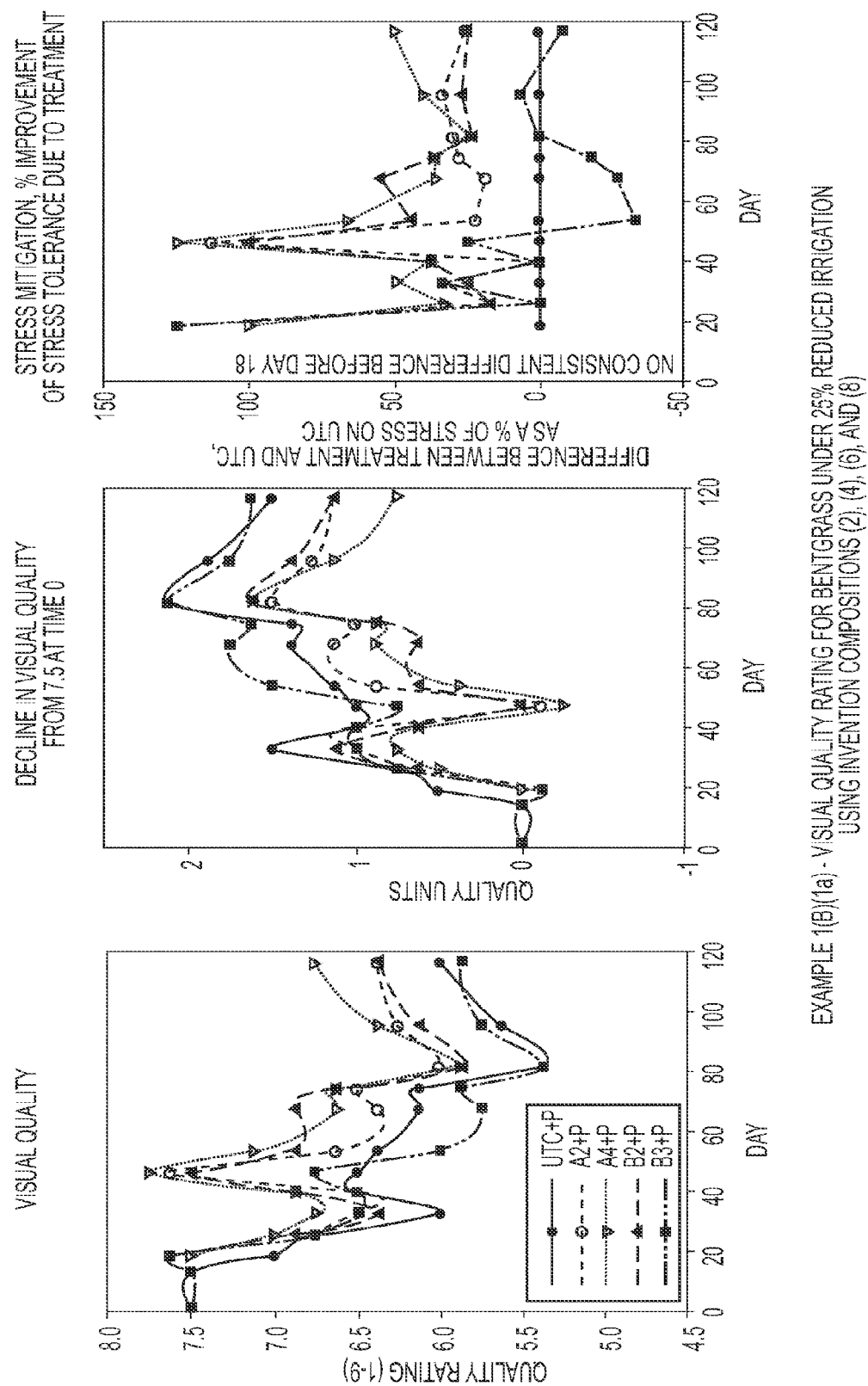
FIG. 4: shows results from a visual quality rating experiment.
Figure 5:
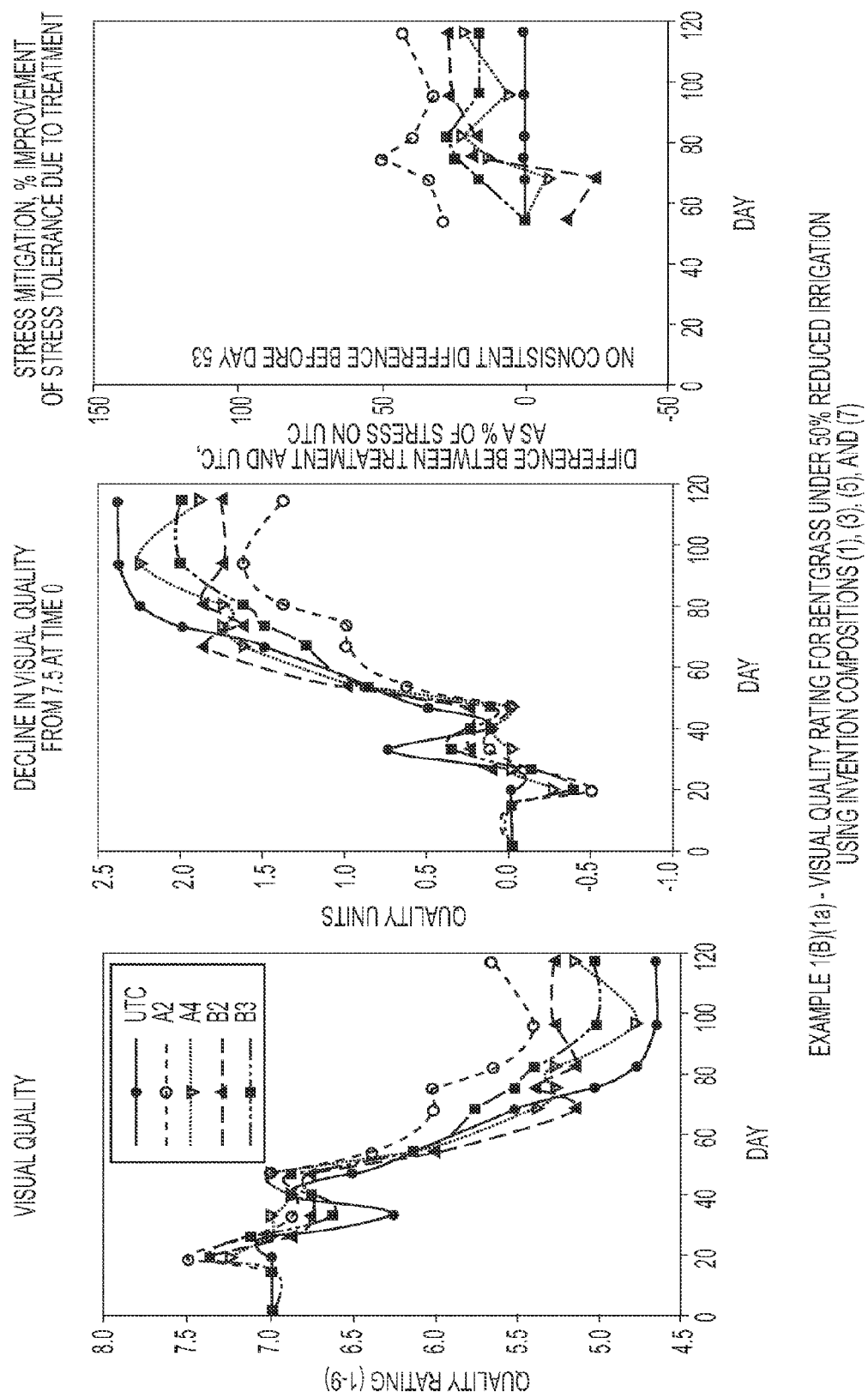
FIG. 5: shows results from a visual quality rating experiment.
Figure 6:
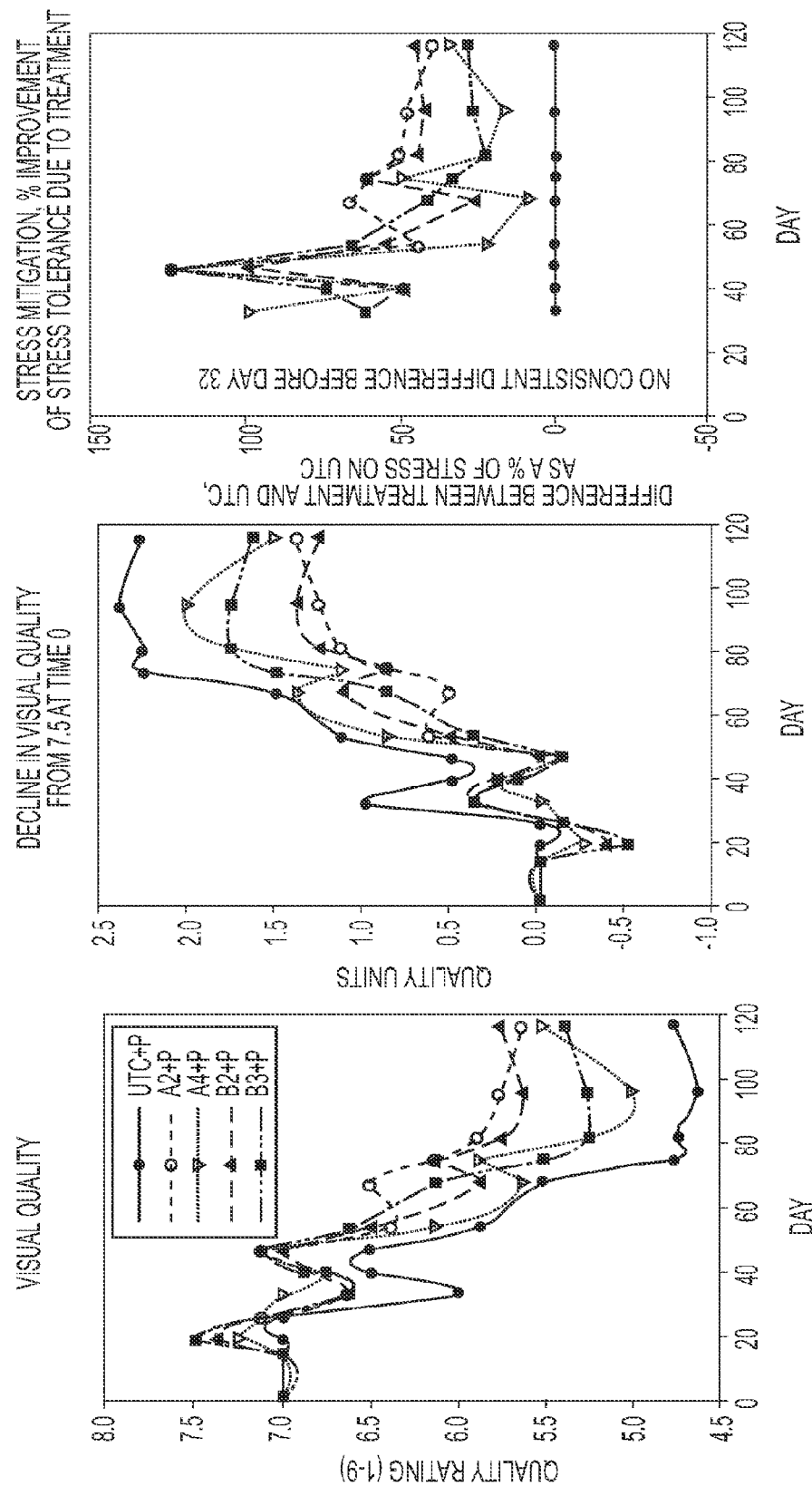
FIG. 6: shows results from a visual quality rating experiment.
Figure 7:
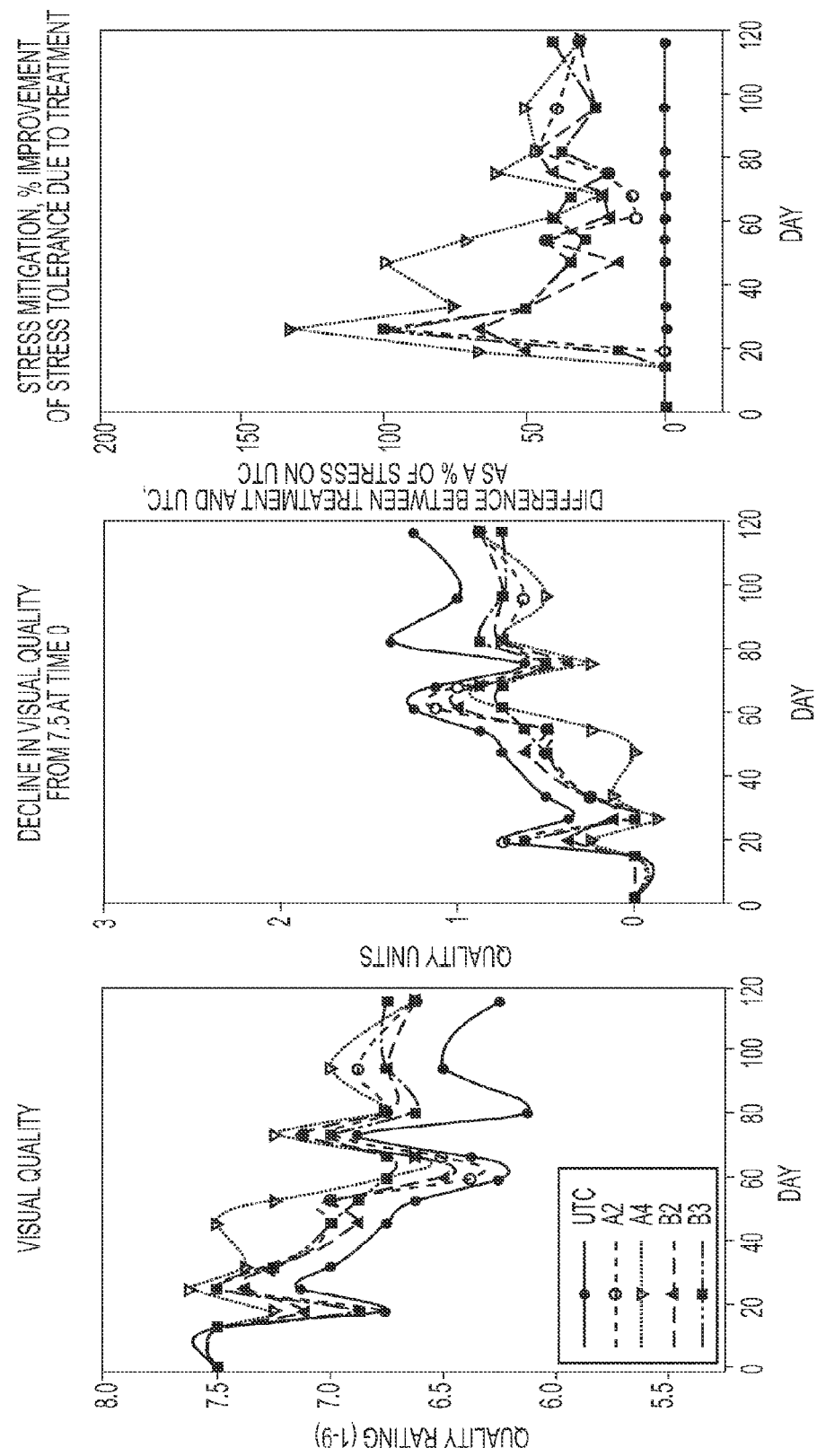
FIG. 7: shows results from a visual quality rating experiment.
Figure 8:
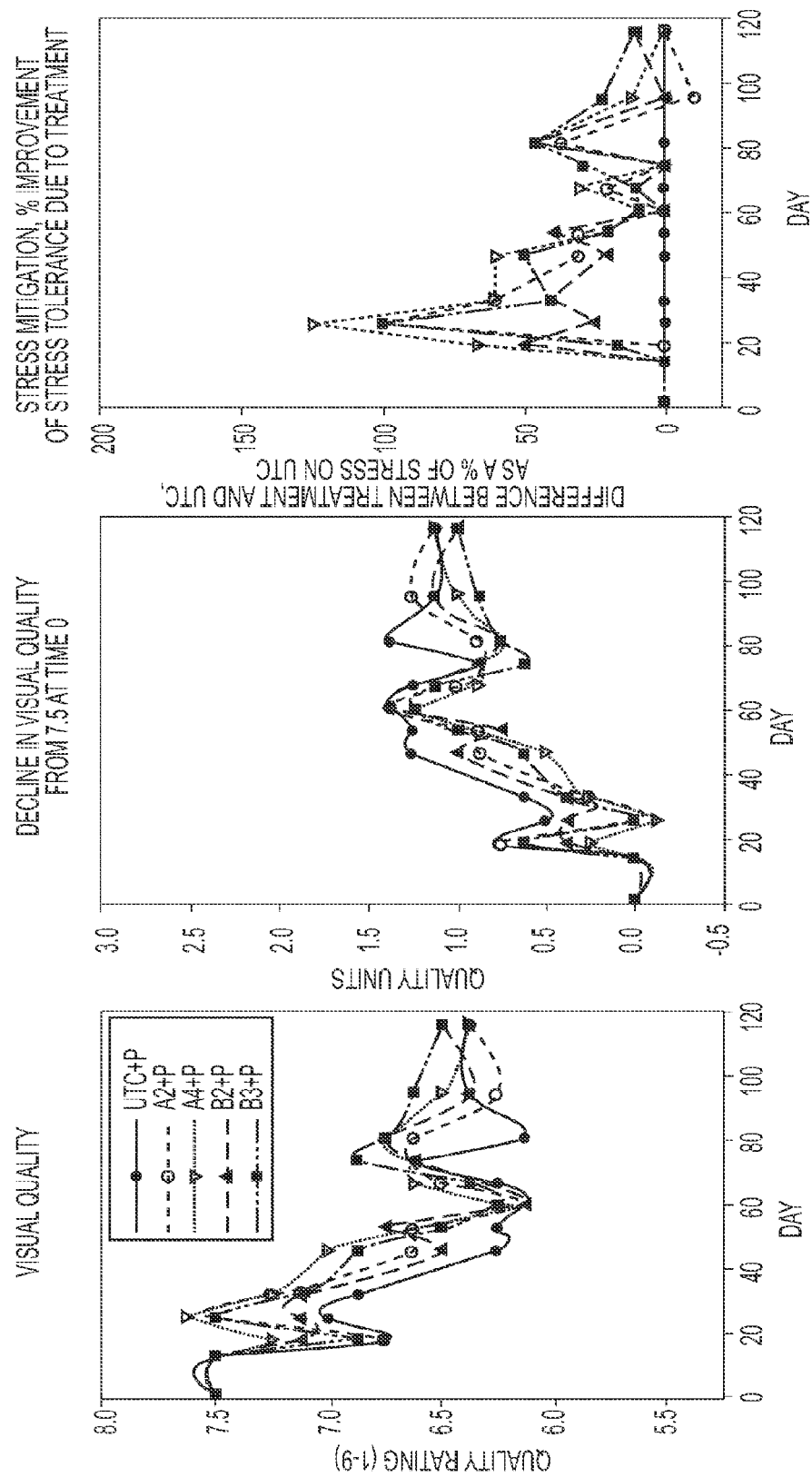
FIG. 8: shows results from a visual quality rating experiment.
Figure 9:
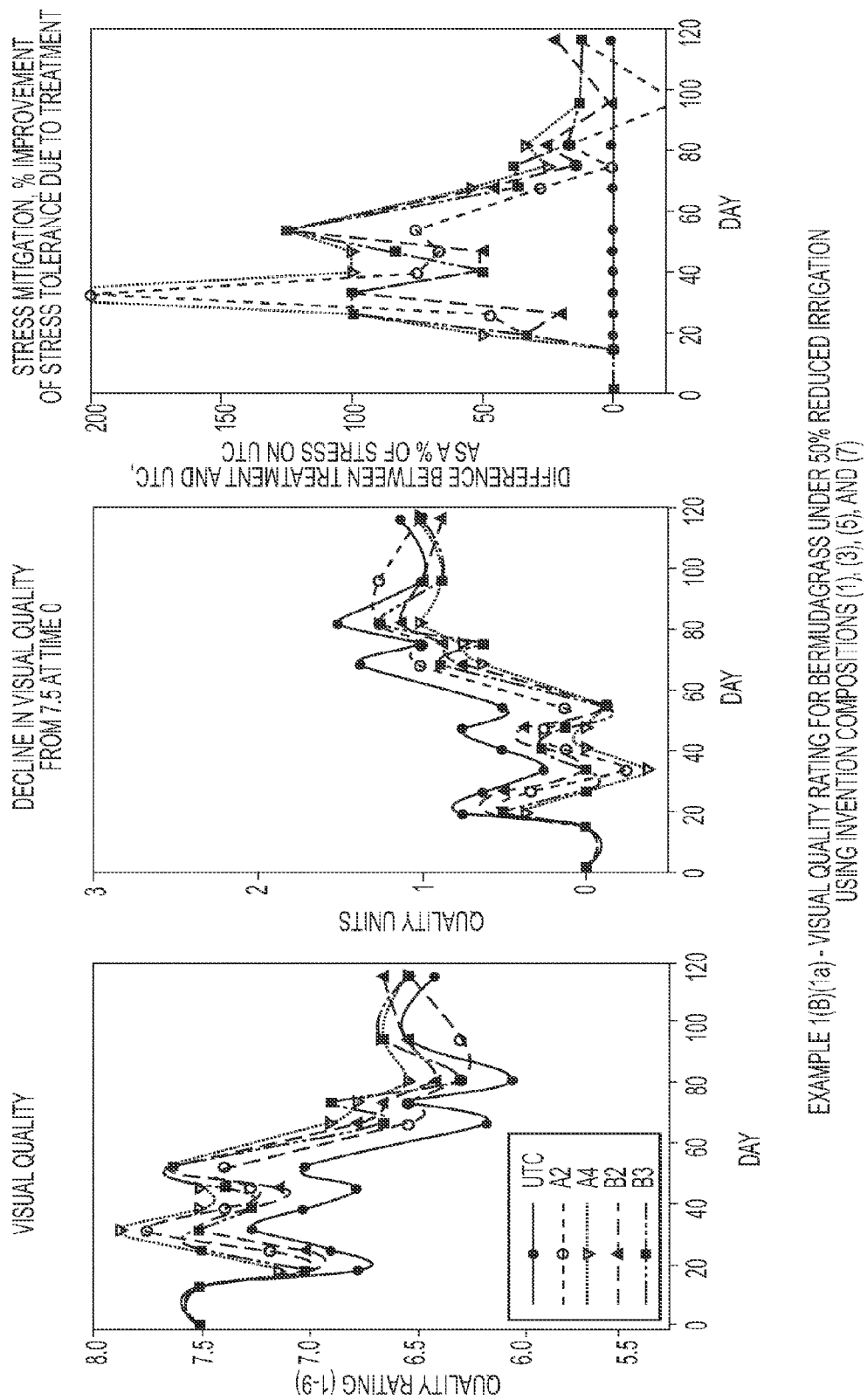
FIG. 9: shows results from a visual quality rating experiment.
Figure 10:
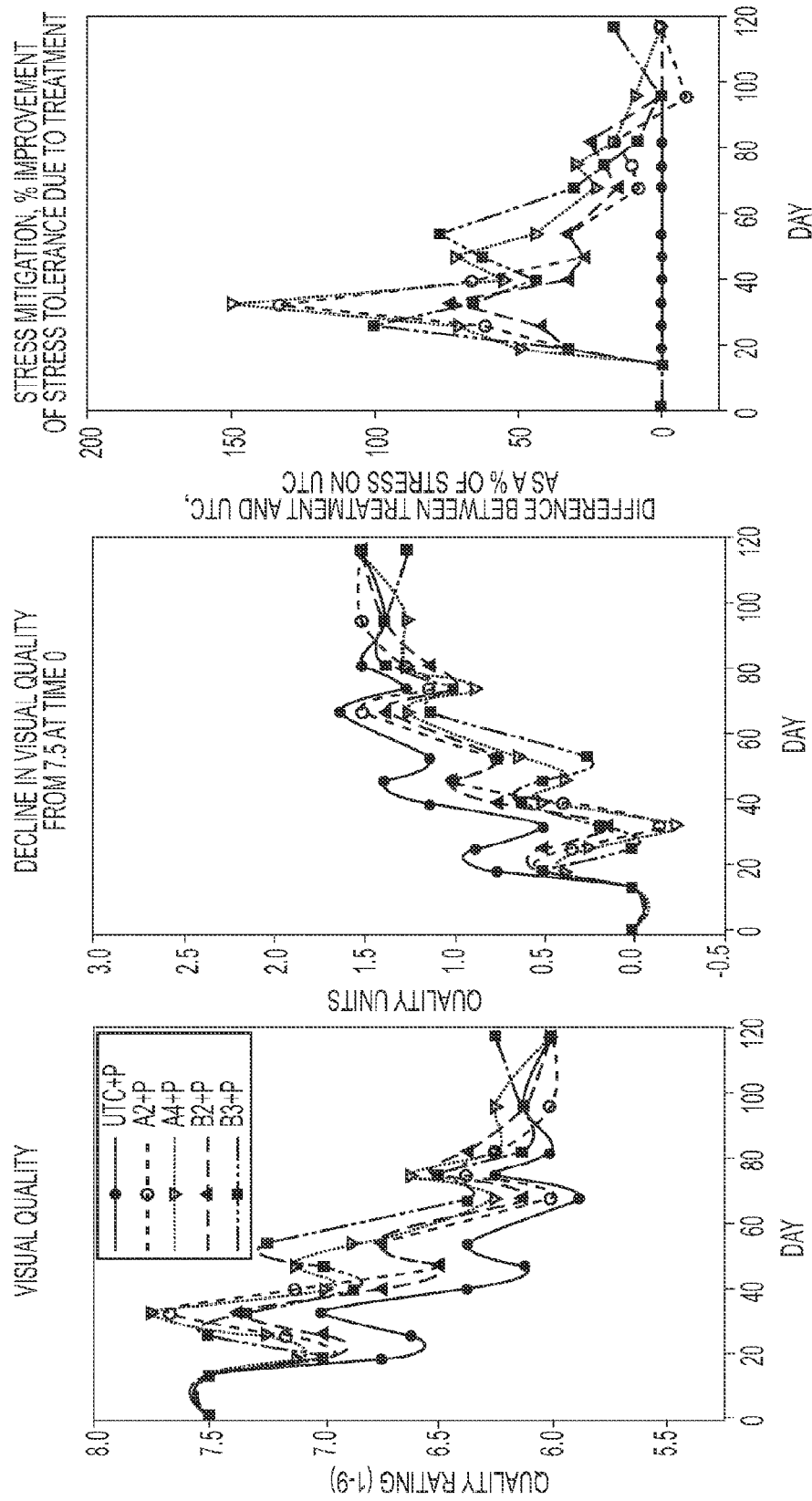
FIG. 10: shows results from a visual quality rating experiment.
Figure 11:
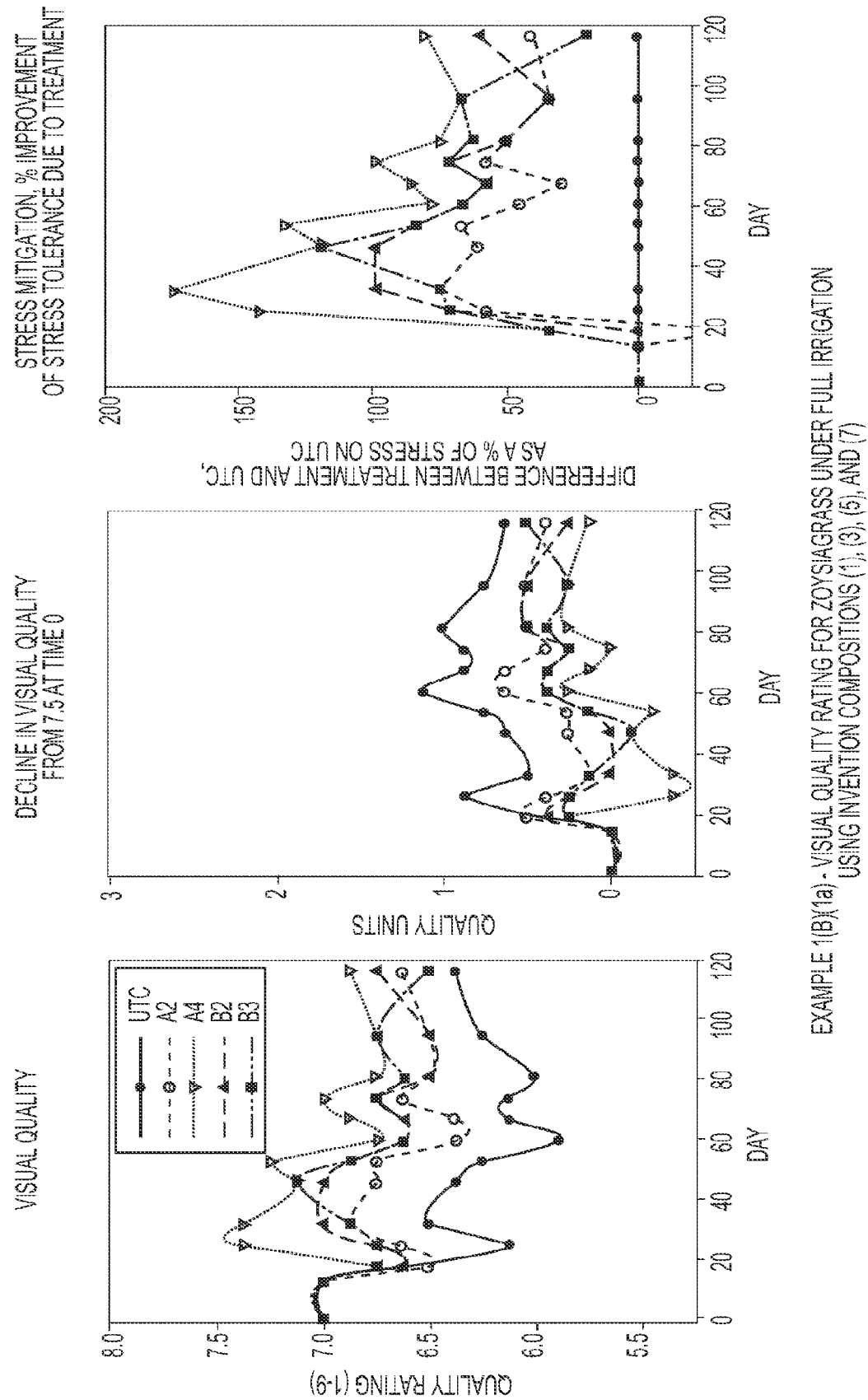
FIG. 11: shows results from a visual quality rating experiment.
Figure 12:
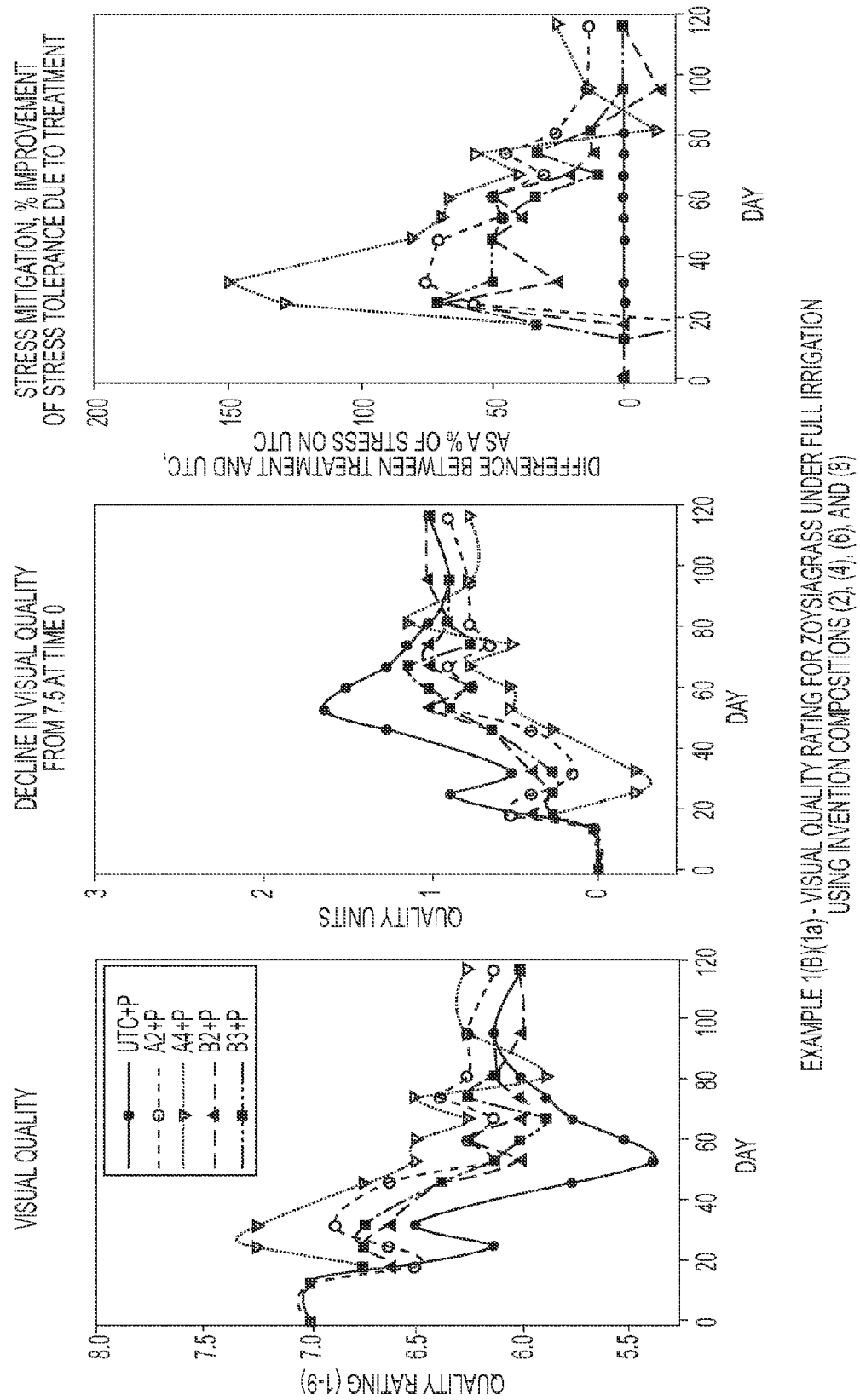
FIG. 12: shows results from a visual quality rating experiment.
Figure 13:
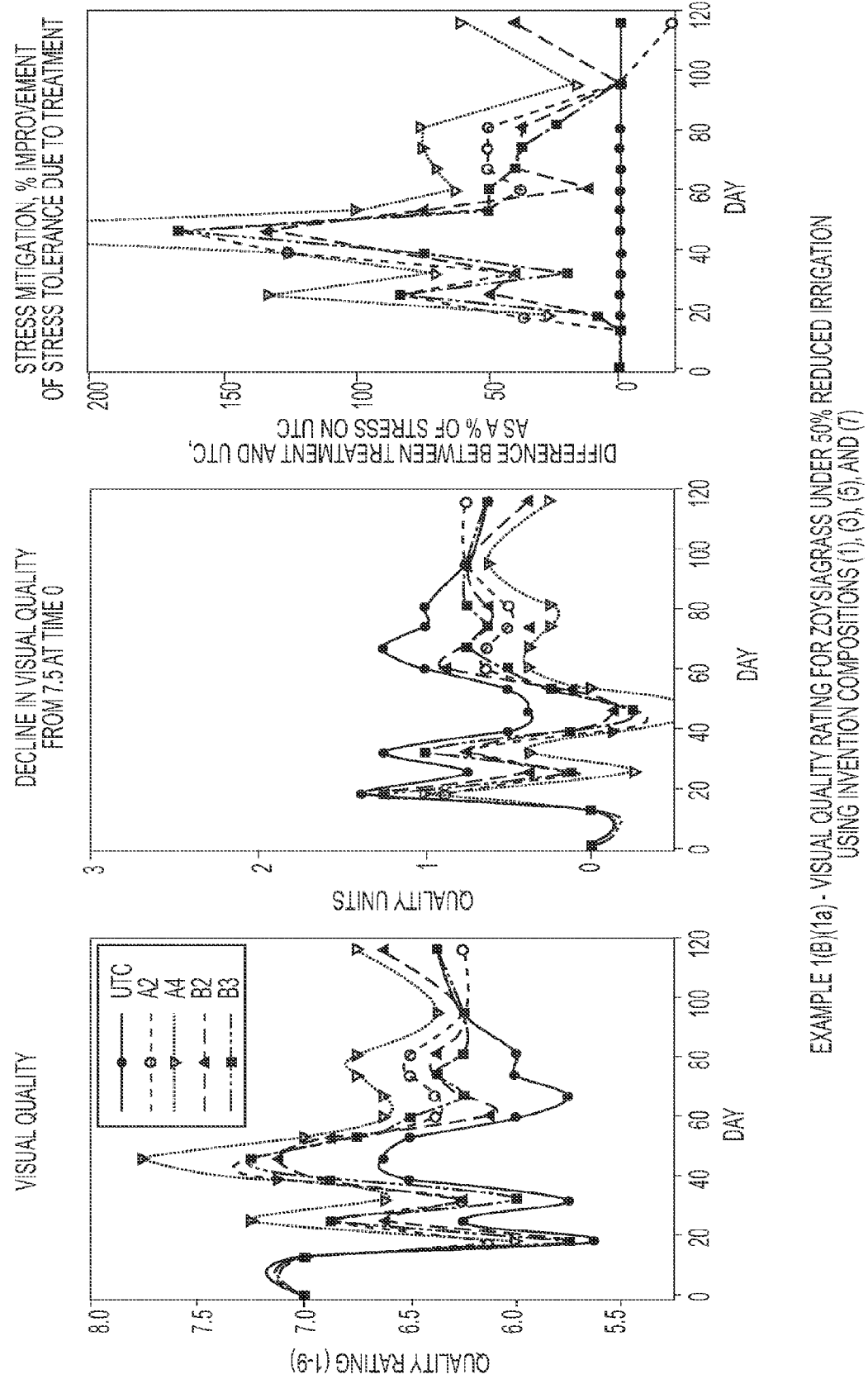
FIG. 13: shows results from a visual quality rating experiment.
Figure 14:
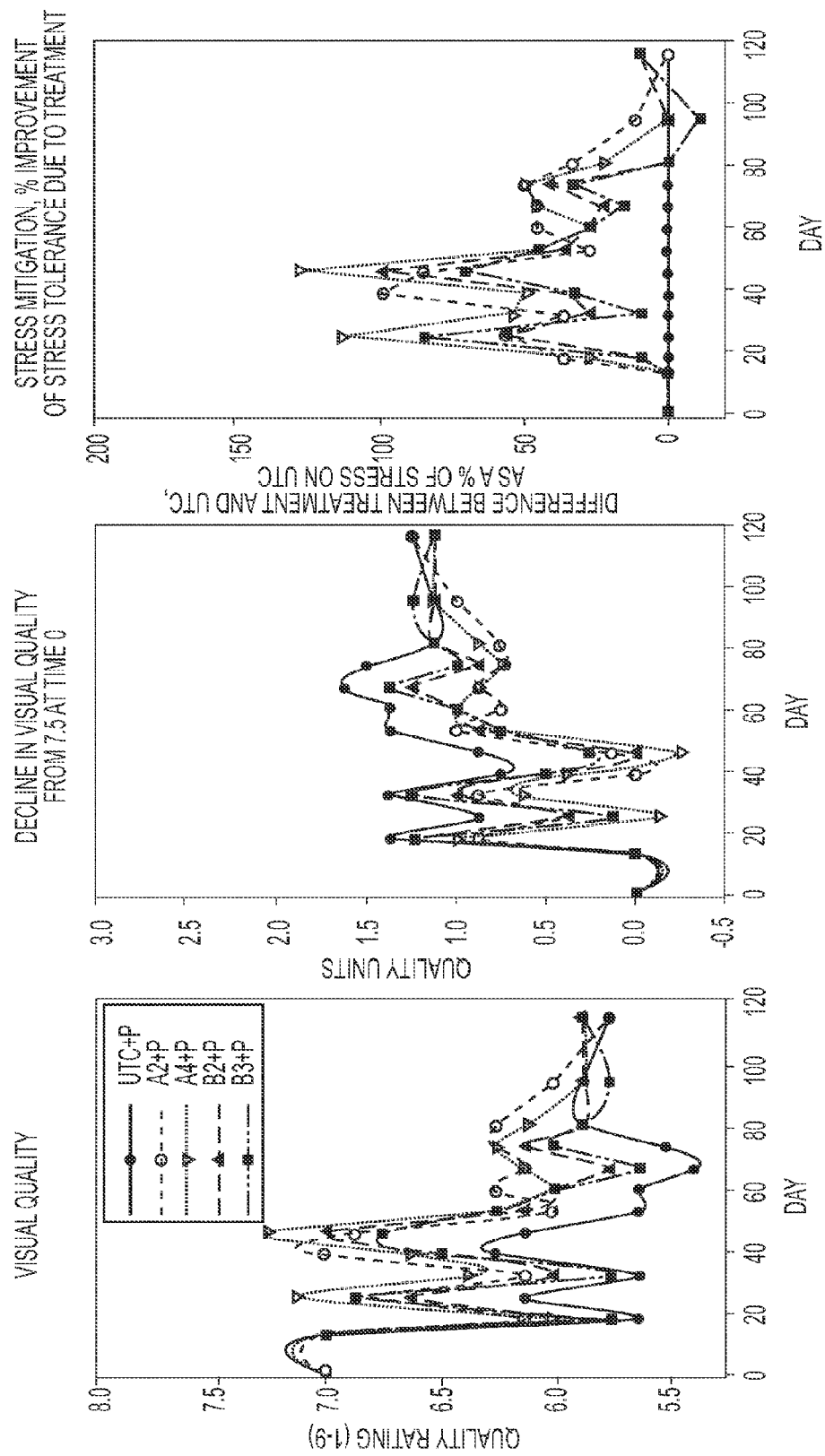
FIG. 14: shows results from a visual quality rating experiment.

A surprising and unexpected advantage of treating plants with compositions presented herein is that treated plants can be watered less and still exhibit maintained or improved plant quality, density, and natural color (greenness). By applying the present compositions, it has been surprisingly found that growing plants can tolerate reduced water irrigation, such as with temporary and sustained periods of drought when little or no water is available. Plants grown in a condition of reduced water irrigation, such as a reduction of from about 10% to about 50% in water irrigation, can exhibit improved green color, chlorophyll, shoot density, shoot fresh/dry weight, root fresh/dry weight, canopy temperature, and/or plot soil moisture after treatment with the present compositions.

When applied to grass and turfgrass in particular, another surprising and unexpected advantage of using compositions presented herein is that treated turfgrass can be mowed less and still exhibit maintained or improved quality, density, and natural color (greenness) in conditions of reduced water irrigation.

Methods and compositions presented herein can be used on varying types of plants, including turfgrasses, trees, ornamentals, and garden vegetables. Such plants are utilized in a wide array of landscapes, including plantations, urban forests, lawns, golf courses, sports fields, parks, and commercial areas, for example.

Application of the compositions herein can provide, for example, the following beneficial effects that are unexpected in conditions of reduced water irrigation: better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, and better storage stability and/or processability of the harvested products.

I. Compositions

The present compositions can be used to grow a plant under conditions of reduced water irrigation. In an embodiment, compositions comprise:
 (i) at least one antioxidant;
 (ii) at least one radiation manager; and
 one or more of
 (iii) at least one plant strengthener, or
 (iv) at least one plant growth regulator.

The compositions can also comprise, optionally, (v) at least one adjuvant, carrier, and/or dispersant.

In further embodiments, compositions comprise:
 (iii) at least one plant strengthener; and
 one or more of
 (i) at least one antioxidant, or
 (ii) at least one radiation manager comprising a polyoxyalkylene UV absorber.

The compositions may also comprise at least one plant growth regulator (iv) and/or at least one (v) adjuvant, carrier, and/or dispersant.

In further embodiments, the compositions disclosed herein are synergistic.

In some embodiments, the recited compositions specifically exclude non-recited components. That is, compositions with a negative proviso that non-recited components are not included in said compositions are covered by the disclosure.

I(A). Antioxidants

In certain embodiments, ccompositions presented herein comprise at least one antioxidant. Without being limited by any particular theory, an antioxidant includes any agent that facilitates photodynamic or reductive activation of molecular oxygen to produce reactive oxygen species, such as superoxide, hydrogen peroxide, and singlet oxygen. Antioxidants to be used in the present compositions further include enzymatic agents that produce reactive oxygen species.

Exemplary antioxidants that can be utilized in the present compositions include safeners, such as, for example, cyprosulfamide [CAS registry no. 221667-31-8], isoxadifen [CAS registry no. 209866-92-2], mefenpyr [CAS registry no. 135591-00-3], and derivatives thereof, including, for example, isoxadifen-ethyl [CAS registry no. 163520-33-0] and mefenpyr-ethyl [CAS registry no. 135590-91-9].

In other embodiments, antioxidants according to the disclosure include mefenpyr, trifloxystrobin, and sebacic acid.

Other exemplary safeners include, for example, benoxacor, cloquintocet, cyometrinil, dichlormid, dicyclonon, dietholate, fenchlorazole, fenclorim, flurazole, fluxofenim, furilazole, isoxadifen, jiecaowan, jiecaoxi, mefenpyr, mephenate, naphthalic anhydride, oxabetrinil, and derivatives thereof.

Exemplary antioxidants that can be utilized in the present compositions include vitamins, such as, for example, vitamin C (ascorbic acid), vitamin E (alpha-tocopherols and tocotrienols), glutathione, and derivatives thereof Exemplary antioxidants that can be utilized in the present compositions include strobilurins, such as, for example, fluoxastrobin, methoxyacrylate strobilurin acaricides (such as, methyl (EZ)-3-(fluoromethoxy)-2-[2-(3,5,6-trichloro-2-pyridyloxymethyl)phenyl]acrylate, fluacrypyrim, azoxystrobin, coumoxystrobin, enestroburin, methyl (2E)-2-{2-[(3,4-dimethyl-2-oxo-2H-chromen-7-yl)oxymethyl]phenyl}-3-methoxyacrylate (CAS registry no. 850881-30-0), picoxystrobin, pyraoxystrobin, and derivatives thereof), methoxycarbanilate strobilurins (such as methyl N-methoxy-2-(3,5,6-trichloro-2-pyridyloxymethyl)carbanilate (CAS registry no. 902760-40-1), pyraclostrobin, pyrametostrobin, and derivatives thereof), methoxyiminoacetamide strobilurins (such as dimoxystrobin, metominostrobin, orysastrobin, (2E)-2-(2-{(E)-[(2E)-3-(2,6-dichlorophenyl)-1-methylprop-2-enylidene]aminooxymethyl}phenyl)-2-(methoxyimino)-N-methylacetamide (CAS registry no. 366815-39-6), and derivatives thereof), and methoxyiminoacetate strobilurins (such as kresoxim-methyl (methyl (E)-methoxyimino[α-(o-tolyloxy)-o-tolyl] acetate), trifloxystrobin, and derivatives thereof).

Exemplary antioxidants also include mono- and/or di-acyl urea containing derivatives, such as, for example, benzthiazuron, cumyluron, cycluron, dichloralurea, diflufenzopyr, isonoruron, isouron, methabenzthiazuron, monisouron, noruron, and derivatives thereof. Exemplary mono- and di-acyl urea containing derivatives include phenylureas, such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron, thidiazuron, and derivatives thereof. Exemplary mono- and di-acyl urea containing derivatives include sulfonylureas, such as pyrimidinylsulfonylureas, which include amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, methiopyrisulfuron, monosulfuron, nicosulfuron, orthosulfamuron, oxasulfuron, primisulfuron, propyrisulfuron, pyrazosulfuron, rimsulfuron, sulfometuron, sulfosulfuron, trifloxysulfuron, zuomihuanglong, and derivatives thereof. Other exemplary sulfonylureas include triazinylsulfonylureas, such as chlorsulfuron, cinosulfuron, ethametsulfuron, iodosulfuron, iofensulfuron, metsulfuron, prosulfuron, thifensulfuron, triasulfuron, tribenuron, triflusulfuron, tritosulfuron, and derivatives thereof. Exemplary mono- and di-acyl urea containing derivatives include thiadiazolylureas, such as buthiuron, ethidimuron, tebuthiuron, thiazafluron, thidiazuron, and derivatives thereof.

Exemplary di-acyl urea containing antioxidants also include N', N'-di-substituted ureas, such as those corresponding to formula (I):

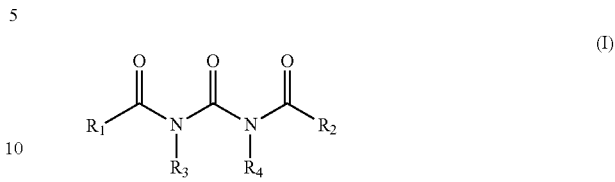

where $R_1$, $R_2$, $R_3$, and $R_4$ are the same or different and are selected from the group consisting of hydrogen, substituted and unsubstituted alkyl, allyl, vinyl and alkoxyl groups having from one to six carbon atoms, substituted and unsubstituted phenyl groups, and halides. In a particular embodiment, $R_1$ and $R_2$ are selected from the group consisting of hydrogen and alkyl groups having from one to three carbon atoms. N', N', di-substituted ureas are described, for example, in U.S. Pat. Nos. 6,040,273, 6,448,440, 6,710,085, and 7,022,648, the entire disclosure of all of which are incorporated herein by reference.

A particular exemplary N', N'-di-substituted acyl urea that can be included in compositions presented herein is N', N'-diformyl urea, which has a structure according to formula (Ia):

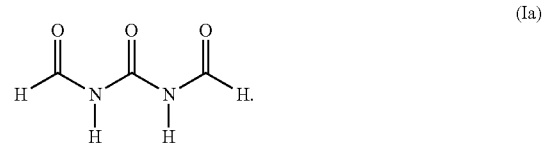

Mono- and di-substituted ureas to be included in compositions herein can be the reaction product of a carboxylic acid and a urea. In such embodiments, the urea reactant can be unsubstituted so that $R_3$ and $R_4$ in the reaction product are hydrogen. In a particular embodiment, formic acid is reacted with urea in a molar ratio of about 2:1 to produce N,N'-diformylurea. The reaction can be conducted at temperatures between about 10° C. and about 140° C., such as at room temperature.

In another embodiment, where a di-substituted urea is included in the present compositions as a reaction product (i.e., di-substitute urea is produced in situ), carboxylic acids having the formula RCOOH may be used as a reactant in which R is selected from the group consisting of hydrogen, substituted and unsubstituted alkyl, allyl vinyl, and alkoxyl groups having from 1-6 carbon atoms, substituted and unsubstituted phenyl group, and halides. Exemplary carboxylic acid reactants include formic acid, acetic acid, propionic acid, butyric acid, valeric acid, caproic acid, heptanoic acid, and citric acid. Preferably R is selected from the group consisting of hydrogen and unsubstituted alkyl groups having from 1-3 carbon atoms. The presently most preferred acids are formic or acetic acid. These carboxylic acids are reacted with a substituted or unsubstituted urea having the formula $(NHR')_2CO$ where each R' is the same or different and is selected from the group consisting of hydrogen, substituted and unsubstituted alkyl groups having from 1-6 carbon atoms, substituted and unsubstituted alkoxyl groups having from 1-6 carbon atoms, substituted and unsubstituted phenyl groups and the halides. Unsubstituted urea is a preferred reactant. Exemplary methods of preparing N', N', di-substituted ureas are described, for example, in U.S. Pat. Nos. 6,040,273, and 6,448,440, the entire disclosure of all of which have been previously incorporated by reference. Other mono- and di-substituted ureas that can be included in the present compositions include those described in U.S. Pat. Nos. 2,430,591, 3,137,697, 3,234,000, 3,420,687, 4,239,526, 4,437,894, and 4,466,893, the entire disclosure of which is incorporated herein by reference.

Exemplary antioxidants that can be included in the present compositions are (1) molecules having one or more phosphorus connected to one or more urea-like functional groups, and/or (2) molecules that release phosphine, phosphorous, and/or urea in situ. These exemplary phosphorous containing urea derivatives can be cyclical, such as those shown below in formulas (II), (III), and (IV) as described in *A Journal of Chemical Sciences,* 48(7), 860-6 (1993), the entire disclosure of which is incorporated herein by reference.

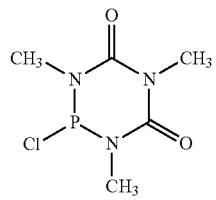

(II)

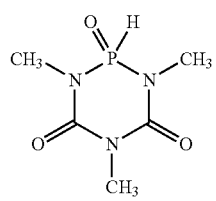

(III)

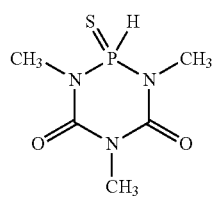

(IV)

Other exemplary phosphorous containing urea derivatives can be acyclical, such as with phosphonic diamide (CAS registry no. 6706-48-5), the structure of which is shown below in formula (V) and described in Aminov, S. N. et. al., "Synthesis and physicochemical study of alkylphosphonic acid surfactant derivatives", *Tr.-Mezhdunar. Kongr. Poverkhn.-Akt. Veshchestvam,* 7(1): 210-16 (1977), meeting date 1976, the entire disclosure of which is incorporated herein by reference.

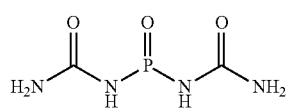

(V)

Other exemplary acyclic phosphorous containing urea derivatives include diureido-phosphine (CAS registry no. 6706-47-4), the structure of which is shown below in formula (VI)

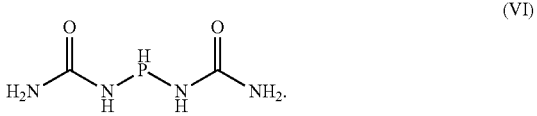

(VI)

In an embodiment, compositions presented herein comprise at least one (ii) antioxidant in an amount effective to achieve plant growth under a condition of reduced water irrigation. In an embodiment, compositions presented herein comprise at least one (ii) antioxidant at concentrations ranging from about 1% to about 10% (w/w) such as, for instance, from about 3% to about 8% (w/w), from about 4% to about 7% (w/w), or from about 5% to about 6% (w/w). In an embodiment, compositions presented herein comprise from about 1.2% to about 4% (w/w) N, N-diformyl urea.

I(B). Radiation Manager

In certain embodiments, compositions presented herein comprise at least one radiation manager. As used herein, the term "radiation manager" refers to any agent that facilitates passage of UV light and/or high energy visible blue light.

Exemplary radiation managers in the present compositions include at least one (i) colorant that screens UV and high energy visible blue light, and/or at least one (iii) salt, oxide, and formats of higher atomic weight metals, such as zinc oxide, titanium oxide, magnesium carbonate, and calcium carbonate, for example In some embodiments, exemplary radiation managers include polyoxyalkylene UV absorbers.

As used herein, the term "higher atomic weight metal" refers to metals with an atomic weight above 20 a.m.u. Exemplary higher atomic weight metals include potassium, calcium, scandium, titanium, vanadium, chromium, manganese, iron, cobalt, nickel, gallium, germanium, and selenium.

Exemplary colorant that may be used herein include dyes and/or pigments that screen UV and high energy visible blue light, such as heteropolyaromatic dyes, such as methylene blue, kermesic acid (carminic acid), indigo, punicin (tyrian purple), crocetin, beta carotene, and derivatives thereof. Pigments that may be used include pigment blue 15:4, pigment blue 15:3, pigment blue 15:2, pigment blue 15:1, pigment blue 80, pigment yellow 1, pigment yellow 13, pigment green 36, pigment green 7, pigment white 6.

Exemplary oxides that can be used include those that can be micronized or presented as nanoparticles, such as with titanium oxide. Exemplary oxides include mixtures of oxides, such as titanium and zinc oxide, as provided, for example, under the tradename Turfscreen™.

Exemplary pigments include phthalocyanines. See, for example, DE 2,511,077, and JP 03/221576, the contents of both of which are incorporated in their entirety herein. Phthalocyanines used in the present compositions can be metal-free or metal-containing. The metals of metal-containing phthalocyanines can be transition metals, such as copper, silver, gold, zinc, cadmium, mercury, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, and platinum. Copper, nickel, cobalt, iron, and zinc phthalocyanines are preferred, with copper phthalocyanines being particularly preferred.

Substituted phthalocyanines can be used in the present compositions and include, for example, phthalocyanines substituted from 1 to 4 times on each isoindole group independently. Examples of suitable substituents for the isoindole groups of phthalocyanines include but are not limited to halogen, unsubstituted or substituted lower alkyl, lower alkoxy, alkylamino, alkylthio, ammonium, sulfonato, sulfonato alkyl, sulfate, phosphate, phosphonate, and carboxylate. The ionic or ionizable substituents can have as counterions the alkali metals, preferably lithium, sodium, or potassium, the alkaline earth metals, such as beryllium, magnesium, calcium, strontium, or barium, or various ammonium ions. The term "lower alkyl" and "lower alkoxy" are generally meant alkyl groups of from 1 to 6 carbon atoms and alkoxy groups of from 1 to 6 carbon atoms. Exemplary substituted phthalocyanines include copper phthalocyanines that are multiply substituted with chlorine atoms.

Phthalocyanines are commercially available and include, but are not limited to, those available under the names Pigment Blue 16, Vat Blue 29, Pigment Blue 15, Heliogen Green GG, Ingrain Blue 14, Ingrain Blue 5, Ingrain Blue 1, Pigment Green 37, and Pigment Green 7. In an embodiment, the present compositions comprise a polychlorinated copper phthalocyanine, also referred to as Pigment Green 7.

In an embodiment, compositions presented herein comprise at least one radiation manager (ii) in an amount effective to achieve plant growth under a condition of reduced water irrigation. In an embodiment, compositions presented herein comprise at least one radiation manager (ii) at concentrations ranging from about 5 active grams to about 500 active gram per total liter of composition, for instance, from about 10 active grams to about 250 active gram per total liter of composition, from about 20 active grams to about 150 active gram per total liter of composition, from about 50 active grams to about 100 active gram per total liter of composition, or from about 60 active grams to about 80 active gram per total liter of composition.

In an embodiment, compositions presented herein comprise from about 2.5% to about 3.5% (w/w) phthalocyanine green pigment, such as pigment Green 7.

I(C). Plant Strengthener

Compositions presented herein may comprise at least one plant strengthener. Without being limited by any particular theory, a plant strengthener includes any agent that promotes healthier, stronger, better-looking plants or any agent that reinforces a plant's natural protective mechanisms.

Exemplary plant strengtheners in the present compositions include, for example, phosphites, phosphonates, and phosphorous containing compounds and salts thereof, such as phosphorous acid. Phosphites that can be utilized include, for example, ureido- and urea-phosphites. Phosphonates that can be utilized include phosphonate esters, such as aluminium tris-O-ethylphosphonate or fosetyl-Al, which include those sold under the tradenames Aliette®, Mikal®, Profiler®, R6 Albis®, R6 Trevi®, Rhodax®, and Valiant®. In an embodiment, phosphorous acid, including those sold under the tradename FoliRFos©, is included in the present compositions.

Exemplary plant strengtheners in the present compositions also include phosphorous acid, monoalkyl esters of phosphorous acid, or salts thereof. Examples of such compounds are (i) compounds of the formula $[HP(OR)O_2)^-]_n M^{n+}$ in which R is a $C_2$-$C_4$ alkyl, M is an alkali metal, alkaline earth, or aluminum atom, and n is an integer of from 1 to 3 equal to the valence of M, or (ii) phosphorous acid or alkaline earth metal salts thereof.

Exemplary plant strengtheners in the present compositions also include inducers of systemic resistance. An inducer of systemic resistance is any agent that induces a plant to systemically express a broad spectrum and long lasting disease resistance that is efficient against fungi, bacteria, and/or viruses. Without being limited to any particular theory, it is believed that systemic resistance is elicited by a local infection and is mediated via a salicylic dependent signaling cascade. Inducers of systemic resistance are described, for example, in Heil, M. et al., "Induced Systemic Resistance (ISR) Against Pathogens in the Context of Induced Plant Defences, *Annals of Botany*, 89(5): 503-512 (2001), the disclosure of which is incorporated herein by reference.

Inducers can be biological and/or naturally occurring inducers, such as *Myrothecium verrucaria, Burholderia cepacia, Bacillus chitonosporus, Paecilomyces lilacinus, Bacillus amyloliquefaciens, Bacillus firmus, Bacillus subtilis*, and *Bacillus pumulis*. Other species in the *Bacillus* genus that can be included in the present compositions are *Bacillus argri, Bacillus aizawai, Bacillus albolactis, Bacillus amyloliquefaciens, Bacillus cereus* (e.g., strain BP01), *Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus* spp., *Bacillus subtilis, Bacillus thurngiensis*, and *Bacillus unifagellatus*.

Exemplary plant strengtheners in the present compositions include inducers of systemic acquired resistance. An inducer of systemic acquired resistance is any agent that induces a "whole-plant" resistance response following an earlier localized exposure to a pathogen. Without being limited to any particular theory, it is believed that systemic acquired resistance is analogous to the innate immune system found in animals, and is one important way in which plants resist disease, as well as recover from disease once formed. Systemic acquired resistance is described, for example, in Ryals et al., "Systemic Acquired Resistance", *The Plant Cell*, 8:1809-1819 (1996), the disclosure of which is incorporated herein by reference.

Exemplary inducers of systemic acquired resistance include acibenzolar and derivatives thereof, such as acibenzolar-S-methyl. Other exemplary inducers include chitosan and harpin protein, such as the harpin protein of *Erwinia amylovora* as described in U.S. Pat. No. 5,977,060, the disclosure of which is incorporated herein by reference and laminarin.

Exemplary plant strengtheners in the present compositions also include aviglycine, N-(phenylmethyl)-1H-purin-6-amine, epocholeone, mepiquat chloride, prohexadione calcium, prohydrojasmon, sodium nitrophenolate and trinexapac-ethyl, aprobenazole, *Reynoutria sachalinensis* extract (reysa).

Other exemplary plant strengtheners that can be included in the present compositions are plant hormones. Hormones may be synthetic or natural or any combination thereof. Hormones may be produced via recombinant engineering, the amino acid sequence of which can be identical or similar to a plant hormone.

Exemplary plant hormones include native and synthetic auxins, such as indole, indole-3-butyric acid (CAS registry no. 133-32-4), dicamba (CAS registry no. 1918-00-9), and derivatives thereof. Other exemplary auxins include 4-chlorophenoxyacetic acid, 2,4-D, anti-auxins, such as (2,4-dichlorophenoxy)acetic acid, 2,4,6-trichlorobenzoic acid or 2-(2,4-dichlorophenoxy) proprionic acid, 4-(2,4-dichlorophenoxy)butyric acid, tris[2-(2,4-dichlorophenoxy)ethyl] phosphate, dichlorprop, fenoprop, 1H-indol-3-ylacetic acid, 4-(1H-indol-3-yl)butyric acid, naphthaleneacetamide, naphthalene acetic acid, α-naphthalene acetic acid, 1-naphthol, naphthoxyacetic acids, potassium naphthenate, sodium naphthenate, (2,4,5-trichloro-phenoxy)acetic acid, and derivatives thereof.

Exemplary plant hormones include gibberellins, such as, for example, gibberellin A1, A3 (gibberellic acid), and gibberellin A4 and A7. Gibberellins are known, and described, for example, in R. Wegler "Chemie der Pflanzenschutz- and Schadlingsbekampfungsmittel", *Chemistry of Crop Protection Compositions and Pesticides*, vol. 2, Springer Verlag, 1970, p. 401-412, the disclosure of which is incorporated herein by reference Exemplary plant hormones also include cytokinins, such as, for example, zeatin, kinetin, thidiazuron or benzylaminopurine, abscisic acid, ABA inhibitors such as aminotriazole, ethylene, ethylene-substitutes such as 1-propene, competitive inhibitors of ethylene such as 1-butene, 1-pentene, 1-hexane, 1-octene, 1-decene, 1-dodecene, or ethylene blockers such as norbornadiene.

In an embodiment, compositions presented herein comprise at least one plant strengthener (iii) in an amount effective to achieve plant growth under a condition of reduced water irrigation. In an embodiment, compositions presented herein comprise at least one plant strengthener (iii) at concentrations ranging from about 5 active grams to about 500 active gram per total liter of composition, for instance, from about 10 active grams to about 250 active gram per total liter of composition, from about 20 active grams to about 150 active gram per total liter of composition, from about 50 active grams to about 100 active gram per total liter of composition, or from about 60 active grams to about 80 active gram per total liter of composition.

In an embodiment, compositions presented herein comprise from about 16% to about 18% (w/w) phosphorous acid.

I(D). Plant Growth Regulator

Compositions presented herein may comprise at least one plant growth regulator. As used herein, the term "plant growth regulator" refers to any agent that accelerates or retards the rate of growth or maturation or otherwise alters the behavior of a plant. Plant growth regulators include plant nutrients, plant inoculants, and soil amendments, for example.

Plant growth regulators that can be included in the present compositions include, for example, Type I and/or Type II plant growth retardants (PGRs). PGRs are separated into two groups, Type I and Type II, based on their method of growth inhibition or suppression. While not wishing to be bound by any particular theory, it is believed that type I PGRs are primarily absorbed through the foliage and inhibit cell division and differentiation in meristematic regions. They are inhibitors of vegetative growth and interfere with seedhead development. Their growth inhibition is rapid, occurring within 4 to 10 days, and lasts 3 to 4 weeks, depending on application rate. Mefluidide, chlorflurenol, and maleic hydrazide are examples of Type I PGRs that inhibit mitosis in growth and development. Other Type I PGRs inhibit plant growth and development through interruption of amino acid or organic acid biosynthesis. Other examples of Type I PGRs that can be included in the present compositions are glyphosate, imidazolinones, sulfonylureas, sethoxydim, and fluazifop.

While not wishing to be bound by any particular theory, it is believed that type II PGRs are generally root absorbed and suppress growth through interference of gibberellic acid bio-synthesis, a hormone responsible for cell elongation. Type II PGRs are slower in growth suppression response, but their duration is usually from 4 to 7 weeks, again, depending on application rate. Type II PGRs have little effect on seedhead development and result in miniature plants. Paclobutrazol, flurprimidol, trinexapac-ethyl, and fenarimol are examples of type II PGRs that can be included in the present compositions.

Plant growth regulators that can be included in the present compositions include, for example, other inhibitors of gibberellin biosynthesis. While not wishing to be bound by any particular categorization, there are at least four different types of such inhibitors known, all of which can be included in the present compositions. One type of inhibitors of gibberellin biosynthesis are onium compounds, such as chlormequat chloride, mepiquat chloride, chlorphonium, and AMO-1618, which block the cyclases copalyl-diphosphate synthase and ent-kaurene synthase involved in the early steps of gibberellin metabolism. A second type of inhibitors of gibberellin biosynthesis are compounds with an N-containing heterocycle, e.g. ancymidol, flurprimidol, tetcyclacis, paclobutrazol, uniconazole-P, and inabenfide. These inhibitors block cytochrome P450-dependent monooxygenases, thereby inhibiting oxidation of ent-kaurene into ent-kaurenoic acid. A third type of inhibitors of gibberellin biosynthesis are structural mimics of 2-oxoglutaric acid, which is the co-substrate of dioxygenases that catalyze late steps of gibberellin formation. These structural mimics include cylcyclohexanediones, e.g. prohexadione-Ca and trinexapac-ethyl and daminozide, which block 313-hydroxylation, thereby inhibiting the formation of highly active gibberellin from inactive precursors. A fourth type of inhibitors of gibberellin biosynthesis are 16,17-Dihydro-$GA_5$ and related structures. This type of inhibitor most likely mimicking the gibberlin precursor substrate of the dioxygenase that catalyzes late steps of gibberellin formation.

Other plant growth regulators that can be included in the present compositions include, for example, compounds that inhibit sterol biosynthesis in plants. Exemplary inhibitors of sterol biosynthesis include 2'-isopropyl-4'-(trimethylammonium chloride)-5-methylphenylpiperidine carboxylate, β-chloroethyltrimethylammonium chloride, and tributyl-2,4-dichlorobenzylphosphonium chloride. Other inhibitors of sterol biosynthesis in plants that can be included in the present compositions are described, for example, in Burden, R. et al., "Inhibitors of sterol biosynthesis and growth in plants and fungi", *Phytochemistry*, 28(7): 1791-1804 (1989), the disclosure of which is incorporated herein by reference.

In an embodiment, compositions presented herein comprise at least one plant growth regulator (iv) in an amount effective to achieve plant growth under a condition of reduced water irrigation. In an embodiment, compositions presented herein comprise at least one plant growth regulator (iv) at concentrations ranging from about 5 active grams to about 500 active gram per total liter of composition, for instance, from about 10 active grams to about 250 active gram per total liter of composition, from about 20 active grams to about 150 active gram per total liter of composition, from about 50 active grams to about 100 active gram per total liter of composition, or from about 60 active grams to about 80 active gram per total liter of composition.

In an embodiment, compositions presented herein comprise about 1.0 lb active ingredient per gallon of trinexapac-ethyl.

I(E). Adjuvants, Carriers, Dispersants

Compositions presented herein can optionally comprise adjuvants, additives, carriers, dispersants, and/or formulation auxiliaries conventionally used in plant formulations.

The term "carrier" as used herein refers to an organic or inorganic material, which can be natural or synthetic, and which can be associated with the active components of the composition and facilitate its application to the soil, plant, or plant part to be treated. This carrier is generally inert and should be agriculturally acceptable, especially on the contemplated or treated turfgrass. The carrier can be solid (e.g., clay, silicates, silica, resins, wax, fertilizers, and the like) or liquid (e.g., water, alcohols, ketones, oil solvents, saturated or unsaturated hydrocarbons, chlorinated hydrocarbons, liquefied petroleum gas, and the like).

Among the many optional additives suitable for use in the present compositions include surfactants and other ingredients, such as dispersants, stickers, antifoam agents, antifreezing agents, dyestuffs, thickeners, adhesives, protective colloids, penetrating agents, stabilizing agents, sequestering agents, antiflocculating agents, corrosion inhibitors, pigments (other than those contemplated as an active ingredient for purposes of the invention), and polymers.

More generally, the compositions of the invention can include all kinds of solid or liquid additives which are known in the art of crop protection and horticultural pest control treatments.

The surfactants can be of the emulsifying or wetting type and can be ionic or non-ionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols. When the spraying vehicle is water, the use of at least one surfactant is generally present if the active ingredients are not water-soluble.

Dusting powders, granulates, solution, emulsifiable concentrates, emulsions, suspended concentrates and aerosols are also contemplated within the invention. Compositions can be formulated as a wettable powder and can be prepared in such a way that they contain active components in addition to a solid support, a wetting agent, a dispersant, and one or more stabilizers and/or other additives, such as penetration agents, adhesives or anti-clumping agents, or colorants. Wettable powders (sprayable powders) are products which are uniformly dispersible in water and which, besides the active substance, also comprise ionic or non-ionic surfactants (wetters, dispersants), for example polyoxyethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material. The compositions according to the invention can contain other ingredients, for example protective colloids, adhesives or thickeners, thixotropic agents, stabilizers or sequestrants, as well as other active materials known to have pesticidal properties, especially certain fungicides, acaricides, and insecticides.

The individual formulation types are known in principle and are described, for example, in: Winnacker-Kuchler "Chemische Technologie" [Chemical engineering], Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

Formulation auxiliaries, such as inert materials, surfactants, solvents and other additives are also known and are described, for example, in Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridegewood N.J.; Sisley and Wood, "Encyclopedia of Surface Active Agents", Chem. Publ. Co. Inc., N.Y. 1964; Schonfeldt, "Grenzflachenaktive Athylenoxidaddukte" *Surface-active ethylene oxide adducts*, Wiss. Verlagsgesellschaft, Stuttgart 1976, Winnacker-Kuchler, "Chemische Technologie", Volume 7, C. Hauser Verlag Munich, 4th Edition 1986.

Based on these formulations, combinations with pesticidally active substances, such as herbicides, fungicides or insecticides, fertilizers and/or growth regulators, may also be prepared, for example in the form of a readymix or a tank mix.

The present compositions can be formulated as an emulsifiable concentrate, such as, for example, concentrates prepared by dissolving the active substance in an organic solvent, for example butanol, cyclohexanone, dimethylformamide, xylene or else higher-boiling aromatic or hydrocarbons with addition of one or more ionic or non-ionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

The present compositions can be formulated as a dust, such as those, for example, that are obtained by grinding the active substances with finely divided solid materials, for example talc, natural clays such as kaolin, bentonite and pyrophyllite, or diatomaceous earth.

The present compositions can be formulated as granules, such as those, for example, prepared either by spraying the active substances onto adsorptive, granulated inert material or by applying active substance concentrates to the surface of carriers such as sand, kaolites or granulated inert material with the aid of binders, for example polyvinyl alcohol, sodium polyacrylate or else mineral oils. Suitable active substances may also be granulated in the manner conventionally used for the production of fertilizer granules, if desired in a mixture with fertilizers. As a rule, water-dispersible granules are prepared by processes such as spray drying, fluidized-bed granulation, disk granulation, mixing with high-speed mixers and extrusion without solid inert material.

Generally, the agrochemical preparations comprise 0.1 to 99 percent by weight, in particular 2 to 95% by weight, of active substances of the types A and/or B, the following concentrations being customary, depending on the type of formulation. The active substance concentration in wettable powders is, for example, approximately 10 to 95% by weight, the remainder to 100% by weight being composed of customary formulation constituents. In the case of emulsifiable concentrates, the active substance concentration may amount to, for example, 5 to 80% by weight. Sprayable concentrates comprise from about 2% to about 50% by weight of active substances. Formulations in the form of dusts comprise, in most cases, 5 to 20% by weight of active substance, sprayable solutions approximately 0.2 to 25% by weight of active substance.

In the case of granules such as dispersible granules, the active substance content depends partly on whether the active compound is present in liquid or solid form and on which granulation auxiliaries and fillers are being used. Generally, the content amounts to between 10 and 90% by weight in the case of the water-dispersible granules.

In addition, the abovementioned active substance formulations may comprise, if appropriate, the conventional adhesives, wetters, dispersants, emulsifiers, preservatives, antifreeze agents, solvents, fillers, colors, carriers, antifoams, evaporation inhibitors, pH regulators or viscosity regulators.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further prior to use with other inert substances.

Depending on their particular physical and/or chemical properties, the active compound combinations according to the invention can be converted into the customary formulations, such as solutions, emulsions, suspensions, powders, dusts, foams, pastes, soluble powders, granules, aerosols, suspoemulsion concentrates, natural and synthetic materials impregnated with active compound and microencapsulations in polymeric substances and in coating compositions for seeds, and ULV cool and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

The present compositions can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, painting, spreading-on, and as a powder for dry seed treatment, a solution for seed treatment, a water-soluble powder for seed treatment, a water-soluble powder for slurry treatment, or by encrusting etc.

II. Composition Formulations

The present compositions can be formulated as a mixture of the active components, if appropriate together with other active substances, additives and/or conventional formulation auxiliaries, which are then applied in the customary manner after dilution with water, but also as so-called tank mixes by jointly diluting the separately formulated, or partially separately formulated, components with water.

The present compositions can be formulated in different ways, depending on the biological and/or chemico-physical parameters which prevail. The following are examples of general possibilities for formulations: wettable powders (WP), emulsifiable concentrates (EC), aqueous solutions (SL), suspension concentrates (SC), emulsions (EW) such as oil-in-water and water-in-oil emulsions; sprayable solutions or emulsions, oil- or water-based dispersions, suspoemulsions, dusts (DP), seed-dressing materials, granules for soil application or for broadcasting, or water dispersible granules (WG), ULV formulations, microcapsules or waxes.

III. Synergistic Compositions

In an embodiment, the present compositions impart, facilitate, and/or result in synergistic effects. The synergistic effects are observed when the active components are applied together, but can also be observed upon split application (splitting). Another possibility is to apply the active components in several portions (sequential application), for example after pre-emergence applications, followed by post-emergence applications or after early post-emergence applications, followed by applications at medium or late post-emergence. In an embodiment, the active components of the composition in question are simultaneously applied, if appropriate, in several portions. However, a staggered application of the individual active components is also possible and may be advantageous in individual cases. Other crop protection agents such as fungicides, insecticides, acaricides and the like, and/or different auxiliaries, adjuvants and/or fertilizer applications may also be integrated into this system application.

The synergistic effects allow the application rates of the individual active components to be reduced, a more enhanced improvement under a condition of reduced water irrigation with the same application rate, an extended application period and/or a reduced number of required individual applications and—as a result for the user—economical and ecologically more advantageous compositions to be used in methods of improving plant quality, density, color, and/or plant cell turgidity.

As an example, the combination of (i)+(ii)+(iii), or the combination of (i)+(ii)+(iv), or the combination of (i)+(ii)+(iii)+(iv), or the combination of (iii)+(i), or the combination of (iii)+(ii), according to the invention, allow synergistically increased effects which far and unexpectedly exceed the effects which can be achieved with the individual active substances (i), (ii), (iii) or (iv), applied in isolation.

Surprisingly, the ability of combinations according to the invention to improve plant quality, density, color, or plant cell turgidity is considerably higher than the sum of the activities of the individual active compounds, or than the activity of the known mixtures of two components. Thus, an unforeseeable true synergistic effect is present, and not just an addition of activities.

If the active compounds in the active compound combinations according to the invention are present in certain weight ratios, the synergistic effect is particularly pronounced. However, the weight ratios of the active compounds in the active compound combinations can be varied within a relatively wide range.

IV. Plants Treated

Compositions presented herein can be used to grow a plant under a condition of reduced water irrigation. Compositions presented herein can also be used to improve plant quality, density, color, and/or plant cell turgidity. In an embodiment, compositions can be applied to a plant before or during a condition of reduced water irrigation.

All plants and plant parts can be treated in accordance with the invention. As used herein, the term "plant" is understood to mean all plants and plant populations including desired and unwanted wild plants or crop plants (including naturally occurring crop plants). Plants include grass, such as turfgrass, trees, ornamentals, and garden vegetables.

Compositions presented herein can be applied to plants used in horticulture, plantations, urban forests, lawns, landscapes, golf courses, sports fields, parks, and commercial areas.

Suitable target crops include cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; *Lauraceae*, such as avocado, Cinnamonium or camphor; and also tobacco, nuts, coffee, eggplants, sugarcane, tea, pepper, grapevines, hops, the plantain family, latex plants and ornamentals.

The plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaccae* sp., *Lauraceae* sp., *Musaceae* sp. (for example banana plants and banana plantations), *Ruhiaceae* sp. (for example coffee), *Theaceae* sp., *Sterculiceae* sp., *Rutaceae* sp. (for example lemons, oranges and grapefruit); *Solanaceae* sp. (for example tomatoes). *Liliaceae* sp., *Asleraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceue* sp. (for example peas); major crop plants such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak Choi, kohlrabi, radishes, and oilseed rape, mustard, horseradish and cress), *Fabacae* sp. (for example beans, peanuts), *Papilionaceae* sp. (for example soybean), *Solanaceae* sp. (for example potatoes), *Chenopmliaceae* sp. (for example sugar beet, fodder beet, Swiss chard, beetroot); useful plants and ornamental plants in gardens and forests; and in each case genetically modified types of these plants.

The term "plants" is to be understood as including also plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop plant that has been rendered tolerant to imidazolinones, e.g. imazamox, by conventional methods of breeding (mutagenesis) is Clearfield™ summer rape (Canola). Examples of crop plants that have been rendered tolerant to herbicides or classes of herbicides by genetic engineering methods include glyphosate- and glufosinate-resistant maize varieties commercially available under the trade names RoundupReady™ and LibertyLink™.

The term "plants" is to be understood as including also plants which have been so transformed by the use of recombinant DNA techniques that they are capable of synthesizing one or more selectively acting toxins, such as are known, for example, from toxin-producing bacteria, especially those of the genus *Bacillus*.

V. Application of Compositions to Soil, Plants, and Plant Parts

The present compositions can be used for curative or protective control in conditions of reduced water irrigation. Thus, the present compositions can be applied to plant and/or soil before temporary or sustained periods of reduced water irrigation is anticipated. Also, the present compositions can be applied to plant and/or soil during temporary or sustained periods of reduced water irrigation.

The present compositions can be applied to the seed, the plant or plant parts, and/or the fruit or the soil in which the plants grow. For instance, the present compositions can be applied to the fruits, flowers, foliage, stalks, tubers or roots, of such plants.

Plant parts are understood to mean all parts and organs of plants above and below the ground, such as shoot, leaf, flower and root, examples of which include leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The present compositions can be applied to the plants, parts of the plants, seeds of the plants or the area under cultivation (soil of a field), preferably to the green plants and parts of the plants and, if appropriate, additionally to the soil of the field.

In an embodiment, the present compositions are applied as a foliar spray. In an embodiment, the present compositions are applied with sufficient water volumes for adequate coverage of foliage, according to the turf growth stage.

V(A). Turftrass

The present invention can be practiced on all grasses, including those used for lawns or other ornamental purposes, such as turfgrass, and those used as food or to produce grain for human or animal consumption. Some grasses, such as rye grasses, can be used both for food and for esthetic purposes.

In an embodiment, the present compositions are applied to turfgrasses, which are typically characterized as cool season turfgrasses and warm season turfgrasses. The present compositions can be applied to either warm or cool season turfgrasses.

Turf species that the described compositions can be used on include creeping bent grass, colonial bent grass, annual bluegrass, other *Poa* species of grasses, Bermuda grass, Rye grass, and other common grasses of golf courses, sport fields, commercial recreational areas, and sod farms.

Examples of cool season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.), and bulbous bluegrass (*Poa bulbosa* L.); the bentgrasses and redtop (*Agrostis* spp.), such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.); the fescues (*Festucu* spp.), such as red fescue (*Festuca rubra* L. spp. rubra), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.), meadow fescue (*Festuca elanor* L.); the ryegrasses (*Lolium* spp.), such as annual ryegrass (*Lolium multiflorum* Lam.), perennial ryegrass (*Lolium perenne* L.), italian ryegrass (*Lolium multiflorum* Lam.); and the wheatgrasses (*Agropyron* spp.), such as fairway wheatgrass (*Agropyron cristatum* (L.) Gaertn.), crested wheatgrass (*Agropyron desertorum* (Fisch.) Schult.), and western wheatgrass (*Agropyron smithii* Rydb.). Other cool season turfgrasses include beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm season turfgrasses include Bermudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore paspalum (*Paspalum vaginatum* Swartz) and sideoats grama (*Bouteloua curtipendula* (Michx. Torr.).

Cool season turfgrasses are generally preferred for treatment according to the invention. More preferred is bluegrass, bentgrass and redtop, fescue, and ryegrass. Bentgrass is most preferred. Examples of grasses that are useful as crops include corn or maize (*Zea mays*), sorghum (*Sorghum sudanense*), switchgrass (*Panicum virgatum*), millet (*Panicum miliaceum*), rice (*Oryza* spp.), wheat (*Triticum* spp.), oats (*Avena* spp.), barley (*Hordeum* spp.), and rye (*Secale cereale*).

The described compositions may be applied to healthy or diseased turfs. Prophylactic application to turf before conditions of reduced water irrigation may be helpful in reducing water stress and improving turf quality, density, color, and/or plant cell turgidity. Without being limited by any particular theory, application of the present compositions to turf may be helpful in treating one or more turf diseases, such as dollar spot, brown patch, anthracnose, gray leaf spot, and diseases of golf courses, sport fields, and sod farms. The described compositions may also be helpful in improving turf quality, density, color, and/or plant cell turgidity during reduced water conditions in the summer.

Cool-season grasses such as tall fescues, bluegrasses and bentgrasses are prone to damage during summer heat and summer decline leading to reduced root mass in the summer months. Surprisingly, it has been found that turf treated with the present composition retain turf quality through summer stress by alleviating plant stresses, enhancing disease resistance through induced system resistance, and protecting the plant from the adverse effects of solar radiation.

Warm-season grasses, such as Bermudagrass and Zoysiagrass, influenced by the effects of insufficient sunlight during the spring and fall, are prone to losing chlorophyll and premature senescence. Surprisingly, it has been found that treatment with the present compositions reduce the negative effects on plant growth promoting earlier spring green-up, turf fill-in, and extended turf quality in the fall.

V(B). Application Rates

When using the present compositions, application rates can be varied within a relatively wide range, depending on the kind of application. In the treatment of parts of plants, the application rates of compositions are generally between 0.1 and 10 000 g/ha, preferably between 10 and 1000 g/ha. In the treatment of seed, the application rates of the compositions are generally between 0.001 and 50 g per kilogram of seed, preferably between 0.01 and 10 g per kilogram of seed. In the treatment of the soil, the application rates of the compositions are generally between 0.1 and 10 000 g/ha, preferably between 1 and 5000 g/ha.

Furthermore, embodiments of the composition may be applied at 1 to 100 gallons per acre, or 1 to 50 gallons per acre, or 1 to 10 gallons per acre, or 1 to 5 gallons per acre, or 1 to 4 gallons per acre, or 1 to 3 gallons per acre, or 2 to 10 gallons per acre, or 2 to 5 gallons per acre, or 2 to 4 gallons per acre, or 2 to 3 gallons per acre.

In other embodiments, the composition may be applied at 1 to 100 gallons/1000 sq. ft., or 1 to 50 gallons/1000 sq. ft., or 1 to 10 gallons/1000 sq. ft., or 1 to 5 gallons/1000 sq. ft., or approximately 1 to 2 gallons/1000 sq. ft.

In other embodiments, the composition may be applied at 0.1 to 100 oz./1000 sq. ft., or 1 to 50 oz./1000 sq. ft., or 1 to 10 oz./1000 sq. ft., or 1 to 6 oz./1000 sq. ft.

Components of the composition may be applied simultaneously or sequentially. In an embodiment where components of the present compositions are not applied simultaneously, the rate of application of each component will depend on the component and the kind of application.

Antioxidants, such as N', N'-diformyl urea, can be applied to a target area at a concentration ranging from 0.001 to 10 kilograms per hectare (kg/ha), preferably from 0.01 to 3.5 kg/ha, more preferably from 0.1 to 1 kg/ha, most preferably from 0.2 to 0.8 kg/ha. The antioxidants may also be applied at concentrations ranging from 1 g to 500 g a.i./ha, or 1 g a.i./ha to 250 g a.i./ha, or 1 to 150 g a.i./ha, or 1 to 50 g a.i./ha. Antioxidants may also be applied at concentrations ranging from 0.001 to 1000 g a.i./100 sq. m., or 0.01 to 1000 g a.i./100 sq. m., or 0.1 to 1000 g a.i./100 sq. m, or 1 to 1000 g a.i./100 sq. m., or 1 to 100 g a.i./100 sq. m., or 1 to 10 g a.i./100 sq. m. Antioxidants may also be applied at concentrations ranging from 0.001 lbs a.i./gallon to 1 lbs a.i./gallon, or 0.01 lbs a.i./gallon to 1 lbs a.i./gallon, or 0.1 lbs a.i./gallon to 1 lbs a.i./gallon. Furthermore, in some embodiments, antioxidants can be applied at concentrations ranging from 1 to 1000 g/L, or 1 to 100 g/L, or 1 to 50 g/L, or 20 to 40 g/L.

Plant strengtheners, such as phosphorous acid, can be applied to a target area at a concentration ranging from 0.001 to 10 kilograms per hectare (kg/ha), preferably from 0.01 to 3 kg/ha, more preferably from 0.1 to 1 kg/ha, most preferably from 0.2 to 0.8 kg/ha. Plant strengtheners may also be applied at concentrations ranging from 0.001 to 1000 g a.i./100 sq. m., or 0.01 to 1000 g a.i./100 sq. m., or 0.1 to 1000 g a.i./100 sq. m, or 1 to 1000 g a.i./100 sq. m., or 1 to 100 g a.i./100 sq. m., or 1 to 10 g a.i./100 sq. m. Plant strengtheners may also be applied at concentrations ranging from 0.01 lbs a.i./gallon to 10 lbs a.i./gallon, or 0.1 lbs a.i./gallon to 10 lbs a.i./gallon, or 1 lbs a.i./gallon to 10 lbs a.i./gallon. The plant strengtheners may also be applied at concentrations ranging from 1 to 1000 g/L, or 100 to 500 g/L, or 200 to 300 g/L.

Radiation managers, such as Pigments, can be applied to a target area at a concentration ranging from 0.001 to 10 kilograms per hectare (kg/ha), preferably from 0.01 to 2 kg/ha, more preferably from 0.1 to 1 kg/ha, most preferably from 0.2 to 0.8 kg/ha. Radiation managers may also be applied at concentrations ranging from 0.001 to 1000 g a.i./100 sq. m., or 0.01 to 1000 g a.i./100 sq. m., or 0.1 to 1000 g a.i./100 sq. m, or 1 to 1000 g a.i./100 sq. m., or 1 to 100 g a.i./100 sq. m., or 1 to 10 g a.i./100 sq. m. Radiation managers may also be applied at concentrations ranging from 0.001 lbs a.i./gallon to 1 lbs a.i./gallon, or 0.01 lbs a.i./gallon to 1 lbs a.i./gallon, or 0.1 lbs a.i./gallon to 1 lbs a.i./gallon. In other embodiments, radiation managers, may be applied at a concentration ranging from 0.01 ml/L to 10 ml/L, or 0.1 ml/L to 10 ml/L, or 1 ml/L to 10 ml/L.

[000181] Plant growth regulators, such as trinexapac-ethyl, or any of the other plant growth regulators mentioned in the disclosure, can be applied at a concentration ranging from 0.01 lbs a.i./gallon to 10 lbs a.i./gallon, or 0.1 lbs a.i./gallon to 10 lbs a.i./gallon, or 1 lbs a.i./gallon to 10 lbs a.i./gallon.

VI. Application Methods

The compositions of the invention are applied by known methods. In an embodiment, all of the components of the composition are present in a specified ratio to each other, and the composition is formulated as a concentrate to be diluted upon use. In another embodiment, the components are separately formulated and then mixed in the tank. In yet another embodiment, the concentrated formulations of the individual active substances, in optimal formulations, are mixed with water in the tank and the resulting spray mixture being applied.

A combined formulation of the present compositions has the advantage of being easier to apply since the quantities of the components are already presented in the correct ratio to each other. Moreover, the adjuvants in the formulation can be matched optimally to each other, while a tank mix of different formulations may lead to undesired combinations of adjuvants.

Spray treatments were applied with a $CO_2$ pressurized backpack sprayer equipped with Teejet nozzle tips calibrated to deliver from about 10 to about 80 GPA at 40 psi.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

VII. Reduced Water Irrigation

In an embodiment, methods and compositions presented herein are directed to growing a plant under a condition of reduced water irrigation. In another embodiment, methods and compositions presented herein are directed to improving plant quality, density, color, and/or plant cell turgidity under a condition of reduced water irrigation.

As used herein, the term "water irrigation" includes external irrigation, such as watering through sprinklers, hoses, and watering pipes, for example. The term "water irrigation" also includes natural irrigation, such as watering through rain, fog, and dew, for example.

As used herein, the term "reduced water irrigation" includes temporary and sustained periods of drought. Periods of reduced water irrigation ranges from about one day to about 6 months. For instance, periods of reduced water irrigation can span a season, such as a summer season. Period can range from about one day to about one week, from about one day to about one month, from about one month to about three months. Periods of reduced water irrigation can also be referred to as "dry down" periods.

In addition to reducing the amount of external watering, a condition of reduced water irrigation can result from heat due to a rise in ambient temperature. A condition of reduced water irrigation can also result from temporary and/or sustained drought-like conditions.

The amount of reduced water irrigation depends on the type of plant, the type of soil, the location of the plant (e.g., elevations), and the overall landscape and microenvironment (e.g., temperatures) of the target plant. In an embodiment, plants and/or soil treated with the present compositions exhibit improved quality, density, color, and/or plant cell turgidity under a condition of at least 3% reduction in water irrigation, such as at least 5%, at least 10%, at least 15%, at least 20%, at least 25%, at least 30%, at least 35%, at least 40%, at least 45%, at least 50% reduction in water irrigation. Quality, density, color, and/or plant cell turgidity is improved in plants treated with the present compositions in comparison to non-treated plants, particularly under conditions of reduced water irrigation.

In an embodiment, plants and/or soil treated with the present compositions exhibit less water stress under conditions of reduced water irrigation. For example, plants treated with the present compositions exhibit less grey leaf color, less tip burn, less chlorophyll breakdown, and less cell lysis.

Surprisingly, it has been found that application of the present compositions to plants promotes healthier roots, increases plant drought tolerance, and improves plant water utilization. One aspect of the present invention leads to a reduction in the need for hand watering and a general saving of water use. While not wishing to be bound by any particular theory, it is believed that improvement in function of healthier plant roots after application of the present compositions leads to more efficient uptake of plant nutrients. While not wishing to be bound by any particular theory, it is also believed that improvement in cell turgidity after application of the present compositions results in a healthier and sturdier plant structure, reducing the impact of traffic or mechanical damage.

In another aspect of the invention, the present compositions induce systemic resistance in plants, which result in production of plant metabolites responsible for improving plant processes and increasing resistance to diseases.

In yet another aspect of the invention, the present compositions act as a systemic fungicide and booster of plant defense mechanisms, which may suppress Pythium blight and damping-off diseases of turfgrass on sod farms, golf courses, sport fields, parks, residential and commercial sites. In an embodiment, the present compositions are applied as preventative applications when conditions first favor disease and are then repeated at intervals described herein. The present compositions can be applied at higher rates under more severe disease conditions.

In yet another aspect of the invention, the present compositions are used for the prevention or alleviation of stress from drought, solar radiation, and other oxidative processes on turfgrasses located, for example, on sod farms, golf courses, sport fields, parks, residential and commercial sites. In an embodiment, the present compositions are applied as preventative applications prior to the occurrence of adverse weather conditions or before watering restrictions are imposed, and the applications are repeated at intervals described herein. The present compositions can be applied at higher rates under severe drought conditions or irrigation reductions. In an embodiment, the present compositions are used in conjunction with best turf management practices as is well known to one of ordinary skill in the art.

Use of the present compositions result in at least one of the following unexpected and surprising advantages: better drought tolerance; improved water utilization; saves water expenses; reduces need for hand watering; retains turf quality through summer stress; reduces plant stress thus requiring less watering; reduces afternoon syringing (i.e., a light application of water to turf foliage; enhances disease resistance from a healthier root system; provides enhanced plant health to minimize water uptake requirements; drought stress protection; water optimization; reduces water needs; causes turf grass exits dormancy for faster green-up; provides more efficient root uptake of surrounding soil moisture; reduces irrigation budget; reduces cost of watering; reduces irrigation needs; and greener lawn with less water requirements.

VIII. Plant Quality, Density, Color, Reduced Vegetative Index

In an embodiment, methods and compositions presented herein are directed to growing a plant under a condition of reduced water irrigation. In another embodiment, methods and compositions presented herein are directed to improving plant quality, density, color, and/or plant cell turgidity. In yet another embodiment, methods and compositions presented herein are practiced under a condition of reduced water irrigation.

As used herein, the term "plant quality" refers to signs of heat stress, drought stress, pest infection, and/or majority of plant death.

As used herein, the term "plant density" refers to uniformity in plant density, such as with plant growth density.

As used herein, the term "plant color" refers to the native color of the target plant. In an embodiment, the plant color is green and an improved plant color refers to the lushness of the green plant color.

As used herein, the term "RVI" refers to ratio vegetative index.

Plant quality, density, color, and/or plant cell turgidity can be measured, for example, using visual quality ratings assigned to a 1-9 scale (1=death of majority of the turf and 9=attractive green color and dense, uniform growth). Plants treated with embodiments of the disclosure may possess a visual quality rating that is higher than plants not treated with a composition according to the disclosure, for instance: 10% higher, 20% higher, 30% higher, 40% higher, 50% higher, 60% higher, 70% higher, 80% higher, 90% higher, and 100% higher are possible, or 10%-90%, or 10%-80%, or 10%-70%, or 10%-60%, or 10%-50%, or 10%-40%, or 10%-30%, or 10%-20%, higher visual quality ratings are possible, as compared to plants not treated with a composition as claimed. Additionally, plant quality, density, color, and/or plant cell turgidity can be assessed using, for example, crop circle assays (shoot density), using chlorophyll and/or carotenoid measurements with a chlorophyll meter, and/or using readings of soil moisture with a probe. For instance, chlorophyll and carotenoids can be extracted from a plant being studies by first soaking fresh shoots in dimethyl sulfoxide (DMSO) in the dark, and then measuring absorbance of each extractant at 663 nm, 645 nm, and 470 nm to determine chlorophyll content. Chlorophyll content can be quantified, for example, using the formula of Amon (1949) and carotenoids content can be quantified, for example, using the formula of Lichtenthaler and Wellburn (1983). Plants treated with embodiments of the disclosure may possess a chlorophyll content that is higher than plants not treated with a composition according to the disclosure, for instance: 10% higher, 20% higher, 30% higher, 40% higher, 50% higher, 60% higher, 70% higher, 80% higher, 90% higher, and 100% higher are possible, or 10%-90%, or 10%-80%, or 10%-70%, or 10%-60%, or 10%-50%, or 10%-40%, or 10%-30%, or 10%-20%, higher chlorophyll contents are possible, as compared to plants not treated with a composition as claimed. Yet another means of assessing plant quality, density, color, and/or plant cell turgidity can be performed by measuring chlorophyll fluorescence (Fv/Fm) using a plant photosynthesis efficiency analyzer (such as that available from ADC Bioscientific Limited, Herts, England).

Plant quality, density, color, and/or plant cell turgidity can also be assessed by collecting and measuring shoot samples and/or root cores before and after application of the present compositions, and/or before, during, and after conditions of reduced water irrigation in which fresh and dry weights (g) of shoots and/or root cores are obtained. For instance, samples of shoots and roots at the end of a period to be studied can be cleaned and dried (for example, at 80° C. in an oven for 72 hours), and the dry weight of the shoots and roots indicate the biomass of the shoots and roots. Plants treated with embodiments of the disclosure may possess higher shoot and root weights than plants not treated with a composition according to the disclosure, for instance: 10% higher, 20% higher, 30% higher, 40% higher, 50% higher, 60% higher, 70% higher, 80% higher, 90% higher, and 100% higher are possible, or 10%-90%, or 10%-80%, or 10%-70%, or 10%-60%, or 10%-50%, or 10%-40%, or 10%-

30%, or 10%-20%, shoot and root weights are possible, as compared to plants not treated with a composition as claimed.

Yet another parameter for assessing plant quality, density, color, and/or plant cell turgidity is by determining root mortality, which can be measured, for example using the method of Knievel (1973) with modification. First, samples of clean fresh roots can be incubated with 0.6% 2,3,5-triphenyltetrazolium chloride (in 0.05 M phosphate buffer, pH 7.4) for 24 hours in the dark at 30° C. Next, roots can be rinsed and extracted with 95% ethanol at 70° C. for 4 hours. The extractant can then be measured for absorbance at 490 nm to determine root mortality.

The following non-limiting examples illustrate embodiments of the present invention.

EXAMPLES

Example 1

The following test methods were used to evaluate compositions according to the invention. Exemplary invention compositions (1)-(8) listed in Table 1 below were diluted into water, and then applied to exemplary sample turf grass at the application concentrations indicated in Table 1 below sprayed at approximately 14 day intervals, and the warm season grass plots were sprayed at approximately 21 day intervals. All untreated plots were sprayed with water alone.

Three different turf species were treated with the compositions: (a) A-series bentgrass grown on greens mix (specifications established by the U.S. Golf Association), and maintained at a mowing height of 0.160"; (b) "Tifway" bermudagrass grown on soil mapped as Cecil sandy loam, and maintained at a mowing height of 1"; and (c) "Zeon" zoysiagrass grown on soil mapped as Cecil sandy loam, and maintained at a mowing height of 1". Trials were arranged in a randomized complete block design with four replicates per treatment. Individual bentgrass plots were 6' wide by 6' long, and the plots of bermudagrass and zoysiagrass were 3' wide by 6' long. All plots were set up with a split plot design to include treatment with the compositions.

At the time of first application of the compositions, exemplary sampled turf grass was lush green, uniform in density, and lacked any signs of heat or drought stress. Trials were maintained using a standard fertility program. Plots were pest-free and required no special maintenance.

A. Reduced Irrigation Regimes

For the bentgrass fields, three exemplary irrigation regimes were implemented throughout the duration of the

TABLE 1

Compositions (1)-(8)

| Composition | Applied Concentration | Plant Strengthener | Antioxidant | Radiation Manager | Plant Growth Regulator | Reference in FIGS. |
|---|---|---|---|---|---|---|
| 1 | 2 gallons (total composition)/acre | 2.6367 lbs a.i./gallon Di- and mono-potassium salt of phosphorous acid | 0.235 lbs a.i./gallon N,N-diformylurea | 0.30 lbs a.i./gallon Pigment green 7 | | Depicted in FIGS. 1, 3, 5, 7, 9, 11, & 13 as "A2" |
| 2 | 2 gallons (total composition)/acre | 2.6367 lbs a.i./gallon Di- and mono-potassium salt of phosphorous acid | 0.235 lbs a.i./gallon N,N-diformylurea | 0.30 lbs a.i./gallon Pigment green 7 | 1.0 lb a.i./gallon Trinexapac-ethyl | Depicted in FIGS. 2, 4, 6, 8, 10, 12, & 14 as "A2 + P" |
| 3 | 4 gallons (total composition)/acre | 2.6367 lbs a.i./gallon Di- and mono-potassium salt of phosphorous acid | 0.235 lbs a.i./gallon N,N-diformylurea | 0.30 lbs a.i./gallon Pigment green 7 | | Depicted in FIGS. 1, 3, 5, 7, 9, 11, & 13 as "A4" |
| 4 | 4 gallons (total composition)/acre | 2.6367 lbs a.i./gallon Di- and mono-potassium salt of phosphorous acid | 0.235 lbs a.i./gallon N,N-diformylurea | 0.30 lbs a.i./gallon Pigment green 7 | 1.0 lb a.i./gallon Trinexapac-ethyl | Depicted in FIGS. 2, 4, 6, 8, 10, 12, & 14 as "A4 + P" |
| 5 | 2 gallons (total composition)/acre | 3.52 lbs a.i./gallon Di- and mono-potassium salt of phosphorous acid | 0.235 lbs a.i./gallon N,N-diformylurea | 0.28 lbs a.i./gallon Pigment green 7 | | Depicted in FIGS. 1, 3, 5, 7, 9, 11, & 13 as "B2" |
| 6 | 2 gallons (total composition)/acre | 3.52 lbs a.i./gallon Di- and mono-potassium salt of phosphorous acid | 0.235 lbs a.i./gallon N,N-diformylurea | 0.28 lbs a.i./gallon Pigment green 7 | 1.0 lb a.i./gallon Trinexapac-ethyl | Depicted in FIGS. 2, 4, 6, 8, 10, 12, & 14 as "B2 + P" |
| 7 | 3 gallons (total composition)/acre | 3.52 lbs a.i./gallon Di- and mono-potassium salt of phosphorous acid | 0.235 lbs a.i./gallon N,N-diformylurea | 0.28 lbs a.i./gallon Pigment green 7 | | Depicted in FIGS. 1, 3, 5, 7, 9, 11, & 13 as "B3" |
| 8 | 3 gallons (total composition)/acre | 3.52 lbs a.i./gallon Di- and mono-potassium salt of phosphorous acidid | 0.235 lbs a.i./gallon N,N-diformylurea | 0.28 lbs a.i./gallon Pigment green 7 | 1.0 lb a.i./gallon Trinexapac-ethyl | Depicted in FIGS. 2, 4, 6, 8, 10, 12, & 14 as "B3 + P" |

For comparison, the following composition was also evaluated on the exemplary turf grass samples evaluated: 1.0 pound of active ingredient trinexapac-ethyl per gallon applied at 0.07 ounces per 1000 square feet.

All treatments were applied using a $CO_2$ pressurized backpack sprayer equipped with Teejet flat fan nozzles calibrated to deliver 40 GPA at 40 psi. Bentgrass plots were study: (a) "full irrigation" refers to the watering of certain plots for 8 minutes every other day; (b) "25% reduced irrigation" refers to the watering of certain plots for 6 minutes every other day; and (c) "50% reduced irrigation" refers to the watering of certain plots for 4 minutes every other day. The bermudagrass and zoysiagrass were irrigated at either (a) "full irrigation", which refers to the watering of certain plots for 20 minutes every other day, or (b) "50% reduced irrigation", which refers to the watering of certain plots for 10 minutes every other day.

A dry down period was carried out for three days in the full irrigation regime for the bentgrass, and for five days in each irrigation regime for the bermudagrass and zoysiagrass. During the dry down period, no water was applied to any of the evaluated turfgrass plots.

For the bentgrass field studies, the dry-down was conducted on the full irrigation field only due to extreme heat and water stress in fields under reduced irrigation regimes.

B. Test Results

As demonstrated in the representative non-limiting indicators described below, treatment of grass, especially turf grass, with compositions provided herein resulted in consistent, higher quality turf grass under varying reduced irrigation regimes when compared to untreated (i.e., "UTC") grass samples.

During the study, turf grass plots were generally evaluated weekly except during the dry-down period when plots were evaluated daily. Data included visual quality ratings, chlorophyll index values, and canopy temperature readings.

1. Visual Quality Ratings

Turf quality was visually rated at a scale from 1 to 9 according to the density, greenness, density of the grass, and uniformity of the grass, with 1 being the worst and 9 being the best. A visual scale of 1 further indicated death in the majority of the turf grass.

1(a). Bentgrass

FIGS. 1-6 demonstrate the visual quality ratings for the evaluated bentgrass. Using visual quality ratings as an exemplary indicator, FIGS. 1-6 demonstrate that treatment of bentgrass with compositions A or B positively enhanced turf quality when averaged over the course of the study as compared to the untreated ("UTC") control. FIGS. 1-6 further demonstrate that treatment of Zoysiagrass with compositions A+P or B+P greatly enhanced turfgrass quality when irrigation was reduced by 50%. As illustrated in FIGS. 1-6, bentgrass treated with the following composition exhibited the greatest positive impact on turf quality: B+P applied at 2 gallons/acre, and A+P applied at 4 gallons/acre.

Due to the extreme heat and water stress the reduced irrigation fields were under, the dry-down for this sampled bentgrass was conducted on the full irrigation field only. The only notable difference among treatments was that bentgrass treated with composition A at 2 gall/acre exhibited a 4% increase in quality (when compared to the control), and bentgrass treated with composition A+P at 2 gall/acre exhibited a 6% increase in quality.

1(b). Bermudagrass

FIGS. 7-10 demonstrate the visual quality ratings for the evaluated bermudagrass. Using visual quality ratings as an exemplary indicator, FIGS. 7-10 demonstrate that treatment of Bermudagrass with compositions A, A+P, B, and B+P positively enhanced turf quality when averaged over the course of the study as compared to the untreated control. Treatment with composition A 4 at gall/acre exhibited the most enhanced turf quality, with a 7% increase in quality from the untreated ("UTC") control under both fully irrigated and 50% reduced irrigation regimes. During the 5 day dry-down period, treatment of Bermudagrass with compositions A or B positively enhanced turf quality when compared to the UTC control. As illustrated in FIGS. 7-10, Bermudagrass treated with composition A at an application rate of 4 gallons/acre and composition B at an application rate of 3 gallons/acre afforded the most protection and exhibited the highest enhanced turf quality under water-stress conditions.

1(c). Zoysiagrass

FIGS. 11-14 demonstrate the visual quality ratings for the evaluated zoysiagrass. Using visual quality ratings as an exemplary indicator, FIGS. 11-14 demonstrate that treatment of zoysiagrass with composition A exhibited slightly better quality when compared to plots treated with composition A+P irrespective of water regime. Likewise, treatment of zoysiagrass with composition B exhibited slightly better quality when compared to plots treated with composition B+P irrespective of water regime. In the reduced irrigation regime, treatment of bentgrass with compositions A and A+P at 4 gallons/acre exhibited the most enhanced turf quality when compared to the control. During the course of the 5 day dry-down period, treatment with composition A and treatment with composition B positively enhanced turf quality when compared to the control. As illustrated in FIGS. 11-14, zoysiagrass treated with composition A at an application rate of 4 gallons/acre afforded the most protection and exhibited the most enhanced turf quality under water-stress conditions.

As shown in FIGS. 1-14, consistent effects in the sampled turfgrass as a result of treatment with the invention compositions were observed despite differences in the magnitude of the responses under the varying irrigation regimes and between the varying types of grass tested. FIGS. 1-14 show that treatment with composition A at 4 gallons/acre consistently resulted in higher quality turfgrass, especially in warm season grasses under the 50% reduced irrigation.

2. Chlorophyll Index Values

Chlorophyll was extracted by soaking 50 mg fresh shoots in 20 ml dimethyl sulfoxide (DMSO) in the dark for 72 hours. Absorbance of the extractant at 663 nm, 645 nm, and 470 nm was used to determine chlorophyll content using the formula of Amon (1949). Chlorophyll index values were measured using a Spectrum Field Scout© CM 1000™ chlorophyll meter.

Shoot samples were collected from the bentgrass plots once during the study. Plots were not mowed for three days prior to shoot collection. Shoots were obtained from every plot with a walk-behind reel mower fitted with a front catch bin. The mower was centered at the front edge of the plot, plot length was mowed and shoots removed from the front catch bin after each plot was completed. Dry weights (g) and N content (%) were obtained.

Data from assays measuring chlorophyll index values demonstrate that treatment of bentgrass, bermudagrass, and zoysiagrass with the invention compositions positively enhanced chlorophyll index values when averaged over the course of the study as compared to the untreated control. During the reduced irrigation regime(s) evaluated, treatment with invention compositions positively enhanced chlorophyll index values when compared to the control. As illustrated in the above exemplary indicator, grass treated with the invention compositions afforded protection and exhibited higher chlorophyll index values under water-stress conditions when compared to untreated ("UTC") controls.

3. Canopy Temperatures

Temperatures of sampled turfgrass were taken at [x] days after treatment with the invention compositions listed in Table 1. Canopy temperatures were measured using a Raytek© MiniTemp FS™ non-contact thermometer.

Data from assays measuring canopy temperatures demonstrate that treatment of bentgrass, bermudagrass, and zoysiagrass with the invention compositions positively enhanced canopy temperatures when averaged over the course of the study as compared to the untreated control. During the reduced irrigation regime(s) evaluated, treatment with invention compositions positively enhanced canopy temperatures when compared to the control. As illustrated in the above exemplary indicator, grass treated with the invention compositions afforded protection and exhibited more favorable canopy temperatures under water-stress conditions when compared to untreated ("UTC") controls.

4. Ratio Vegetation Index ("RVI")

A Crop Circle ACS-430 active crop canopy sensor (Holland Scientific, Inc.) provided classic vegetation index data (RVI, Ratio Vegetation Indices) from the turf canopy. Unlike passive radiometric light sensors, the Crop Circle ACS-430 is not limited by ambient lighting conditions and measurements were made by day due to its unique, light source technology. Information produced by the sensor can be utilized to quantify the impact of nutrients, water, disease or other growing conditions on the turf plant. The ratio vegetation index (RVI) is formed by dividing the near infra-red irradiance by the red irradiance. Study plots were scanned at intervals to collect this quantitative data.

Figure 15:
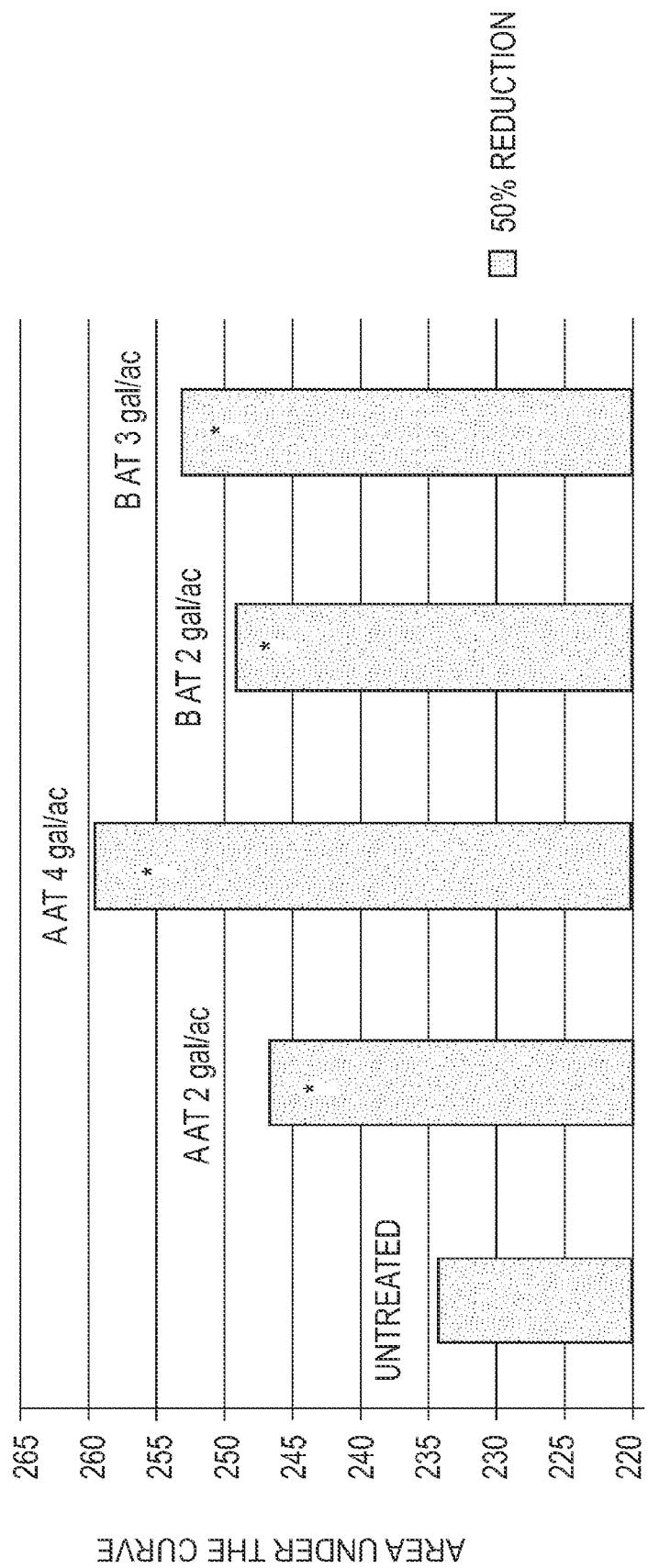
FIG. 15: shows results from an RVI experiment.
Figure 16:
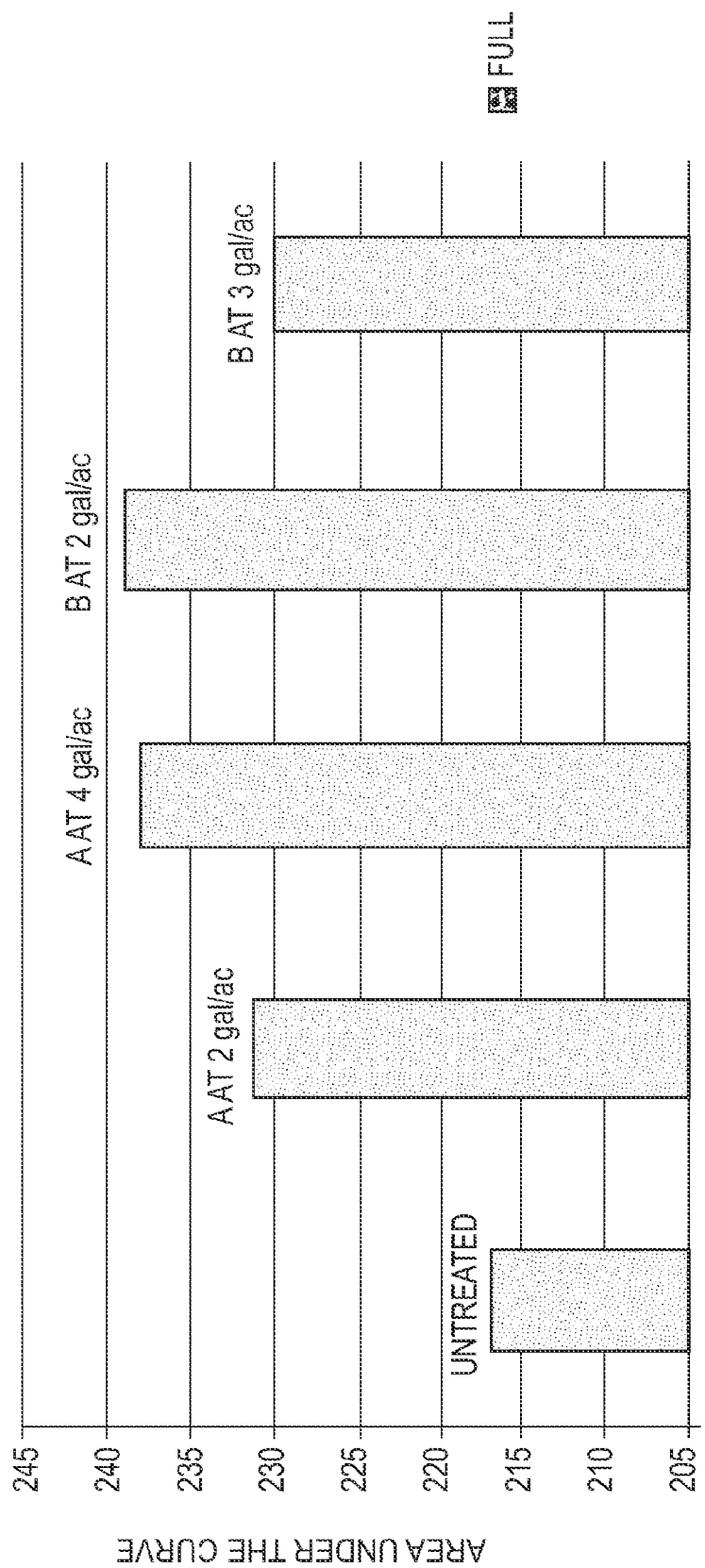
FIG. 16: shows results from an RVI experiment.
Figure 17:
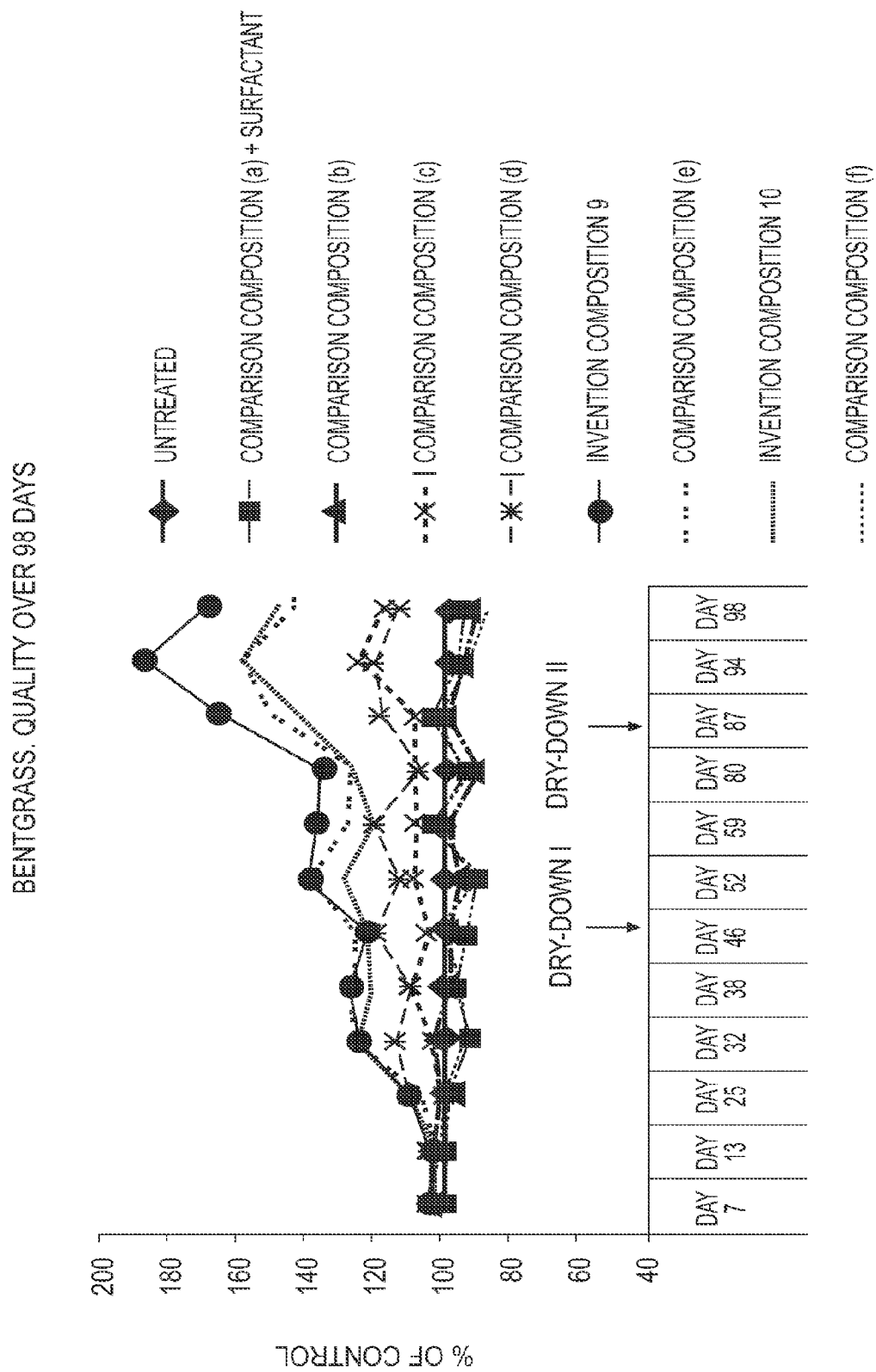
FIG. 17: shows results of an experiment on Bentgrass quality over 98 days.
Figure 19:
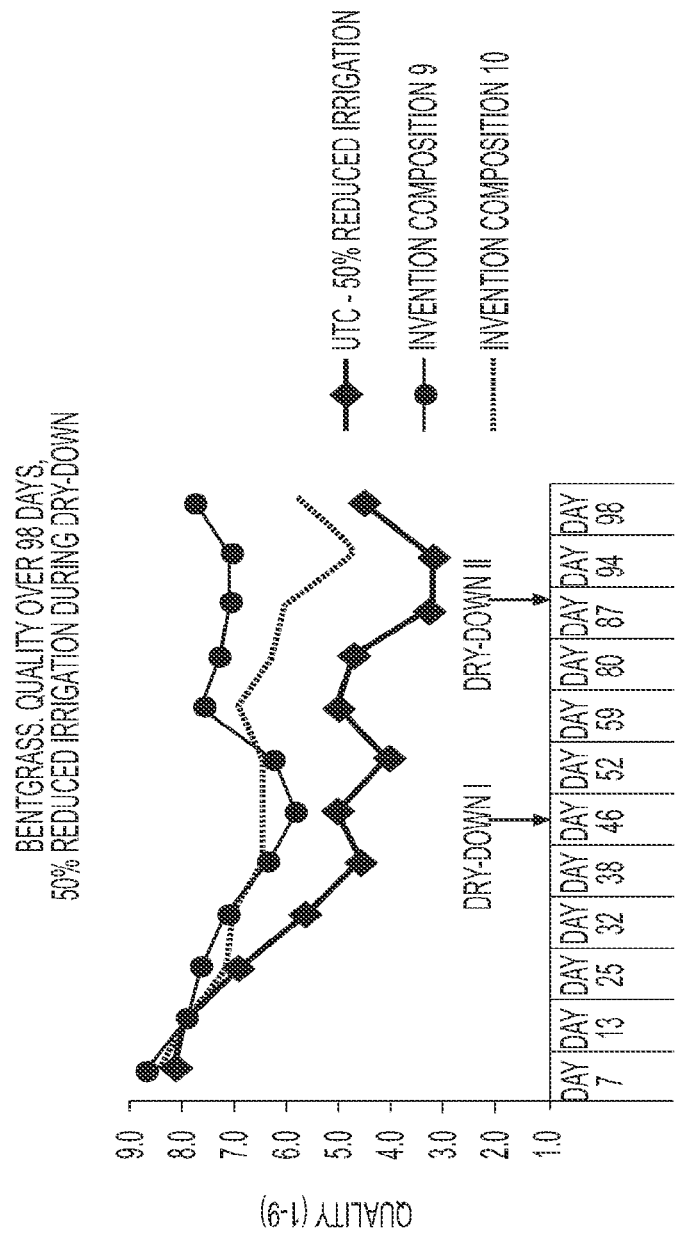
FIG. 19: shows results of an experiment on Bentgrass quality over 98 days.

Crop circle assays of sampled turfgrass were taken after treatment with the invention compositions listed in Table 1. FIGS. 15 and 16 demonstrate the ratio vegetative index ("RVI") for the evaluated zoysiagrass. Using RVI as an exemplary indicator, FIGS. 15 and 16 demonstrate that treatment of zoysiagrass with composition A and composition B positively enhanced vegetative index when averaged over the course of the study as compared to the untreated control. During 50% reduced irrigation regime, treatment with composition A and composition B positively enhanced the vegetative index when compared to the untreated control. As illustrated in the above exemplary indicator, grass treated with the invention compositions afforded protection and exhibited more favorable vegetative indices under water-stress conditions when compared to untreated controls.

Example 2

The following test methods were used to evaluate compositions according to the invention. For exemplary invention compositions (9) and (10) listed in the Table 2 below, the listed components were diluted into the following exemplary tank mixture, and the diluted components were then applied to exemplary sample turf grass at the application concentrations indicated.

(a) 0.72 pounds of active ingredient N, N-diformylurea per gallon applied at 1 ounce per 1000 square feet;

(b) 0.72 pounds of active ingredient N, N-diformylurea per gallon applied at 1.5 ounce per 1000 square feet;

(c) 0.72 pounds of active ingredient N, N-diformylurea per gallon applied at 2.0 ounce per 1000 square feet;

(d) 0.72 pounds of active ingredient N, N-diformylurea per gallon applied at 1.5 per 1000 square feet, and 1.0 pound of active ingredient trinexapac-ethyl per gallon applied at 0.07 ounces per 1000 square feet;

(e) 0.72 pounds of active ingredient N, N-diformylurea per gallon applied at 1, 1.5 or and 2 ounces per 1000 square feet, and 11.3 pounds of active ingredient di- & mono-potassium salts of phosphorous acid per gallon applied at 7 ounces per 1000 square feet;

(f) 100% pigment green 7 applied at 0.25 ounces per 1000 square feet; and (g) 0.72 pounds of active ingredient N, N-diformylurea per gallon applied at 1.5 per 1000 square feet "+Z (compound from [00069] long chain fatty alcohol ethoxylate)".

All treatments were applied using a $CO_2$ pressurized backpack sprayer equipped with Teejet flat fan nozzles calibrated to deliver 40 GPA at 40 psi. Plots were sprayed at approximately 14 day intervals, and the warm season grass plots were sprayed at approximately 21 day intervals. All untreated plots were sprayed with water alone.

Two different turf species were treated with the compositions: (a) "A-1" series creeping bentgrass grown on greens mix (specifications established by the U.S. Golf Association), and maintained at maintained at greens height (⅜"); and (b) Turf-Type tall fescue grown on native soil, mapped as Cecil sandy loam, and maintained at a height of 3". Trials were arranged in a randomized complete block design with four replicates per treatment. Individual bentgrass plots were 3' wide by 6' long, and fescue plots were 3' wide by 10' long. All plots were set up with a split plot design to include treatment with the compositions.

At the time of first application of the compositions, exemplary sampled turf grass was lush green, uniform in density, and lacked any signs of heat or drought stress. Trials were maintained using a standard fertility program and pest management programs. Plots were pest-free and required no special maintenance.

A. Reduced Irrigation Regimes

A dry down period was carried out twice for four days each time. During the dry down period, three exemplary

TABLE 2

Compositions (9) & (10)

| Composition | Applied Concentration | Plant Strengthener | Antioxidant | Radiation Manager | Plant Growth Regulator |
|---|---|---|---|---|---|
| 9 | 1.5 ounce of N,N-diformylurea/ 1,000 sq ft + 0.25 oz/1.000 sq ft Pigment green 7 + 0.07oz/1,000 sq ft Trinexapac-ethyl | | 0.72 lbs a.i./gallon N,N-diformylurea | 100% Pigment green 7 | 1.0 lb a.i./gallon Trinexapac-ethyl |
| 10 | 1.5 ounce of N,N-diformylurea/ 1,000 sq ft + 0.25 oz/1.000 sq ft Pigment green 7 + 6 oz/1,000 sq ft di & mono-potassium salts of phosphorous acid | 11.3 lbs a.i./gallon di & mono-potassium salts of phosphorous acid | 0.72 lbs a.i./gallon N,N-diformylurea | 100% Pigment green 7 | |

For comparison, the following compositions were also evaluated on the exemplary turf grass samples evaluated:

irrigation regimes were implemented: (a) "full irrigation"; (b) "25% reduced irrigation"; and (c) "50% reduced irrigation". Unless dry-down irrigation regimes were implemented, all plots received "adequate" irrigation throughout the course of the study.

Ambient air temperatures were recorded during the study, which included summer months. Irrigation was kept at adequate levels until ambient air temperatures were high and no rain forecast, at which time, the above reduced irrigation regimes were implemented. By doing so, heat and drought stress in the bentgrass and fescue grass systems treated with invention compositions were evaluated.

B. Test Results

As demonstrated in the representative non-limiting indicators described below, treatment of grass, especially turf grass, with compositions provided herein resulted in consistent, higher quality turf grass under varying reduced irrigation regimes when compared to untreated (i.e., "UTC") grass samples. During the study, turf grass plots were generally evaluated weekly except during the dry-down period when plots were evaluated daily. Data included visual quality ratings, chlorophyll index values, crop circle (vegetative indices), and soil moisture readings.

1. Visual Quality Ratings

Turf quality was visually rated at a scale from 1 to 9 according to the density, greenness, density of the grass, and uniformity of the grass, with 1 being the worst and 9 being the best. A visual scale of 1 further indicated death in the majority of the turf grass.

1(a). Creeping Bentgrass

FIGS. 16-19 demonstrate the visual quality ratings for the evaluated bentgrass. Using visual quality ratings as an exemplary indicator, FIGS. 16-19 demonstrate that treatment of bentgrass with compositions 9 or 10 positively enhanced turf quality when averaged over the course of the study as compared to the untreated ("UTC") control. Visual quality in untreated Bentgrass declined sharply in a summer month. Visual quality was significantly improved over the course of the season after treatment with composition 9; improvements of up to 80% over the untreated control were observed. During 25% and 50% reduced irrigation regimes, higher visual quality ratings were consistently observed for bentgrass treated with composition 9 or 10. Visual quality was enhanced in bentgrass treated with compositions 9 or 10 under the heat and drought stress associated with 50% reduced irrigation.

1(b). Tall Fescue

FIGS. 20 and 21 demonstrate the visual quality ratings for the evaluated tall fescue grass. Using visual quality ratings as an exemplary indicator, FIGS. 20 and 21 demonstrate that treatment of fescue grass with compositions 9 and 10 positively enhanced turf quality when averaged over the course of the study as compared to the untreated control.

Visual quality in untreated fescue grass declined and remained low during summer months. Visual quality was significantly improved over time after treatment with composition 10, resulting in consistent higher visual quality ratings during 25% and 50% reduced irrigation.

Treatment with composition 9 reduced fescue growth, with the largest effect observed under the full irrigation regime. Reduced growth was also observed when fescue grass was treated with comparison compositions (d).

During 25% and 50% reduced irrigation regimes, higher visual quality ratings were consistently observed for fescue grass treated with composition 9 or composition 10.

2. Chlorophyll Index Values

Chlorophyll was extracted by soaking 50 mg fresh shoots in 20 ml dimethyl sulfoxide (DMSO) in the dark for 72 hours. Absorbance of the extractant at 663 nm, 645 nm, and 470 nm was used to determine chlorophyll content using the formula of Amon (1949). Chlorophyll index values were measured using a Spectrum Field Scout© CM 1000™ chlorophyll meter.

Figure 23:
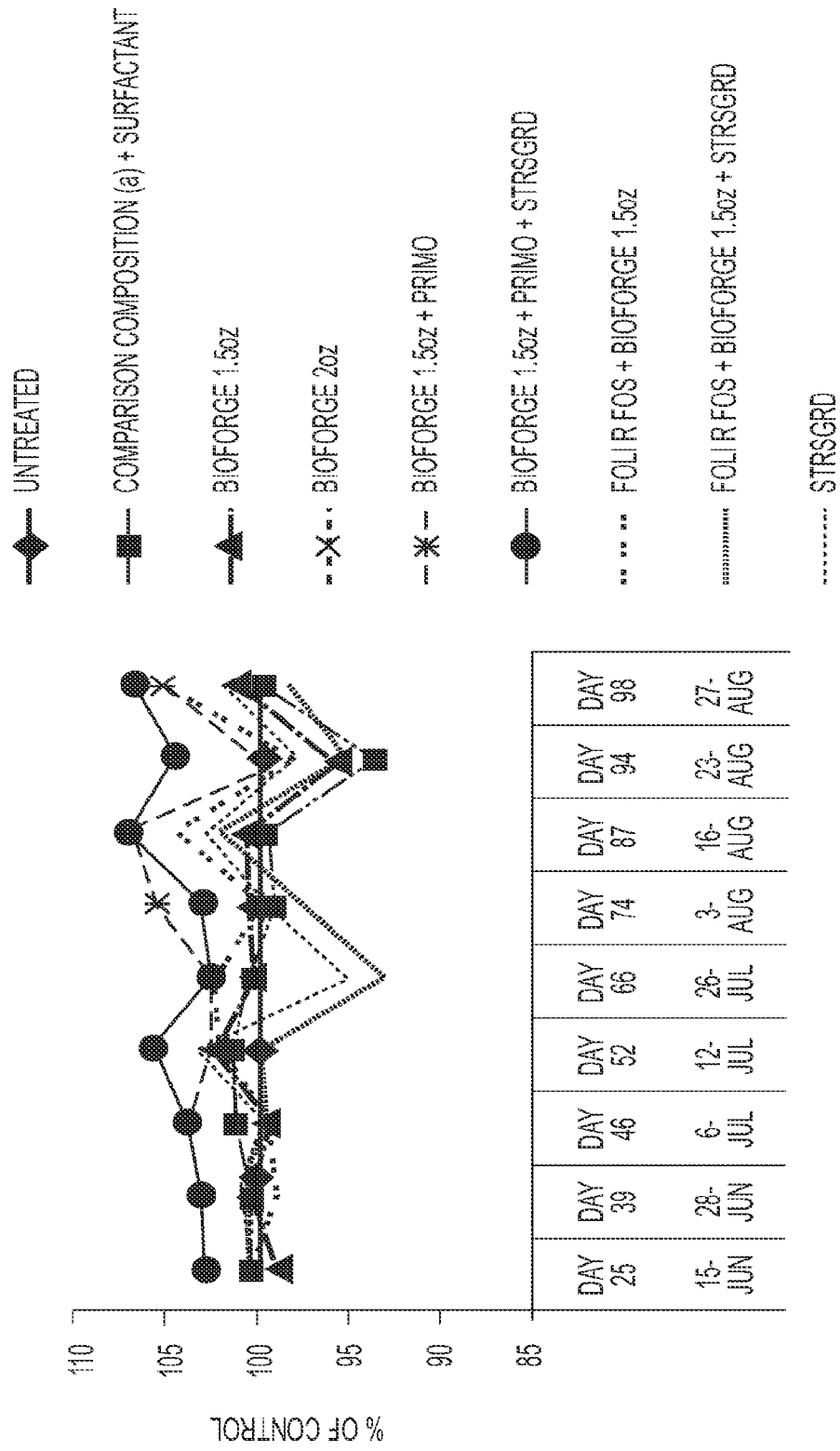
FIG. 23: shows results of an experiment on Bentgrass Chlorophyll index over 98 days.
Figure 25:
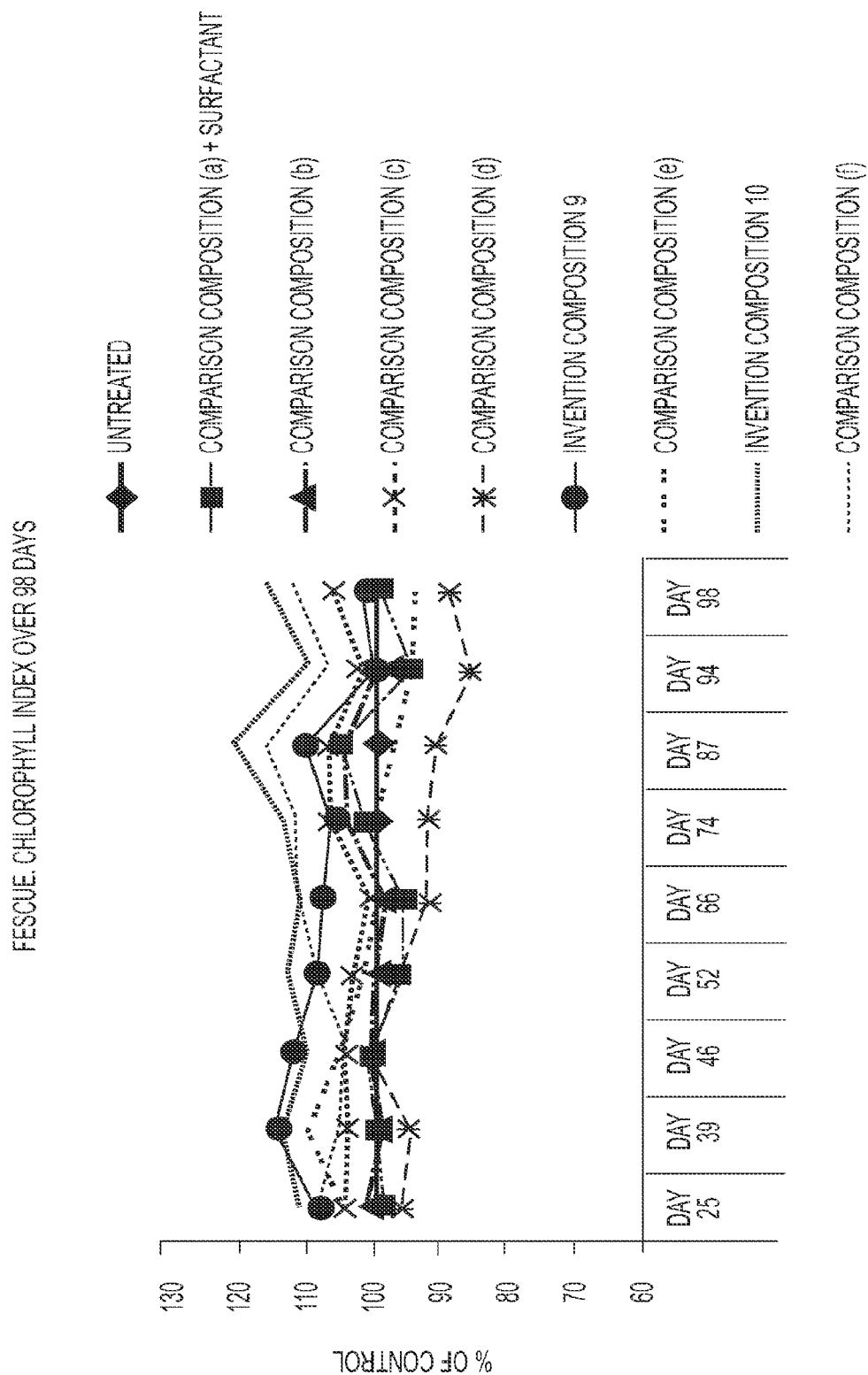
FIG. 25: shows results of an experiment on Fescue Chlorophyll index over 98 days.

Data from assays measuring chlorophyll index values are reflected in FIGS. 23 and 25, and demonstrate that treatment of bentgrass and fescue grass with invention compositions 9 and 10 positively enhanced chlorophyll index values when averaged over the course of the study as compared to the untreated control. During the reduced irrigation regimes evaluated, treatment with invention compositions 9 and 10 positively enhanced chlorophyll index values when compared to the control. As illustrated in the above exemplary indicator, grass treated with the invention compositions afforded protection and exhibited higher chlorophyll index values under water-stress conditions when compared to untreated ("UTC") controls.

3. Ratio Vegetation Index ("RVI")

A Crop Circle ACS-430 active crop canopy sensor (Holland Scientific, Inc.) provided classic vegetation index data (NDVI, Normalized difference vegetative index) from the turf canopy. Unlike passive radiometric light sensors, the Crop Circle ACS-430 is not limited by ambient lighting conditions and measurements were made by day due to its unique, light source technology. Information produced by the sensor can be utilized to quantify the impact of nutrients, water, disease or other growing conditions on the turf plant. NDVI is calculated from these individual measurements as follows:

$$NDVI = \frac{(NIR - VIS)}{(NIR + VIS)}$$

where VIS and NIR stand for the spectral reflectance measurements acquired in the visible (red) and near-infrared regions, respectively.

Figure 22:
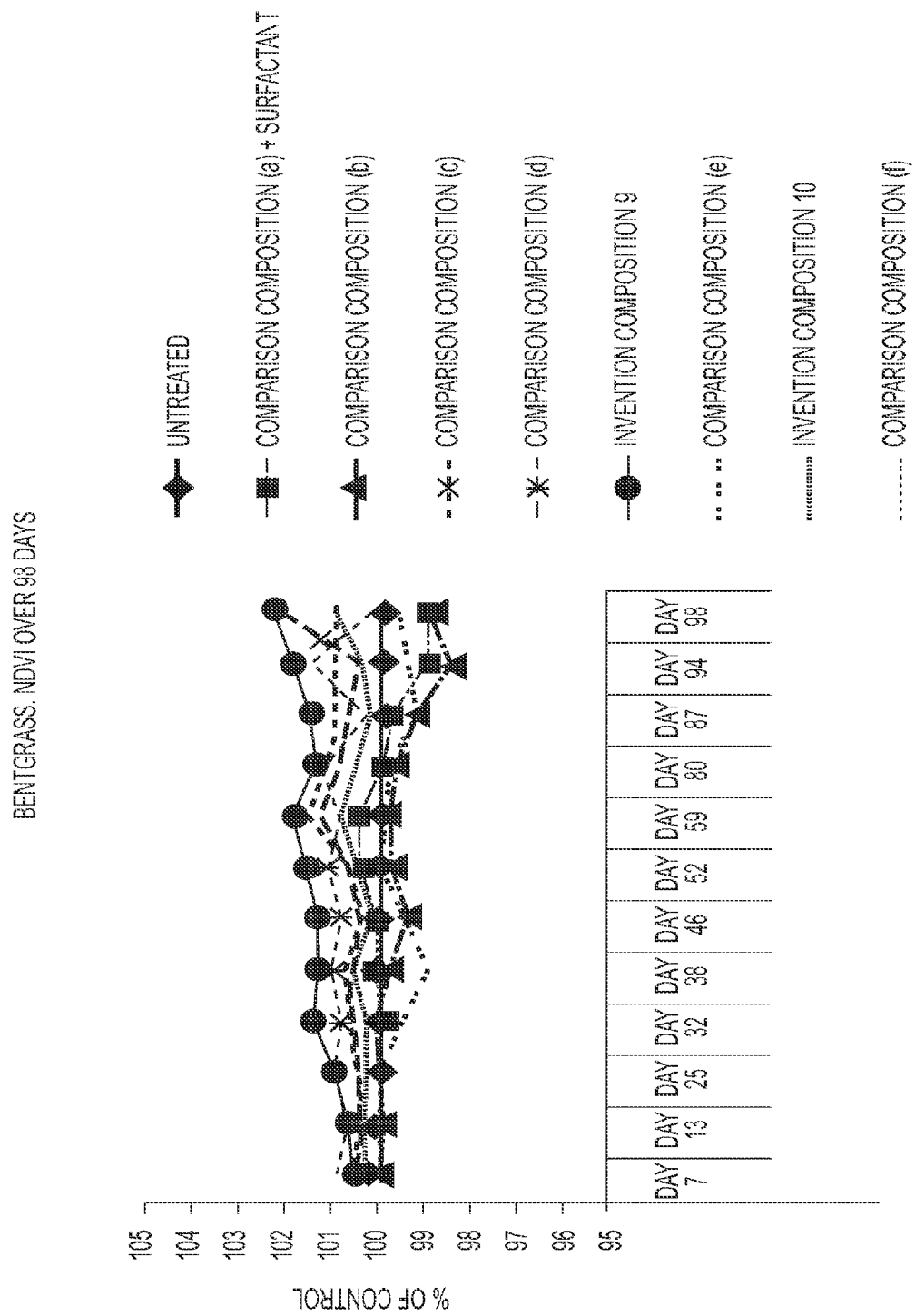
FIG. 22: shows results of an experiment on Bentgrass NDVI over 98 days.
Figure 24:
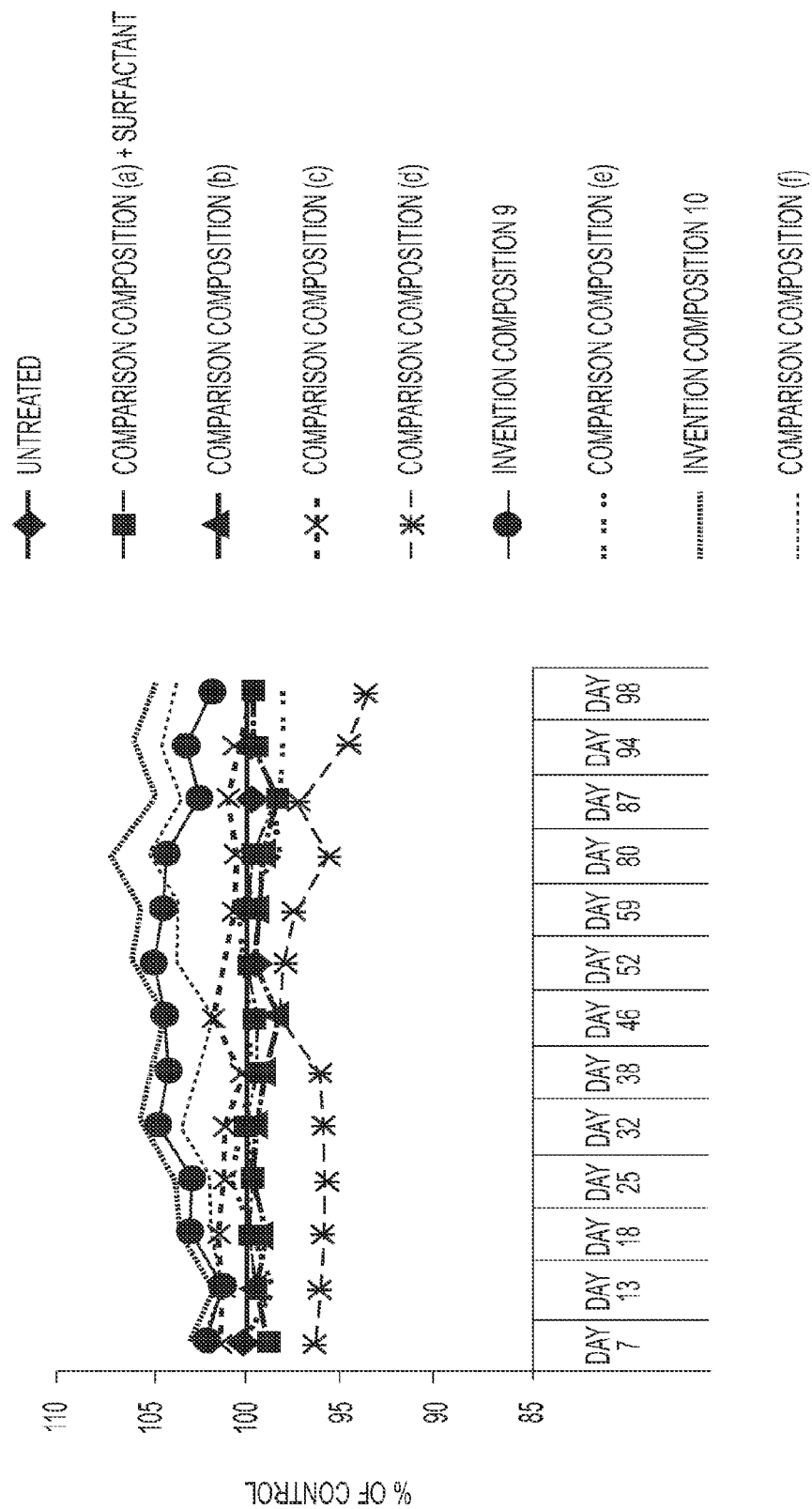
FIG. 24: shows results of an experiment on Fescue NDVI over 98 days

FIGS. 22 and 24 demonstrate the vegetative index ("NDVI") for evaluated bentgrass and fescue grass, respectively. Using NDVI as an exemplary indicator, FIGS. 22 and 24 demonstrate that treatment of bentgrass and fescue grass with composition 9 and composition 10 positively enhanced vegetative index when averaged over the course of the study as compared to the untreated control. During 25% and 50% reduced irrigation regimes, treatment with composition 9 and composition 10 positively enhanced the vegetative index when compared to the untreated control. As illustrated in the above exemplary indicator, grass treated with the invention compositions afforded protection and exhibited more favorable vegetative indices under water-stress conditions when compared to untreated controls.

4. Shoot and Root Samples

Shoot samples were collected twice during the study. Plots were not mowed for two days prior to shoot collection. Shoots were obtained from every plot with a walk-behind mower fitted with a bag attachment. The mower was centered at the front edge of the plot, plot length was mowed and shoots removed from the bag after each plot was completed. Shoot fresh and dry weights (g) were obtained.

Root cores were pulled twice during the study. Initial collection of roots occurred prior to first application of the compositions, and was a random sampling of twelve areas interspersed throughout the turf block. At the end of the study, one sample was pulled from every plot, turf was trimmed to the soil line, roots were washed and weighed (fresh weight in grams), roots were placed into a 60° C. oven for 48 hours, and dry weight of roots (in grams) were recorded.

Figure 26:
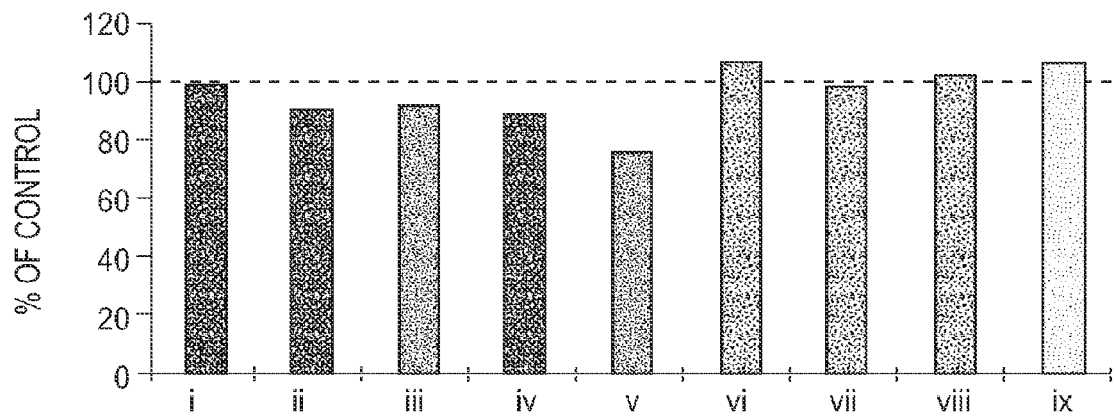
FIG. 26: shows results of an experiment on Fescue Shoot Fresh Weight.
Figure 27:
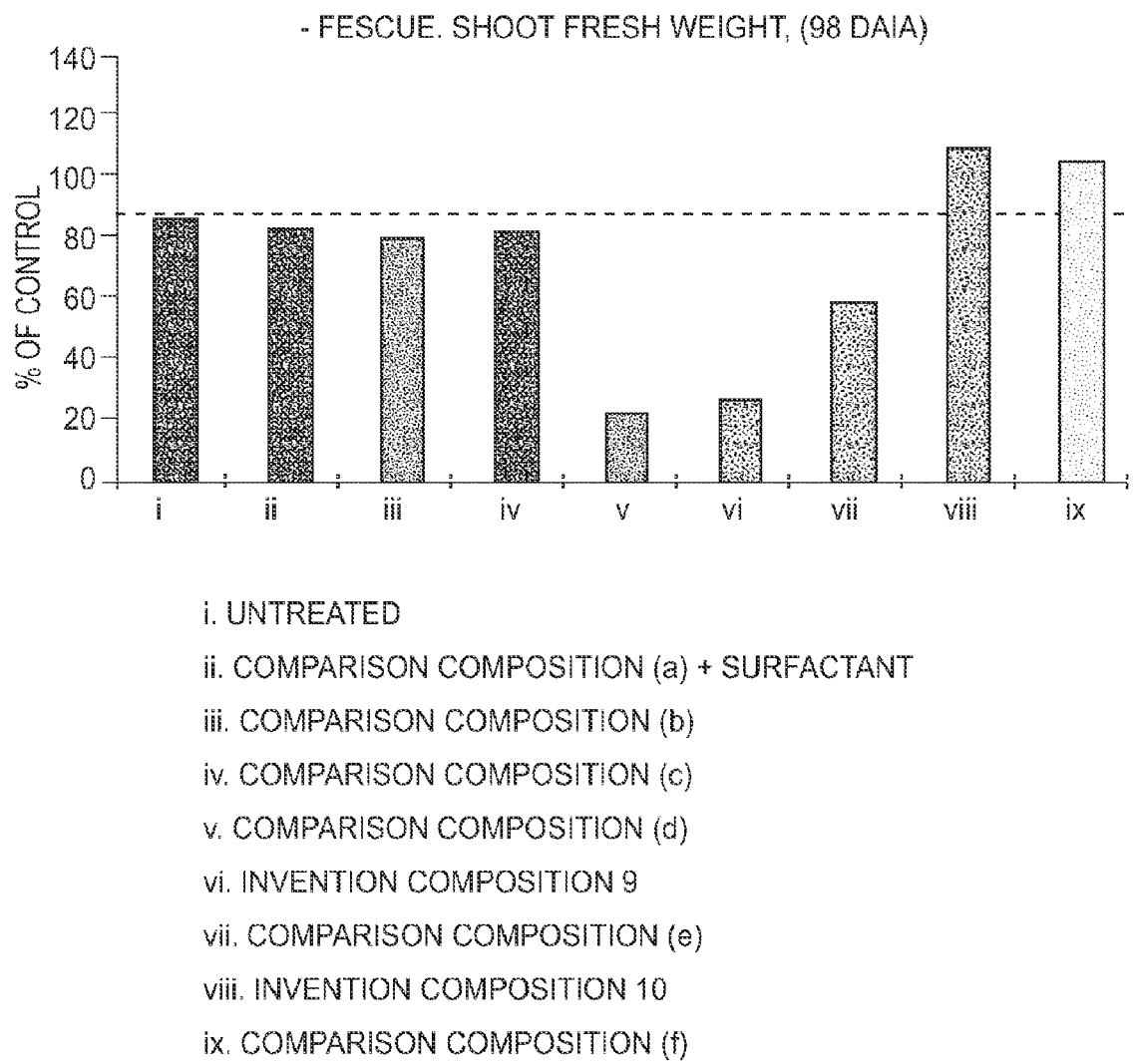
FIG. 27: shows results of an experiment on Fescue Shoot Fresh Weight.

FIGS. 26 and 27 illustrate the shoot fresh weight for evaluated fescue grass. Using shoot fresh weight as an exemplary indicator, FIGS. 26 and 27 demonstrate that treatment of fescue grass with composition 9 and composition 10 positively enhanced shoot fresh weight. During 25% and 50% reduced irrigation regimes (DAIA=days after initial application), treatment with composition 9 and composition 10 positively enhanced shoot fresh weight. As illustrated in the above exemplary indicator, grass treated with the invention compositions afforded protection and exhibited more favorable shoot fresh weight under water-stress conditions.

Example 3

The following test methods were used to evaluate compositions according to the invention.
A. Evaluated Compositions The compositions utilized in this experiment comprised the below components (A)+(B), or (A)+(B)+(C), in which:

Component (A)=CHIPCO SIGNATURE at a concentration of 4 oz/1000 sq. ft., which equals an active ingredient concentration of fosetyl-AL of 97.7 g ai/100 sq. m.

Component (B)=Phthalocyanine Green Pigment A at a concentration of 0.25 oz./1000 sq. ft.

Figure 28:
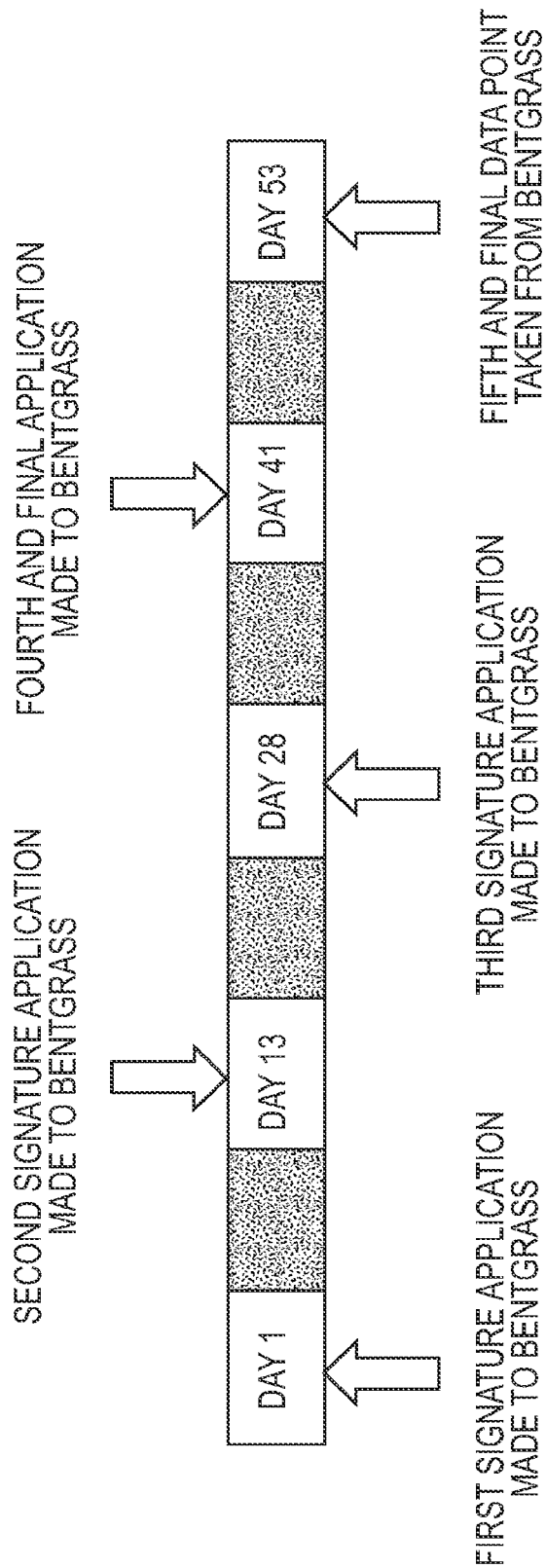
FIG. 28: shows experimental protocol timeline.
Figure 29:
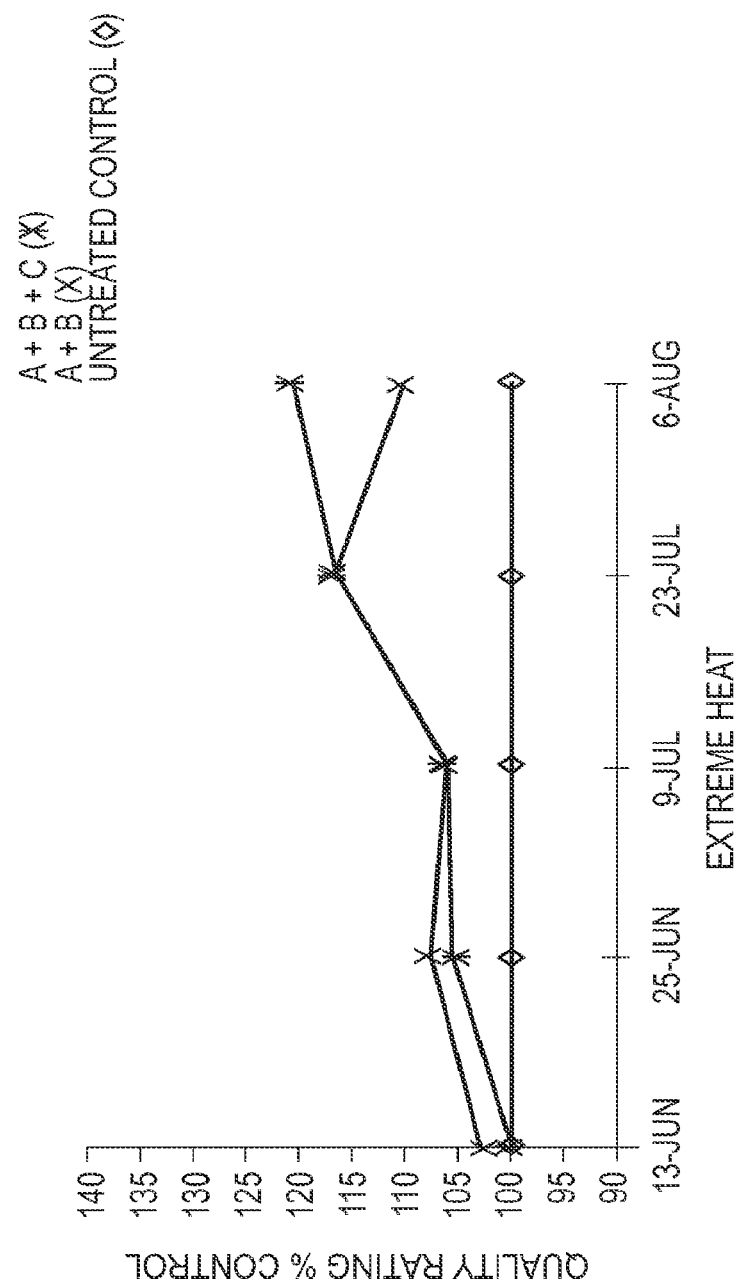
FIG. 29: shows results of an experiment on Quality Ratings in Bentgrass.

Component (C)=N', N'-diformyl urea, which is derived from a reaction of formic acid and urea at a concentration of 1.5 oz./1000 sq. ft.
B. Methodology Research was conducted on an A1/A4 bentgrass blend maintained at greens height. Trials were arranged in a randomized block design with 3 replicates per treatment. Individual bentgrass plots were 3' wide by 6' long. Treatments were applied using a CO2 pressurized backpack sprayer equipped with Teejet flat fan nozzles calibrated to deliver 40 GPA at 40 psi. Plots were sprayed at approximately 14 day intervals beginning mid-June. See FIG. 28. All untreated plots were sprayed with water alone. At time of first application, turf was a healthy green, uniform in density, and lacked any signs of heat or drought stress. Trials were maintained using a standard fertility program. Plots were pest-free and required no special maintenance.

Here compared are two irrigation regimes: full irrigation, and 25% reduced irrigation that were used throughout the duration of the study.

Data were generally taken bi-weekly during the course of the study, prior to the next spray application. Data included visual quality ratings which were assigned using a 1-9 scale (1=death of majority of the turf and 9=attractive green color and dense, uniform growth) and chlorophyll index value (CIV) (Spectrum Field Scout CM 1000 Chlorophyll Meter).
C. Results As can be seen from the FIGS. 29-32, the compositions as claimed improved the health of plants treated with said compositions compared with control plants.

A. Full Irrigation Treatments FIG. 29 demonstrates an improved quality rating of plants treated with the claimed compositions compared to control plants, under full irrigation treatment.

Figure 30:
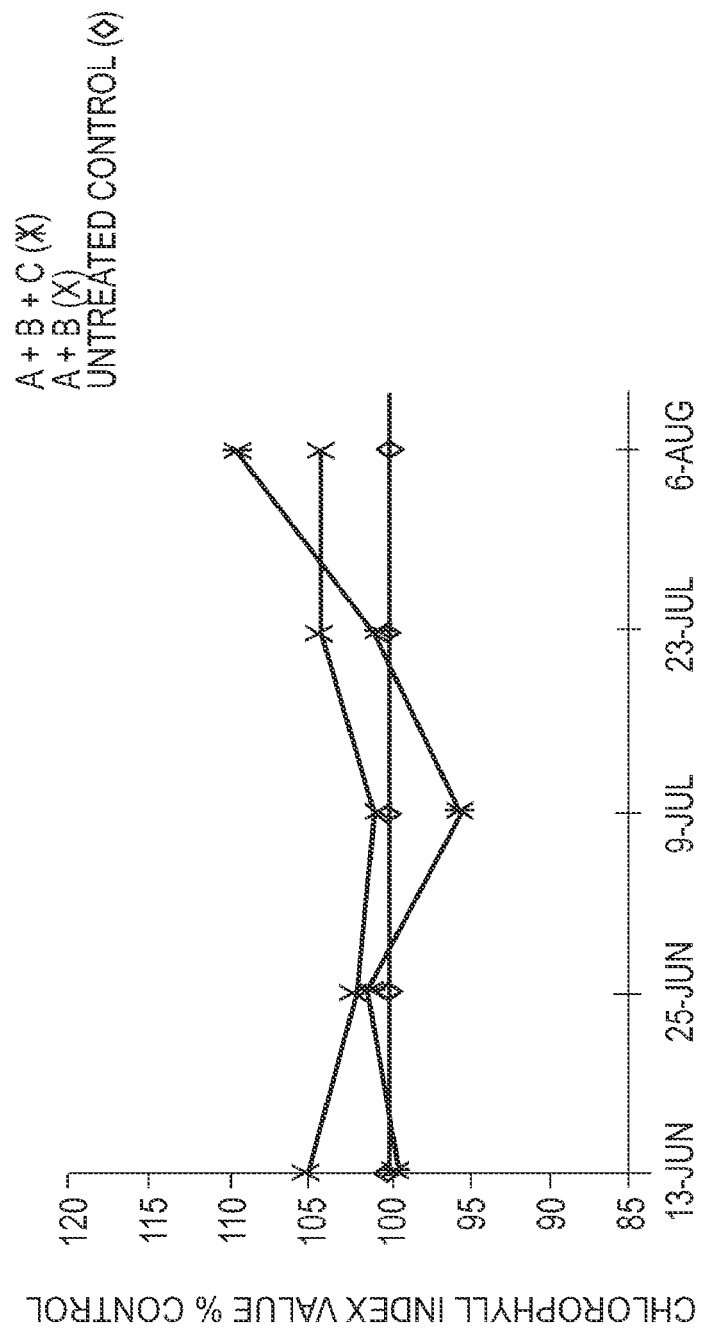
FIG. 30: shows results of an experiment on CIV in Bentgrass.

FIG. 30 demonstrates an improved chlorophyll index value (CIV) of plants treated with the claimed compositions compared to control plants, under full irrigation treatment.

B. 25% Reduced Irrigation Treatments

Figure 31:
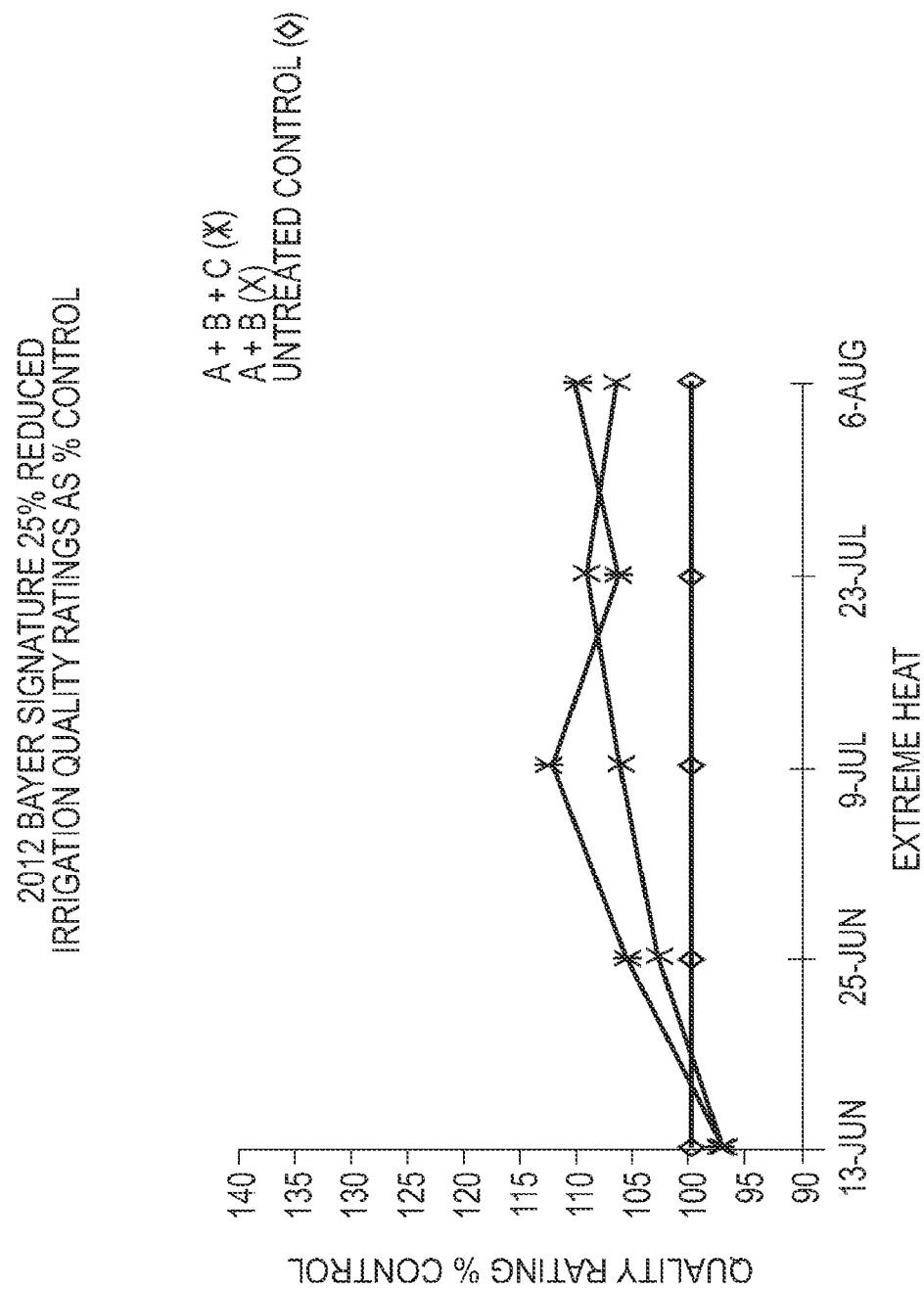
FIG. 31: shows results of an experiment on Quality Ratings in Bentgrass.

FIG. 31 demonstrates an improved quality rating of plants treated with the claimed compositions compared to control plants, under 25% reduced irrigation treatment.

Figure 32:
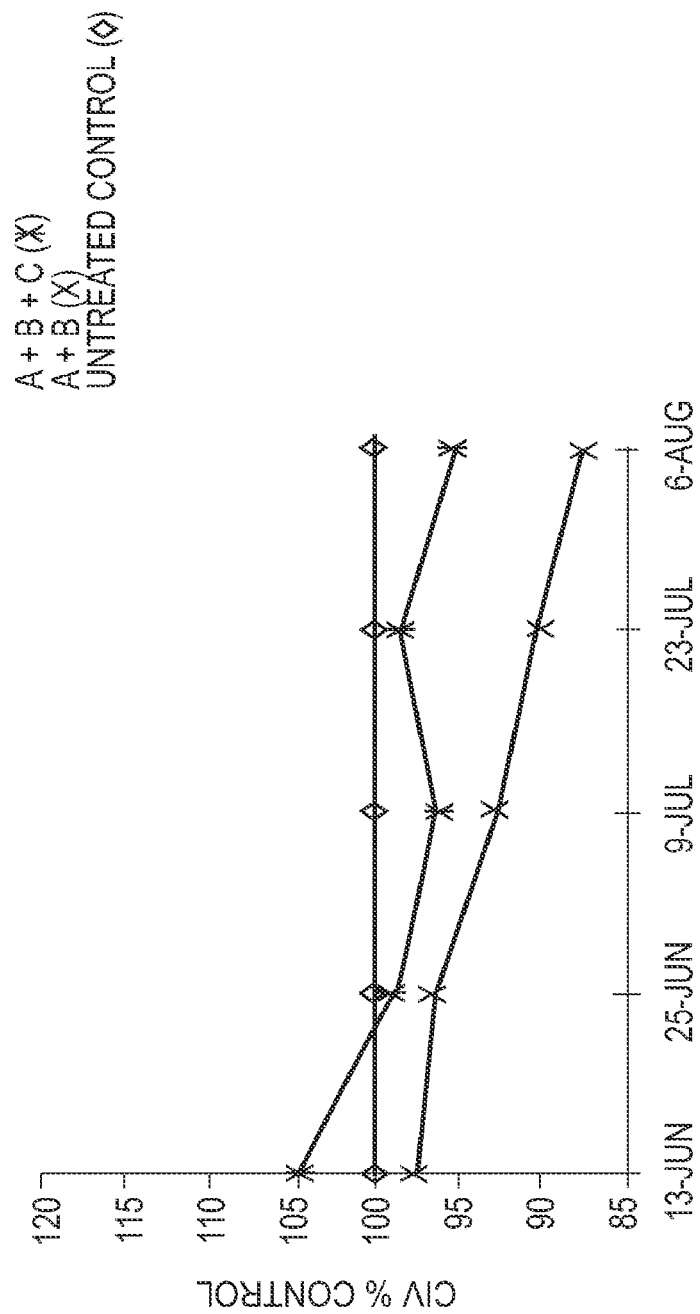
FIG. 32: shows results of an experiment on CIV in Bentgrass.

FIG. 32 demonstrates an improved chlorophyll index value (CIV) of plants treated with the claimed compositions compared to control plants, under 25% reduced irrigation treatment.

Example 4

The following test methods were used to evaluate compositions according to the invention.
A. Evaluated Compositions The following compositions, (A)-(H), depicted in Table 3, were utilized in the experiment. These compositions were evaluated as depicted in the below Tables 4-8. See top row of Tables 4-8 "Trials A-H."

TABLE 3

| Compositions (A)-(H) | |
|---|---|
| A = RUS | Sebacic acid + Mono and di-potassium salts + Polyoxyalkylene UV absorber |
| B = RUT | Vitamin C + Mono and di-potassium salts + Polyoxyalkylene UV absorber |
| C = RUU | N,N'-diformylurea + Mono and di-potassium salts + Polyoxyalkylene UV absorber |
| D = RUV | N,N'-diformylurea + Trinexapac ethyl + Polyoxyalkylene UV absorber |
| E = RUW | N,N'-diformylurea + Fosetyl Al + Polyoxyalkylene UV absorber |
| F = RUX | Trifloxystrobin + Mono and di-potassium salts + Polyoxyalkylene UV absorber |
| G = RUY | Mefenpyr + Mono and di-potassium salts + Polyoxyalkylene UV absorber |
| H = RUZ | N,N'-diformylurea + Mono and di-potassium salts + Phthalocyanine green pigment |

B. Evaluated Composition Components Rates of Application
RUZ composition components (H):
Antioxidant: N, N'-diformyl urea (28 to 29 g/L)
Plant Strengthener: Mono and di-potassium salts (208 to 263 g/L)
Radiation Manager: Phthalocyanine green pigment (1 ml/L)
RUY composition components (G):
Antioxidant: Mefenpyr (50 g ai/ha)
Plant Strengthener: Mono and di-potassium salts (208 to 263 g/L) vRadiation Manager: Polyoxyalkylene UV absorber (1 ml/L)
RUX composition components (F):
Antioxidant: Trifloxystrobin (229 g ai/ha)
Plant Strengthener: Mono and di-potassium salts (208 to 263 g/L)
Radiation Manager: Polyoxyalkylene UV absorber (1 ml/L)
RUW composition components (E):
Antioxidant: N, N'-diformyl urea (28 to 29 g/L)
Plant Strengthener: Fosetyl-Al (9770 g ai/ha)
Radiation Manager: Polyoxyalkylene UV absorber (1 ml/L)
RUV composition components (D):
Antioxidant: N, N'-diformyl urea (28 to 29 g/L)
Plant Strengthener: Trinexapac-ethyl (76.4 g ai/ha)
Radiation Manager: Polyoxyalkylene UV absorber (1 ml/L)
RUU composition components (C):
Antioxidant: N, N'-diformyl urea (28 to 29 g/L)
Plant Strengthener: Mono and di-potassium salts (208 to 263 g/L)
Radiation Manager: Polyoxyalkylene UV absorber (1 ml/L)

RUT composition components (B):
Antioxidant: Vitamin C (5000 g ai/ha)
Plant Strengthener: Mono and di-potassium salts (208 to 263 g/L)
Radiation Manager: Polyoxyalkylene UV absorber (1 ml/L)
RUS composition components (A):
Antioxidant: Sebacic acid (16 g ai/ha)
Plant Strengthener: Mono and di-potassium salts (208 to 263 g/L)
Radiation Manager: Polyoxyalkylene UV absorber (1 ml/L)
All applications were made at a volume of 2 gallons spray solution/1000 ft$^2$.

C. Methodology

Applications were made in greenhouses to seeded Tall Fescue, in cylinders under stressful conditions (maintained at 80% of field capacity in sandy soil).

Plants were clipped at 5 cm height and fertilized once, 14 days after seeding, with 12.5 kg Nitrogen of 20-20-20.

D. Treatments 2 applications of the compositions were made on 14 day intervals. Applications were initiated approximately 28 days after seeding. 3 replicates of 10 cm diameter x 25 cm deep cylinders to allow adequate area for rooting were utilized. Application volumes were 2 gallons per 1000 ft$^2$.

E. Assessment Variables

DAA=Days After "A" application of product.
DAB=Days After "B" application of product.

1. NDVI (Tables 4 and 5)

NDVI (Normalized Difference Vegetative Index) were recorded 24-27 DAA and 30-31 DAA.

As explained in Example 2, NDVI is characterized by the formula:

$$NDVI = NIR - VIS / NIR + VIS$$

NIR=Near-Infrared light
VIS—Visible light

Healthy plants vigorously absorb VIS and reflect NIR. There relative values change as plants become stressed.

2. Visual Color Rating (Table 6)

Visual Color Rating (1-9) were recorded 30-31 DAA.

Visual color ratings are recorded on a scale of 1 to 9. A color rating of 1 is no green color, as dead turf would appear. A color rating of 9 is ideal and represents excellent dark green color.

3. Shoot Dry Weight in Grams (Table 7)

Shoot dry weight in grams (clipped at 5 cm) were recorded at the completion of the study.

Shoot tissue was collect at the completion of the study as a measure of density based on leaf growth over time.

4. Root dry weight in grams (Table 8)

Root dry weight in grams were recorded at the completion of the study.

Root tissue generated over the course of the study was collected, dried and weighed after the study to assess the amount of root growth since the initiation of the study.

F. Results

Each of the below Tables 4-8 illustrate the various compositions, (A)-(H) from Table 3, which were utilized in the experiment. The compositions are set forth in the top row as Trials A-Trials H. The treatment column in Tables 4-8 indicates the treatment applied, i.e. what components from compositions (A)-(H) from Table 3 were present. Where (A) is the antioxidant, (B) is the plant strengthener, and (C) is the radiation manager.

The various Tables 4-8 demonstrate the variables measured during the course of the experiment, such as NDVI, Visual Color Rating, Shoot Dry Weight, and Root Dry Weight.

As can be seen from Tables 4-8, the compositions as claimed can improve the health of plants treated with said compositions compared with control plants.

TABLE 4

NDVI Measured at Days 24-27 DAA

| Treatment | Trial A | Trial B | Trial C | Trial D | Trial E | Trial F | Trial G | Trial H |
|---|---|---|---|---|---|---|---|---|
| Nontreated 100% water | 0.845175 | 0.9019 | 0.906775 | 0.89555 | 0.88485 | 0.934975 | n/a | 0.74 |
| Nontreated 80% water | 0.850175 | 0.8777 | 0.894925 | 0.859975 | 0.84645 | 0.897025 | n/a | 0.5275 |
| A + B + C 80% water | 0.869825 | 0.89125 | 0.86775 | 0.85975 | 0.83905 | 0.863375 | n/a | 0.675 |
| A + B 80% water | 0.822975 | 0.899425 | 0.898275 | 0.89205 | 0.855225 | 0.854125 | n/a | 0.54 |
| A + C 80% water | 0.833725 | 0.8932 | 0.9171 | 0.89 | 0.89175 | 0.88375 | n/a | 0.6625 |
| B + C 80% water | 0.83515 | 0.87775 | 0.90445 | 0.85025 | 0.8661 | 0.9253 | n/a | 0.6025 |

TABLE 5

NDVI Measured at Days 30-31 DAA

| Treatment | Trial A | Trial B | Trial C | Trial D | Trial E | Trial F | Trial G | Trial H |
|---|---|---|---|---|---|---|---|---|
| Nontreated 100% water | 0.903825 | 0.876625 | 0.89745 | 0.91035 | 0.86255 | 0.90095 | n/a | 0.7725 |
| Nontreated 80% water | 0.894625 | 0.90145 | 0.91065 | 0.90525 | 0.892775 | 0.9361 | n/a | 0.7525 |
| A + B + C 80% water | 0.886125 | 0.929325 | 0.908275 | 0.85325 | 0.87025 | 0.925675 | n/a | 0.735 |
| A + B 80% water | 0.83895 | 0.9103 | 0.892025 | 0.8853 | 0.89115 | 0.903325 | n/a | 0.7125 |

TABLE 5-continued

NDVI Measured at Days 30-31 DAA

| Treatment | Trial A | Trial B | Trial C | Trial D | Trial E | Trial F | Trial G | Trial H |
|---|---|---|---|---|---|---|---|---|
| A + C 80% water | 0.8861 | 0.898425 | 0.916675 | 0.932325 | 0.90825 | 0.9 | n/a | 0.75 |
| B + C 80% water | 0.881875 | 0.8849 | 0.917325 | 0.894275 | 0.880325 | 0.913675 | n/a | 0.7125 |

TABLE 6

Visual Color Rating Measured at Days 30-31 DAA

| Treatment | Trial A | Trial B | Trial C | Trial D | Trial E | Trial F | Trial G | Trial H |
|---|---|---|---|---|---|---|---|---|
| Nontreated 100% water | 6.8125 | 6.75 | 7.1875 | 6.75 | 6.8125 | 7.125 | n/a | 6.5625 |
| Nontreated 80% water | 6.875 | 6.625 | 6.875 | 6.6875 | 6.75 | 6.9375 | n/a | 6.9375 |
| A + B + C 80% water | 6.875 | 6.6875 | 6.8125 | 6.75 | 6.625 | 6.875 | n/a | 7 |
| A + B 80% water | 6.6875 | 6.75 | 7.125 | 6.75 | 6.6875 | 6.875 | n/a | 6.75 |
| A + C 80% water | 6.8125 | 6.9375 | 6.9375 | 6.625 | 6.8125 | 6.9375 | n/a | 7.25 |
| B + C 80% water | 6.8125 | 6.75 | 6.8125 | 6.875 | 6.6875 | 6.875 | n/a | 7.1875 |

TABLE 7

Shoot Dry Weight Clipped at 5 cm Measured at Completion of Study

| Treatment | Trial A | Trial B | Trial C | Trial D | Trial E | Trial F | Trial G | Trial H |
|---|---|---|---|---|---|---|---|---|
| Nontreated 100% water | 1.25 | 1.2075 | 2.0975 | 0.76 | 0.825 | 1.125 | 1.4375 | 1.5125 |
| Nontreated 80% water | 1.1625 | 1.1475 | 1.7925 | 0.83 | 0.95 | 1.3075 | 1.28 | 1.7525 |
| A + B + C 80% water | 0.9925 | 1.2025 | 1.7125 | 0.805 | 0.7575 | 0.7775 | 2.45 | 1.6475 |
| A + B 80% water | 1.0275 | 1.1125 | 1.7825 | 0.71 | 0.88 | 0.785 | 1.085 | 2.3125 |
| A + C 80% water | 0.885 | 1.1725 | 2.1175 | 0.815 | 0.6825 | 0.9725 | 1.8775 | 1.825 |
| B + C 80% water | 1.2225 | 1.125 | 2.05 | 0.77 | 0.8125 | 1.22 | 1.5475 | 1.605 |

TABLE 8

Root Dry Weight Measured at Completion of Study

| Treatment | Trial A | Trial B | Trial C | Trial D | Trial E | Trial F | Trial G | Trial H |
|---|---|---|---|---|---|---|---|---|
| Nontreated 100% water | 1.1075 | 1.8175 | 1.445 | 2.6375 | 2.0425 | 1.3625 | 0.955 | 4.68 |
| Nontreated 80% water | 1.095 | 1.19 | 1.375 | 1.57 | 2.0575 | 1.1 | 1.1675 | 1.8425 |
| A + B + C 80% water | 1.275 | 1.4375 | 1.375 | 1.5425 | 1.7475 | 1.4675 | 1.24 | 1.895 |
| A + B 80% water | 1.035 | 1.355 | 1.6075 | 1.7325 | 1.805 | 1.4475 | 1.13 | 1.89 |
| A + C 80% water | 1.3075 | 1.4125 | 1.53 | 1.9975 | 1.8375 | 1.135 | 1.0825 | 1.6575 |
| B + C 80% water | 1.995 | 1.56 | 1.5125 | 2.1 | 2.2375 | 1.37 | 1.005 | 1.8075 |

The invention claimed is:

1. A method for improving one or more of plant quality, density, color, or plant cell turgidity, comprising: applying to a plant or soil a composition comprising:
    (i) an antioxidant;
    (ii) a radiation manager;
    and
    (iii) a plant growth regulator;
    wherein the antioxidant (i) comprises N-formyl urea, and wherein the (iii) plant growth regulator comprises daminozide or prohexadione-Ca.

2. The method according to claim 1, wherein the radiation manager (ii) comprises:
    (a) a colorant that screens UV and high energy visible blue light, and/or
    (b) a salt or oxide of a higher atomic weight metal that is micronized or in the form of a nanoparticle.

3. The method according to claim 1, wherein the radiation manager (ii) comprises a phthalocyanine copper pigment.

4. The method according to claim 1, wherein the radiation manager (ii) comprises a polyoxyalkylene UV absorber.

5. The method according to claim 1, wherein the plant is growing under a condition of reduced water irrigation.

6. The method according to claim 1, wherein the treated plant exhibits improved green color, higher chlorophyll content, improved shoot density, and/or better plot soil moisture when compared to a non-treated plant before, during, and/or after the condition of reduced water irrigation.

7. The method according to claim 1, wherein the composition further comprises
    (iv) a plant strengthener.

8. The method according to claim 7, wherein the plant strengthener (iv) is at least one selected from the group consisting of a phosphite, phosphonate, phosphorous containing compound and salt thereof, inducer of systemic resistance, and plant hormone.

9. The method according to claim 7, wherein the plant strengthener (iv) comprises a di- and mono-potassium salt of phosphorous acid.

10. The method according to claim 7, wherein
    the radiation manager (ii) comprises phthalocyanine green pigment.

11. The method according to claim 1, wherein the (iii) plant growth regulator comprises daminozide.

12. The method according to claim 1, wherein the (iii) plant growth regulator comprises prohexadione-Ca.

* * * * *